US012378560B2

(12) United States Patent
Mirkin et al.

(10) Patent No.: US 12,378,560 B2
(45) Date of Patent: Aug. 5, 2025

(54) SEQUENCE MULTIPLICITY WITHIN SPHERICAL NUCLEIC ACIDS

(71) Applicant: NORTHWESTERN UNIVERSITY, Evanston, IL (US)

(72) Inventors: Chad A. Mirkin, Wilmette, IL (US); Ziyin Huang, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 738 days.

(21) Appl. No.: 17/084,460

(22) Filed: Oct. 29, 2020

(65) Prior Publication Data
US 2021/0123057 A1 Apr. 29, 2021

Related U.S. Application Data

(60) Provisional application No. 62/927,456, filed on Oct. 29, 2019.

(51) Int. Cl.
C12N 15/117 (2010.01)
A61K 31/7088 (2006.01)
A61K 31/7125 (2006.01)
A61K 47/69 (2017.01)

(52) U.S. Cl.
CPC ........ C12N 15/117 (2013.01); A61K 31/7088 (2013.01); A61K 31/7125 (2013.01); A61K 47/6911 (2017.08); C12N 2310/17 (2013.01); C12N 2310/315 (2013.01); C12N 2320/32 (2013.01); C12Q 2525/307 (2013.01)

(58) Field of Classification Search
None
See application file for complete search history.

(56) References Cited

U.S. PATENT DOCUMENTS

| 3,687,808 A | 8/1972 | Merigan et al. |
| 4,469,863 A | 9/1984 | Ts et al. |
| 4,476,301 A | 10/1984 | Imbach et al. |
| 4,489,055 A | 12/1984 | Couvreur et al. |
| 4,845,205 A | 7/1989 | Huynh et al. |
| 4,981,957 A | 1/1991 | Lebleu et al. |
| 5,008,050 A | 4/1991 | Cullis et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |

(Continued)

FOREIGN PATENT DOCUMENTS

| AU | 64763/98 A | 7/1998 |
| CN | 101850117 A | 10/2010 |

(Continued)

OTHER PUBLICATIONS

European Application No. 14883485, European Search Report and Opinion, mailed May 9, 2017.
Fang et al., Functionalized nanoparticles with long-term stability in biological media, Small, 5(14):1637-1641 (2009).
Farokhzad et al., Nanomedicine: developing smarter therapeutic and diagnostic modalities, Drug Delivery Rev., 58(14):1456-1459 (2006).
Fattal et al., Biodegradable polyalkylcyanoacrylate nanoparticles for the delivery of oligonucleotides, J. Controlled Release, 53(1-3):137-143 (1998).
Ferrari, Cancer nanotechnology: opportunities and challenges, Nature Reviews Cancer, 5:161-171 (2005).

(Continued)

Primary Examiner — Brian Whiteman
(74) Attorney, Agent, or Firm — MARSHALL, GERSTEIN & BORUN LLP

(57) ABSTRACT

The present disclosure is directed to spherical nucleic acids (SNAs) comprising a nanoparticle core and an oligonucleotide shell attached to the external surface of the nanoparticle core, wherein the oligonucleotide shell comprises a mixture of class A CpG oligonucleotides and class B CpG oligonucleotides. The disclosure also provides methods of using the SNAs for, e.g., regulation of an immune response and gene regulation.

23 Claims, 23 Drawing Sheets
Specification includes a Sequence Listing.

(56) References Cited

U.S. PATENT DOCUMENTS

| | | |
|---|---|---|
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,814,666 A | 9/1998 | Green et al. |
| 5,830,653 A | 11/1998 | Froehler et al. |
| 5,955,589 A | 9/1999 | Cook et al. |
| 6,005,096 A | 12/1999 | Matteucci et al. |
| 6,051,698 A | 4/2000 | Janjic et al. |
| 6,218,371 B1 | 4/2001 | Krieg et al. |
| 6,239,116 B1 | 5/2001 | Krieg et al. |
| 6,271,209 B1 | 8/2001 | Smith et al. |
| 6,406,705 B1 | 6/2002 | Davis et al. |
| 6,552,006 B2 | 4/2003 | Raz et al. |
| 6,677,153 B2 | 1/2004 | Iversen |
| 7,223,833 B1 | 5/2007 | Nielsen et al. |
| 7,238,472 B2 | 7/2007 | Mirkin et al. |
| 7,667,004 B2 | 2/2010 | Zhong et al. |
| 7,833,992 B2 | 11/2010 | Vargeese et al. |
| 7,893,224 B2 | 2/2011 | Manoharan et al. |
| 8,034,376 B2 | 10/2011 | Manoharan et al. |
| 8,148,344 B2 | 4/2012 | Akinc et al. |
| 8,252,756 B2 | 8/2012 | Mirkin et al. |
| 8,461,117 B2 | 6/2013 | Sufi et al. |
| 8,507,200 B2 | 8/2013 | Mirkin et al. |
| 8,664,407 B2 | 3/2014 | Chen et al. |
| 8,754,062 B2 | 6/2014 | De et al. |
| 8,791,250 B2 | 7/2014 | Nakayama et al. |
| 8,809,292 B2 | 8/2014 | Tan et al. |
| 8,846,080 B2 | 9/2014 | Biemans et al. |
| 8,933,046 B2 | 1/2015 | Machuy et al. |
| 8,940,310 B2 | 1/2015 | Barrat et al. |
| 8,999,947 B2 | 4/2015 | Mirkin et al. |
| 9,006,197 B2 | 4/2015 | Bumcrot et al. |
| 9,062,310 B2 | 6/2015 | De Fougerolles et al. |
| 9,139,827 B2 | 9/2015 | Mirkin et al. |
| 9,376,690 B2 | 6/2016 | Mirkin et al. |
| 9,415,109 B2 | 8/2016 | Kumar et al. |
| 9,422,562 B2 | 8/2016 | Defougerolles et al. |
| 9,506,056 B2 | 11/2016 | Mirkin et al. |
| 9,687,448 B2 | 6/2017 | Akinc et al. |
| 9,693,957 B2 | 7/2017 | Lin et al. |
| 9,719,089 B2 | 8/2017 | Mirkin et al. |
| 9,757,475 B2 | 9/2017 | Mirkin et al. |
| 9,844,562 B2 | 12/2017 | Mirkin et al. |
| 9,868,693 B2 | 1/2018 | Benenato |
| 9,868,955 B2 | 1/2018 | Guiducci et al. |
| 9,889,209 B2 | 2/2018 | Mirkin et al. |
| 9,890,427 B2 | 2/2018 | Mirkin et al. |
| 9,901,616 B2 | 2/2018 | Dhar et al. |
| 9,950,068 B2 | 4/2018 | De et al. |
| 9,963,700 B2 | 5/2018 | Gollob et al. |
| 10,098,958 B2 | 10/2018 | Mirkin et al. |
| 10,182,988 B2 | 1/2019 | Mirkin et al. |
| 10,208,310 B2 | 2/2019 | Mader et al. |
| 10,301,622 B2 | 5/2019 | Mirkin et al. |
| 10,370,656 B2 | 8/2019 | Mirkin et al. |
| 10,370,661 B2 | 8/2019 | Mirkin et al. |
| 10,391,116 B2 | 8/2019 | Mirkin et al. |
| 10,398,784 B2 | 9/2019 | Mirkin et al. |
| 10,472,628 B2 | 11/2019 | De Fougerolles et al. |
| 10,507,246 B2 * | 12/2019 | Lin ................. C12N 15/115 |
| 10,507,249 B2 | 12/2019 | Guild et al. |
| 10,563,244 B2 | 2/2020 | Mrksich et al. |
| 10,792,251 B2 | 10/2020 | Mirkin et al. |
| 10,837,018 B2 | 11/2020 | Radovic-Moreno et al. |
| 10,894,963 B2 | 1/2021 | Radovic-Moreno et al. |
| 11,123,294 B2 | 9/2021 | Radovic-Moreno et al. |
| 11,433,131 B2 | 9/2022 | Mirkin et al. |
| 11,690,920 B2 | 7/2023 | Mirkin et al. |
| 2002/0172711 A1 | 11/2002 | Martin et al. |
| 2003/0026782 A1 | 2/2003 | Krieg |
| 2003/0044354 A1 | 3/2003 | Carpenter et al. |
| 2003/0147966 A1 | 8/2003 | Franzen et al. |
| 2003/0170162 A1 | 9/2003 | Nayfeh et al. |
| 2004/0014956 A1 | 1/2004 | Woolf et al. |
| 2004/0033197 A1 | 2/2004 | Madar et al. |
| 2004/0053384 A1 | 3/2004 | Sligar et al. |
| 2004/0158051 A1 | 8/2004 | Ozkan et al. |
| 2004/0170560 A1 | 9/2004 | Fossheim et al. |
| 2004/0219565 A1 | 11/2004 | Kauppinen et al. |
| 2005/0130167 A1 | 6/2005 | Bao et al. |
| 2005/0232866 A1 | 10/2005 | Melchior et al. |
| 2006/0014191 A1 | 1/2006 | Lao et al. |
| 2006/0083781 A1 | 4/2006 | Shastri et al. |
| 2006/0292174 A1 | 12/2006 | De et al. |
| 2007/0243136 A1 | 10/2007 | Fisher et al. |
| 2007/0298257 A1 | 12/2007 | Ludwig et al. |
| 2008/0175893 A1 | 7/2008 | Huang et al. |
| 2008/0181928 A1 | 7/2008 | Hakimi-Mehr et al. |
| 2008/0194463 A1 | 8/2008 | Weller et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0065822 A1 | 3/2009 | Hwang |
| 2009/0209629 A1 | 8/2009 | Mirkin et al. |
| 2009/0246142 A1 | 10/2009 | Bhatia et al. |
| 2009/0322327 A1 | 12/2009 | Gao |
| 2010/0003317 A1 | 1/2010 | Akinc et al. |
| 2010/0092486 A1 | 4/2010 | Kandimalla et al. |
| 2010/0129808 A1 | 5/2010 | Mirkin et al. |
| 2010/0136682 A1 | 6/2010 | Mirkin et al. |

(56) References Cited

U.S. PATENT DOCUMENTS

| | | |
|---|---|---|
| 2010/0144848 A1 | 6/2010 | Vogel et al. |
| 2010/0166842 A1 | 7/2010 | Lu et al. |
| 2010/0203149 A1 | 8/2010 | Radosz et al. |
| 2010/0233270 A1 | 9/2010 | Mirkin et al. |
| 2011/0020242 A1 | 1/2011 | Zheng et al. |
| 2011/0052680 A1 | 3/2011 | Hendrickson et al. |
| 2011/0052697 A1 | 3/2011 | Farokhzad et al. |
| 2011/0159081 A1 | 6/2011 | Biemans et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2012/0149843 A1 | 6/2012 | Chien et al. |
| 2012/0282186 A1 | 11/2012 | Mirkin et al. |
| 2012/0283316 A1 | 11/2012 | Mirkin et al. |
| 2013/0028857 A1 | 1/2013 | Gao et al. |
| 2013/0089614 A1 | 4/2013 | Zhang et al. |
| 2013/0123333 A1 | 5/2013 | Mirkin et al. |
| 2013/0149374 A1 | 6/2013 | Lee et al. |
| 2013/0172404 A1 | 7/2013 | Mirkin et al. |
| 2013/0196951 A1 | 8/2013 | Schoenfisch et al. |
| 2013/0252852 A1 | 9/2013 | Pfeiffer et al. |
| 2013/0295129 A1 | 11/2013 | Irvine et al. |
| 2013/0309172 A1 | 11/2013 | Berlin et al. |
| 2013/0315831 A1 | 11/2013 | Shi et al. |
| 2014/0065425 A1 | 3/2014 | Bogdanov |
| 2014/0068429 A1 | 3/2014 | Belbin et al. |
| 2014/0086849 A1* | 3/2014 | McKenna ............... A61K 39/39 424/234.1 |
| 2014/0194493 A1 | 7/2014 | Sah et al. |
| 2014/0314739 A1 | 10/2014 | Petrovsky |
| 2015/0031745 A1 | 1/2015 | Mirkin et al. |
| 2015/0064265 A1 | 3/2015 | Fahmy et al. |
| 2015/0111790 A1 | 4/2015 | Ategeka et al. |
| 2015/0259680 A1 | 9/2015 | Mirkin et al. |
| 2015/0352138 A1 | 12/2015 | Mirkin et al. |
| 2016/0108123 A1 | 4/2016 | Freeman et al. |
| 2016/0186138 A1* | 6/2016 | Chelyapov ............ C12N 5/0646 435/375 |
| 2016/0186178 A1 | 6/2016 | Radovic-Moreno et al. |
| 2016/0194642 A1 | 7/2016 | Gryaznov et al. |
| 2016/0206747 A1 | 7/2016 | Mirkin et al. |
| 2016/0237429 A1 | 8/2016 | Cubillos-Ruiz et al. |
| 2016/0274134 A1 | 9/2016 | Mutharasan et al. |
| 2016/0281086 A1 | 9/2016 | Mirkin et al. |
| 2016/0310425 A1 | 10/2016 | Mirkin et al. |
| 2017/0137809 A1 | 5/2017 | Mirkin et al. |
| 2017/0157048 A1 | 6/2017 | Radovic-Moreno et al. |
| 2017/0232109 A1 | 8/2017 | Mirkin et al. |
| 2018/0072810 A1 | 3/2018 | Afar et al. |
| 2018/0080058 A1 | 3/2018 | Mrksich et al. |
| 2018/0085390 A1 | 3/2018 | Mirkin et al. |
| 2018/0153822 A1 | 6/2018 | Karve et al. |
| 2018/0187189 A1 | 7/2018 | Mirkin et al. |
| 2018/0193484 A1 | 7/2018 | Mirkin et al. |
| 2018/0214376 A1 | 8/2018 | Giljohann |
| 2018/0222982 A1 | 8/2018 | Dranoff et al. |
| 2019/0032087 A1 | 1/2019 | Cullis et al. |
| 2019/0225968 A1 | 7/2019 | Anderson et al. |
| 2020/0022913 A1 | 1/2020 | Mirkin et al. |
| 2020/0101156 A1 | 4/2020 | Mirkin et al. |
| 2020/0246484 A1 | 8/2020 | Mirkin et al. |
| 2020/0384104 A1 | 12/2020 | Mirkin et al. |
| 2021/0039062 A1 | 2/2021 | Mirkin et al. |
| 2021/0052497 A1 | 2/2021 | Mirkin et al. |
| 2021/0087221 A1 | 3/2021 | Mirkin et al. |
| 2021/0102211 A1 | 4/2021 | Radovic-Moreno et al. |
| 2021/0122778 A1 | 4/2021 | Mirkin et al. |
| 2021/0189397 A1 | 6/2021 | Mirkin et al. |
| 2021/0220454 A1 | 7/2021 | Mirkin et al. |
| 2021/0236651 A1 | 8/2021 | Mirkin et al. |
| 2021/0332495 A1 | 10/2021 | Mirkin et al. |
| 2022/0010302 A1 | 1/2022 | Mirkin et al. |
| 2022/0056220 A1 | 2/2022 | Mirkin et al. |
| 2022/0175956 A1 | 6/2022 | Mirkin et al. |
| 2022/0288181 A1 | 9/2022 | Mirkin et al. |
| 2022/0288225 A1 | 9/2022 | Wu |
| 2022/0348985 A1 | 11/2022 | Mirkin et al. |
| 2022/0349005 A1 | 11/2022 | Mirkin et al. |
| 2022/0364095 A1 | 11/2022 | Mirkin et al. |
| 2022/0370490 A1 | 11/2022 | Mirkin et al. |
| 2022/0387585 A1 | 12/2022 | Mirkin et al. |
| 2023/0088835 A1 | 3/2023 | Mirkin et al. |
| 2023/0147733 A1 | 5/2023 | Mirkin et al. |

FOREIGN PATENT DOCUMENTS

| | | | |
|---|---|---|---|
| CN | 103212089 A | 7/2013 | |
| EP | 1072679 A2 | 1/2001 | |
| EP | 2162117 A2 | 3/2010 | |
| EP | 2399608 A1 | 12/2011 | |
| HK | 1152529 | 3/2012 | |
| WO | 96/34876 A1 | 11/1996 | |
| WO | 97/12896 A1 | 4/1997 | |
| WO | 98/39352 A1 | 9/1998 | |
| WO | 99/14226 A2 | 3/1999 | |
| WO | 2001/062895 A2 | 8/2001 | |
| WO | 02/96262 A2 | 12/2002 | |
| WO | 03/86280 A2 | 10/2003 | |
| WO | 2005/063201 A2 | 7/2005 | |
| WO | 2005/063288 A1 | 7/2005 | |
| WO | 2006/138145 A1 | 12/2006 | |
| WO | 2007/008463 A2 | 1/2007 | |
| WO | 2007/047455 A2 | 4/2007 | |
| WO | 2007/064857 A2 | 6/2007 | |
| WO | 2007/096134 A1 | 8/2007 | |
| WO | 2008/014979 A2 | 2/2008 | |
| WO | 2008/151022 A2 | 12/2008 | |
| WO | 2008/151049 A2 | 12/2008 | |
| WO | 2009/061515 A1 | 5/2009 | |
| WO | 2009/073984 A1 | 6/2009 | |
| WO | 2009/120887 A2 | 10/2009 | |
| WO | 2010/060110 A1 | 5/2010 | |
| WO | 2010/105209 A1 | 9/2010 | |
| WO | 2010/120420 A1 | 10/2010 | |
| WO | 2011/017456 A2 | 2/2011 | |
| WO | 2011/028850 A1 | 3/2011 | |
| WO | 2012/055933 A1 | 5/2012 | |
| WO | 2012/068470 A2 | 5/2012 | |
| WO | 2012/170930 A1 | 12/2012 | |
| WO | 2013/012628 A2 | 1/2013 | |
| WO | 2013/028843 A2 | 2/2013 | |
| WO | 2013/049941 A1 | 4/2013 | |
| WO | 2013/151771 A1 | 10/2013 | |
| WO | 2014/169264 A2 | 10/2014 | |
| WO | 2015/013673 A1 | 1/2015 | |
| WO | 2015/013675 A1 | 1/2015 | |
| WO | 2015/055630 A1 | 4/2015 | |
| WO | 2015/126502 A2 | 8/2015 | |
| WO | 2015/187966 A1 | 12/2015 | |
| WO | 2016/028940 A1 | 2/2016 | |
| WO | 2016/081911 A2 | 5/2016 | |
| WO | WO-2016115320 A1 * | 7/2016 | ........... A61K 47/544 |
| WO | 2017/031086 A1 | 2/2017 | |
| WO | 2017/035278 A1 | 3/2017 | |
| WO | 2017/136467 A1 | 8/2017 | |
| WO | 2017/193081 A1 | 11/2017 | |
| WO | 2018/022694 A1 | 2/2018 | |
| WO | 2018/067302 A2 | 4/2018 | |
| WO | 2018/152327 A1 | 8/2018 | |
| WO | 2018/175445 A1 | 9/2018 | |
| WO | 2018/213585 A1 | 11/2018 | |
| WO | WO-2018201090 A1 * | 11/2018 | ........... A61K 31/708 |
| WO | 2019/032241 A1 | 2/2019 | |
| WO | 2019/070890 A1 | 4/2019 | |
| WO | 2019/118883 A1 | 6/2019 | |
| WO | 2019/200262 A1 | 10/2019 | |
| WO | 2019/217870 A1 | 11/2019 | |
| WO | 2020/056341 A2 | 3/2020 | |
| WO | 2020/068905 A1 | 4/2020 | |
| WO | WO-2020072833 A1 * | 4/2020 | ............ A61K 35/15 |
| WO | 2020/118259 A1 | 6/2020 | |
| WO | 2020/168005 A1 | 8/2020 | |
| WO | 2020/181144 A1 | 9/2020 | |
| WO | 2020/219985 A1 | 10/2020 | |

(56) References Cited

FOREIGN PATENT DOCUMENTS

| | | |
|---|---|---|
| WO | 2020/257674 A1 | 12/2020 |
| WO | 2021/034956 A2 | 2/2021 |
| WO | 2021/177996 A1 | 9/2021 |
| WO | 2021/207630 A1 | 10/2021 |
| WO | 2022/155149 A1 | 7/2022 |
| WO | 2022/183043 A1 | 9/2022 |
| WO | 2022/192038 A1 | 9/2022 |
| WO | 2022/204427 A1 | 9/2022 |
| WO | 2022/212564 A1 | 10/2022 |
| WO | 2023/092040 A1 | 5/2023 |
| WO | 2023/107389 A1 | 6/2023 |

OTHER PUBLICATIONS

Ferrer et al., Dual Toll-Like Receptor Targeting Liposomal Spherical Nucleic Acids, Bioconjug. Chem., 30:944-951 (2019).
Forster, Zwischenmolekulare Energiewanderung und Fluoreszenz, Annalen der Physik, 437:55-75 (2006).
Freier et al., The ups and downs of nucleic acid duplex stability: structure-stability studies on chemically-modified DNA:RNA duplexes, Nucl. Acid. Res., 25:4429-4443 (1997).
Frey et al., Bionanotechnology for vaccine design, Current opinion in biotechnology, 52:80-88 (2018).
Giljohann et al., Gene regulation with polyvalent siRNA-nanoparticle conjugates, J. Am. Chem. Soc., 131(6):2072-2073 (2009).
Giljohann et al., Oligonucleotide loading determines cellular uptake of DNA-modified gold nanoparticles, Nano Letters, 7(12):3818-3821 (2007).
Grijalva et al., Oligonucleotide delivery: a patent review (2010-2013), Expert Opin. Ther. Pat., 24(7):801-819 (2014).
Gu et al., Biomaterials and emerging anticancer therapeutics: engineering the microenvironment, Nature Reviews Cancer, 16:56-66 (2016).
Guan et al., RNA-Based Immunostimulatory Liposomal Spherical Nucleic Acids as Potent TLR7/8 Modulators, Small, 14:e1803284 (2018).
Gulley et al., Avelumab (MSB0010718C), an anti-PD-L1 antibody, in advanced NSCLC patients: A phase 1b, open-label expansion trial in patients progressing after platinum-based chemotherapy, Journal of Clinical Oncology, 33(15):8034-8034 (2015).
Gunnarsson et al., Liposome-based chemical barcodes for single molecule DNA detection using imaging mass soectrometry, Nano. Lett., 10:732-737 (2010).
Gunnarsson et al., Single-molecule detection and mismatch discrimination of unlabeled DNA targets, Nano Lett., 8:183-188 (2008).
Hanagata, Structure-dependent immunostimulatory effect of CpG oligodeoxynucleotides and their delivery system, Int. J. Nanomedicine, 7:2181-2195 (2012).
Hatakeyama et al., Development of a novel systemic gene delivery system for cancer therapy with a tumor-specific cleavable PEG-lipid, Gene Ther., 14(1)68-77 (2006).
Hayashi, Ultrafine particles, J. Vac. Sci. Technol., 5(4):1375-1384 (1987).
Heit et al., CpG-DNA Aided Cross-Priming by Cross-Presenting B Cells, J. Immunol., 172(3):1501-1507 (2004).
Heit et al., Protective CD8 T Cell Immunity Triggered by CpG-Protein Conjugates Competes with the Efficacy of Live Vaccines, J. Immunol., 174(7):4373-4380 (2005).
Henglein et al., Absorption spectrum and some chemical reactions of colloidal platinum in aqueous solution, J. Phys. Chem., 99(38):14129-14136 (1995).
Henglein, Mechanism of reactions on colloidal microelectrodes and size quantization effects, Top. Curr. Chem., 143:113-180 (1988).
Henglein, Small-particle research: physicochemical properties of extremely small colloidal metal and semiconductor particles, Chem. Rev., 89(8):1861-1873 (1989).

Herbath et al., Coadministration of Antigen-Conjugated and Free CpG: Effects of in Vitro and in Vivo Interactions in a Murine Model, Immunol. Lett., 160(2):178-185 (2014).
Hirosue et al., Antigen Delivery to Dendritic Cells by Poly(Propylene Sulfide) Nanoparticles with Disulfide Conjugated Peptides: Cross-Presentation and T Cell Activation, Vaccine 28(50):7897-7906 (2010).
Hope et al., Generation of multilamellar and unilamellar phospholipid vesicles, Chemistry and Physics of Lipids, 40:89-107(1986).
Hope et al., Production of large unilamellar vesicles by a rapid extrusion procedure: characterization of size distribution, trapped volume and ability to maintain a membrane potential, Biochim Biophys Acta, Jan. 10, 1985, vol. 812, No. 1, pp. 55-65.
Houot et al., T-cell modulation combined with intratumoral CpG cures lymphoma in a mouse model without the need for chemotherapy, Blood, 113(15):3546-3552 (2009).
Hu et al., Elucidating the impact of traceless conjugation chemistry on the immunostimulatory efficacy of protein spherical nucleic acids, Northwestern Int. Ins. For Nano., (2019).
Hu et al., Impact of protein spherical nucleic acid design parameters on immunostimulation, Northwestern Int. Ins. For Nano., (2020).
Hurst et al., Maximizing DNA loading on a range of gold nanoparticle sizes, Anal. chem., 78(24):8313-8318 (2006).
International Application No. PCT/US18/65765, International Preliminary Report on Patentability, mailed Jun. 25, 2020.
International Application No. PCT/US18/65765, International Search Report and Written Opinion, mailed Mar. 14, 2019.
International Application No. PCT/US2018/054221, International Preliminary Report on Patentability, mailed Apr. 16, 2020.
International Application No. PCT/US2018/054221, International Search Report and Written Opinion, mailed Dec. 26, 2018.
International Preliminary Report on Patentability, United States Patent Office, PCT/US2014/068429, dated Jun. 7, 2016.
International Search Report and Written Opinion of the International Search Authority, United States Patent Office, PCT/US2014/068429, dated Aug. 10, 2015.
Irvine et al., Engineering synthetic vaccines using cues from natural immunity, Nature materials, 12:978-990 (2013).
Irvine et al., Synthetic nanoparticles for vaccines and immunotherapy, Chemical reviews, 115(19):11109-11146 (2015).
Irvine, Drug delivery: One nanoparticle, one kill. Nat. Mater., 10:342 (2011).
Jahn et al., Microfluidic directed formation of liposomes of controlled size, Langmuir, 23(11):6289-6293 (2007).
Jakobsen et al., Assembly of liposomes controlled by triple helix formation, Bioconjugate Chem., 24:1485-1495 (2013).
Jennifer Martinez, Xiaopei Huang, and Yiping Yang. "Toll-like receptor 8-mediated activation of murine plasmacytoid dendritic cells by vaccinia viral DNA." Proceedings of the National Academy of Sciences, vol. 107, No. 4, Apr. 6, 2010, pp. 6442-6447 and one supplemental page. (Year: 2010).
Jensen et al., Spherical nucleic acid nanoparticle conjugates as an RNAi-based therapy for glioblastoma, Sci. Transl. Med., 5(209):209ra152-209ra152 (2013).
Jiang et al., Tumor imaging by means of proteolytic activation of cell-penetrating peptides, Proc. Natl. Acad. Sci. U.S.A., 101(51):17867-17872 (2004).
Jin et al., What controls the melting properties of DNA-linked gold nanoparticle assemblies?, J. Am. Chem. Soc., 125:1643-54 (2003).
Jones et al., Programmable materials and the nature of the DNA bond, Science, 347(6224):1260901 (2015).
Jones et al., Releasable Luciferin Transporter Conjugates: Tools for the Real-Time Analysis of Cellular Uptake and Release, J. Am. Chem. Soc., 128(20):6526-6527 (2006).
Agbasi-Porter et al., Transcription inhibition using oligonucleotide-modified gold nanoparticles, Bioconiugate Chem., 17(5):1178-83 (2006).
Aguilera et al., Systemic in vivo distribution of activatable cell penetrating peptides is superior to that of cell penetrating peptides, Integrative Biology, 1(5-6):371-381 (2009).
Ahmadi et al., Shape-controlled synthesis of colloidal platinum nanoparticles, Science, 272(5270):1924-6 (1996).

(56) References Cited

OTHER PUBLICATIONS

Alemdaroglu et al., DNA block copolymer micelles—A combinatorial tool for cancer tanotechnology, Advanced materials, 20:899 (2008).
Ali et al., Vaccines combined with immune checkpoint antibodies promote cytotoxic T-cell activity and tumor eradication, Cancer Immunology Research, 4(2):95-100 (2016).
Altschul et al., Basic local alignment search tool, J. Mol. Biol., 215(3):403-410 (1990).
Andrews et al., Conjugation of lipid and CpG-containing oligonucleotide yields an efficient method for liposome incorporation, bioconjugate Chem., 22:1279-1286 (2011).
Ashley et al., The targeted delivery of multicomponent cargos to cancer cells by nanoporous particle-supported lipid bilayers, Nat. Mater., 10:389-397 (2011).
Bae et al., Targeted drug delivery to tumors: myths, reality and possibility, J. Control Release, 153(3)1198-205 (2011).
Bahnemann, in Photochemical conversion and storage of solar energy (eds. Pelizetti and Schiavello, 251 (1991).
Bakker, Melanocyte lineage-specific antigen gp100 in T cellmediated immunotherapy of melanoma, (1996).
Banchelli et al., Phospholipid membranes decorated by cholesterol-based oligonucleotides as soft hybrid nanostructures, J. Phys. Chem. B., 112:10942-10952 (2008).
Banga et al., Cross-linked micellar spherical nucleic acids from thermoresponsive templates, J. Am. Chem. Soc., (2017).
Banga et al., Liposomal spherical nucleic acids, J. Am. Chem. Soc., 136(28):9866-9869 (2014).
Basu et al., Temperature and salt dependence of higher order structure formation by antisense c-myc and c-myb phosphorothioate oligodeoxyribonucleotides containing tetraguanylate tracts, Nucleic Acids Res., 25:1327-1332 (1997).
Blanco et al., Principles of nanoparticle design for overcoming biological barriers to drug delivery, Nature biotechnology, 33:941-951 (2015).
Blazar et al., Synthetic unmethylated cytosine-phosphate-guanosine oligodeoxynucleotides are potent stimulators of antileukemia responses in naive and bone marrow transplant recipients, Blood, 98:1217-1225 (2001).
Borlinghaus et al., HyVolution—the smart path to confocal super-resolution, Nat. Methods, 13:i-iii (2016).
Bouderault et al., Nanoscale tools to selectively destroy cancer cells, chem. Commun., (18):2118-2120 (2008).
Boutros et al., Safety profiles of anti-CTLA-4 and anti-PD-1 antibodies alone and in combination, Nature Reviews Clinical Oncology, 13:473-486 (2016).
Briley et al., In Nanomaterials for Biomedicine; American Chemical Society, 1119:1-20 (2012).
Brodin et al., DNA-mediated cellular delivery of functional enzymes, J. Am. Chem. Soc., 137(47):14838-14841 (2015).
Brus, Quantum crystallites and nonlinear optics, Appl. Phys. A., 53:465-474 (1991).
Bunge et al., Lipophilic oligonucleotides spontaneously insert into lipid membranes, bind complementary DNA strands, and sequester into lipid-disordered domains, Langmuir, Mar. 17, 2007, vol. 23, No. 8, pp. 4455-4464.
Burgess, Liposome preparation—Avanti(Registered) Polar Lipids, Sigma-Aldrich, 3 pages (1998).
Cagdas et al., Liposomes as potential drug carrier systems for drug delivery, In Application of Nanotechnology in Drug Delivery, Chapter 1, 51 pages (2014).
Calabrese et al., Biocompatible infinite-coordination-polymer nanoparticle-nucleic acid conjugates for antisense gene regulation, Angew. Chem. Int. Ed. Engl., 54(2):476-480 (2015).
Cao et al., Reversible cell-specific drug delivery with aptamer-functionalized liposomes, Angew. Chem. Int. Ed., 48:6494-6498 (2009).
Capaccioli et al., Cationic lipids improve antisense oligonucleotide uptake and prevent degradation in cultured cells and inhuman serum, Biochem. Biophys. Res. Commun., 197(2):818-825 (1993).

Cerritelli et al., PEG-SS-PPS:? Reduction-Sensitive Disulfide Block Copolymer Vesicles for Intracellular Drug Delivery, Biomacromolecules, 8(6):1966-1972 (2007).
Chien et al., DNA-nanoparticle micelles as supramolecular fluorogenic substrates enabling catalytic signal amplification and detection by DNAzyme probes, Chem. Commun., 47:167-169 (2011).
Chinen et al., Relationships between Poly(ethylene glycol) modifications on RNA-spherical nucleic acid conjugates and cellular uptake and circulation time, Bioconjugate Chemistry, 27(11):2715-2721 (2016).
Chinnathambi et al., Binding mode of CpG oligodeoxynucleotides to nanoparticles regulates bifurcated cytokine induction via Toll-like receptor 9, Scientific Reports, 2(534):1-9 (2012).
Cho et al., Targeted delivery of siRNA-generating DNA nanocassettes using multifunctional nanoparticles, Small 9(11): 1964-1973 (2013).
Cho et al., Therapeutic nanoparticles for drug delivery in cancer, Clin. Cancer Res., 14(5)11310-1316 (2008).
Choi et al., Mechanism for the endocytosis of spherical nucleic acid nanoparticle conjugates, Proc. Natl. Acad. Sci. U.S.A., 110(19):7625-7630 (2013).
Clauson et al., The Content of CpG-DNA in Antigen-CpG Conjugate Vaccines Determines Their Cross-Presentation Activity, Bioconjug. Chem., 30(3):561-567 (2019).
Cook, Medicinal chemistry of antisense oligonucleotides—future opportunities, Anti-Cancer Drug Design, 6(6):585-607 (1991).
Coulie et al., Tumour antigens recognized by T lymphocytes: at the core of cancer immunotherapy, Nature Reviews Cancer, 14(2):135-146 (2014).
Couvreur, Nanoparticles in drug delivery: past, present and future, Advanced drug delivery reviews, 65(1):21-23 (2013).
Curtis et al., A morphology-selective copper organosol\, Angew. Chem. Int. Ed. Engl., 27(11):1530-1533 (1988).
Cutler et al., Polyvalent nucleic acid nanostructures, J. Am. chem. Soc., 133(24)19254-9257 (2011).
Cutler et al., Polyvalent oligonucleotide iron oxide nanoparticle "click" conjugates, Nano Lett., 10(4)11477-1480 (2010).
Cutler et al., Spherical nucleic acids, J. Am. Chem. Soc., 134(3):1376-1391 (2012).
Datta et al., The Therapeutic Potential of Antigen-Oligonucleotide Conjugates, Ann. N.Y. Acad. Sci., 1002(1):105-111 (2003).
Dave et al., Programmable assembly of DNA-functionalized liposomes by DNA, ACS Nano, 5(2)11304-1312 (2011).
Dearman et al., Toll-like receptor ligand activation of murine bone marrow-derived dendritic cells, Immunology, 126:475-84 (2009).
Dua et al., Liposomei Methods of Preparation and Applications, International Journal of Pharmaceutical Studies and Research, 3(2)114-20 (2012).
Englisch et al., Chemically modified oligonucleotides as probes and inhibitors, Angew. Chem. Int. Ed., 30(6):613-629 (1991).
Enustun et al., Coagulation of colloidal gold, J. Am. Chem. Soc., 85(21):3317-3328 (1963).
Liu et al., Silica nanoparticle supported lipid bilayers for gene delivery, chem. Commun., 5100-5102 (2009).
Luo et al., A Sting-Activating Nanovaccine for Cancer Immunotherapy, Nat. Nanotechnol., 12(7):648-654 (2017).
Lytton-Jean et al., Highly Cooperative Behavior of Peptide Nucleic Acid Linked DNA Modified Gold Nanoparticle and Combo Polymer Aggregates, Advanced Materials, 21(6):706-709 (2009).
Ma et al., Reductively Responsive Hydrogel Nanoparticles with Uniform Size, Shape, and Tunable Composition for Systemic Sirna Delivery in Vivo, Mol. Pharm., 12(10):3518-3526 (2015).
MacFarlane et al., Nanoparticle Superlattice Engineering with DNA, Science, 334:(6053):204-208 (2011).
Madaan et al., A stepwise procedure for isolation of murine bone marrow and generation of dendritic cells, Journal of Biological Methods, 1:e1 (2014).
Majer et al., Nucleic acid-sensing TLRs: trafficking and regulation, Curr. Opin. Immunol., 44:26-33 (2017).
Mammadov et al., Virus-like nanostructures for tuning immune response, Sci. Rep., 5(16728):1-15 (2015).

(56) References Cited

OTHER PUBLICATIONS

Manders et al., Dynamics of threedimensional replication patterns during the S-phase, analysed by double labelling of DNA and confocal microscopy, J. Cell Sci., 103:857-862 (1992).
Manders et al., Measurement of co-localization of objects in dual-colour confocal images, J. Microsc., 169:375-382 (1993).
Mangsbo et al., Enhanced Tumor Eradication by Combining CTLA-4 or PD-1 Blockage with CpG Therapy, Journal of Immunotherapy, 33(3)1225-235 (2010).
Manson et al., Polyethylene glycol functionalized gold nanoparticles: the influence of capping density on stability in various media, Gold Bulletin, 44(2):99-105 (2011).
Marinakos et al., Gold nanoparticles as templates for the synthesis of hollow nanometer-sized conductive polymer capsules, Adv. Mater., 11(1):34-37 (1999).
Marinakos et al., Template synthesis of one-dimensional Au, Au-poly(pyrrole), and poly(pyrrole) nanoparticle arrays, Chem. Mater., 10(5):1214-19 (1998).
Martin et al., Ein neur Zugang zu 2'-O-alkylribonucleosiden and Eigenschaften deren oligonucleotide, Hely. Chim. Acta., 78:486-504 (1995).
Massart, Preparation of aqueous magnetic liquids in alkaline and acidic media, IEEE Transactions on Magnetics, 17(2):1247-1248 (1981).
Massich et al., Regulating Immune Response Using Polyvalent Nucleic Acid-Gold Nanoparticle Conjugates, Molecular Pharmaceutics, 6(6):1934-1940 (2009).
Matijevic et al., Fine Particles Part II: Formation Mechanisms and Applications, MRS Bulletin, 16-47 (1990).
Maurer et al., CpG-DNA Aided Cross-Presentation of Soluble Antigens by Dendritic Cells, Eur. J. Immunol., 32(8):2356-2364 (2002).
McAllister et al., Polymeric nanogels produced via inverse microemulsion polymerization as potential gene and antisense delivery agents, J. Am. Chem. Soc., 124:15198-15207 (2002).
Meckes et al., Enhancing the Stability and Immunomodulatory Activity of Liposomal Spherical Nucleic Acids through Lipid-Tail DNA Modifications, Small, 14:1702909 (2018).
Mesmaeker et al., Backbone modifications in oligonucleotides and peptide nucleic acid systems, Curr. Opin. In Struct. Biol., 5:343-355 (1995).
Ming et al., Bioconjugates for targeted delivery of therapeutic oligonucleotides, Adv. Drug. Deliv. Rev., 87:81-89 (2015).
Mirkin et al., A DNA-based method for rationally assembling nanoparticles into macroscopic materials, Nature, 382(6592):607-609 (1996).
Mirkin, Structure-Function Relationships in the Development of Immunotherapeutic Agents, 14th US-Japan Symposium on Drug Delivery Systems, Maui, HI (2017).
Mohamed et al., Effect of toll-like receptor 7 and 9 targeted therapy to prevent the development of hepatocellular carcinoma, Liver Int., 35(3):1063-1076 (2015).
Mohamed et al., TLR9 mediates S. aureus killing inside osteoblasts via induction of oxidative stress, BMC Microbiology, 16(article 230):8 (2016).
Mueller et al., Rapid and Persistent Delivery of Antigen by Lymph Node Targeting Print Nanoparticle Vaccine Carrier to Promote Humoral Immunity, Mol. Pharm., 12(5):1356-1365 (2015).
Murad et al., CPG-7909 (PF-3512676, ProMune®): toll-like receptor-9 agonist in cancer therapy, Expert Opinion on Biological Therapy, 7(8):1257-1266 (2007).
Muranski et al., Adoptive immunotherapy of cancer using CD4+T cells, Current Opinion in Immunology, 21(2):200-208 (2009).
Nagase, Substrate specificity of MMPs. In matrix metalloproteinase inhibitors in cancer therapy, Springer: 39-66 (2001).
Naidoo et al., Toxicities of the anti-PD-1 and anti-PD-L1 immune checkpoint antibodies, Annals of Oncology, 26(12):2375-2391 (2015).
Nam et al., Bio-bar-code-based DNA detection with PCR-like sensitivity, J. Am. Chem. Soc., 126:5932-5933 (2004).
Nembrini et al., Nanoparticle Conjugation of Antigen Enhances Cytotoxic TCell Responses in Pulmonary Vaccination, Proc. Natl. Acad. Sci., 108(44):E989-E997 (2011).
Nguyen et al., Enzyme-responsive nanoparticles for targeted accumulation and prolonged retention in heart tissue after myocardial infarction, Advanced Materials, 27(37):5547-5552 (2015).
Nielsen et al., Sequence-selective recognition of DNA by strand displacement with a thymine-substituted polyamide, Science, 254:1497-500 (1991).
Nikolov et al., Bias-dependent admittance in hybrid bilayer membranes, Langmuir, 22(17):7156-7158 (2006).
Olshavsky et al., Organometallic synthesis of gallium-arsenide crystallites, exhibiting quantum confinement, J. Am. Chem. Soc., 112(25):9438-9439 (1990).
Olson et al., Activatable cell penetrating peptides linked to nanoparticles as dual probes for in vivo fluorescence and MR imaging of proteases, Proceedings of the National Academy of Sciences, 107(9):4311-4316 (2010).
Otsuka et al., PEGylated nanoparticles for biological and pharmaceutical applications, Adv. Drug Delivery. Rev., 64:246-255 (2012).
Ozpolat et al., Nanomedicine based approaches for the delivery of siRNA in cancer, J. Intern. Med., 267(1):44-53 (2010).
Park et al., DNA-programmable nanoparticle crystallization, Nature, 451:553-556 (2008).
Patel et al., Scavenger receptors mediate cellular uptake of polyvalent oligonucleotide-functionalized gold nanoparticles, Bioconjugate Chem., 21(12):2250-2256 (2010).
Patnaik et al., Phase 1 study of pembrolizumab (pembro; MK-3475) plus ipilimumab (IPI) as second-line therapy for advanced non-small cell lung cancer (NSCLC): Keynote-021 cohort D, Journal of Clinical Oncology 33(15):8011-8011 (2015).
Peter et al., Characterization of suppressive oligodeoxynucleotides that inhibit Toll-like receptor-9-mediated activation of innate immunity, Immunology, 123(1):118-128 (2008).
Pfeiffer et al., Bivalent Cholesterol-Based Coupling of Oligonucleotides to Lipid Membrane Assemblies, J. Am. Chem. Soc., 126:10224-10225 (2004).
Pfeiffer et al., Quantification of oligonucleotide modifications of small unilamellar lipid vesicles, Anal. Chem., 78:7493-7498 (2006).
Prigodich et al., Multiplexed nanoflares: mRNA detection in live cells, Anal. Chem., 84:2062-6 (2012).
Prigodich et al., Nano-flares for mRNA regulation and detection, ACS Nano, 3(8):2147-2152 (2009).
Prigodich et al., Tailoring DNA structure to increase target hybridization kinetics on surfaces, J. Am. Chem. Soc., 132:10638-41 (2010).
Wilson et al., pH-Responsive Nanoparticle Vaccines for Dual-Delivery of Antigens and Immunostimulatory Oligonucleotides, ACS Nano, 7(5):3912-3925 (2013).
Wu et al., DNA aptamer-micelle as an efficient detection/delivery vehicle toward cancer cells, Proc. Natl. Acad. Sci. SA., 107(1):5-10 (2010).
Xing et al., Selective delivery of an anticancer drug with aptamer-functionalized liposomes to breast cancer cells in vitro and in vivo, J. Mater. Chem. B., 1:5288-5297 (2013).
Xu et al., Asymmetric functionalization of gold nanoparticles with oligonucleotides, J. Am. Chem. Soc., 128:9286-9287.
Xu et al., Rendering Protein-Based Particles Transiently Insoluble for Therapeutic Applications, J. Am. Chem. Soc., 134(21):8774-8777 (2012).
Yamane et al., On the complexing of desoxyribonucleic acid (DNA) by mercuric ion1, J. Am. Chem. Soc., 83(12):2599-2607 (1961).
Yamankurt et al., Exploration of the nanomedicine-design space with high-throughput screening and machine learning, Nat. Biomed. Eng., 3(4):318-327 (2019).
Yin et al., Supramolecular self-assembled nanoparticles mediate oral delivery of therapeutic TNF-? siRNA against systemic inflammation, Anaew. Chem. Int. Ed. Enal., 125(22):5757-5761 (2013).
Young et al., Hollow spherical nucleic acids for intracellular gene regulation based upon biocompatible silica shells, Nano Lett., 12(7):3867-3871 (2012).

(56) References Cited

OTHER PUBLICATIONS

Zent et al., Phase I clinical trial of CpG oligonucleotide 7909 (PF-03512676) in patients with previously treated chronic lymphocytic leukemia, Leukemia & Lymphoma, 53(2):211-217 (2012).
Zhang et al., A general approach to DNA-programmable atom equivalents, Nat. Mater., 12(8)741-746 (2013).
Zhang et al., An extremely stable and orthogonal DNA base pair with a simplified three-carbon backbone, J. Am. Chem. Soc., 127(1):74-75 (2005).
Zhang et al., Antibody-linked spherical nucleic acids for cellular targeting, J. Am. Chem. Soc., 134:16488-91 (2012).
Zhang et al., Informational Liposomes: Complexes Derived from Cholesteryl-conjugated Oligonucleotides and Liposomes, Tetrahedron Letters, 37(35):6243-6246 (1996).
Zhang et al., PowerBLAST: a new network BLAST application for interactive or automated sequence analysis and annotation, Genome Res., 7(6):649-656 (1997).
Zhang et al., Structure-activity relationships of cationic shell-crosslinked knedel-like nanoparticles: shell composition and transfection efficiency/cytotoxicity, Biomaterials, 31:1805-1813 (2010).
Zheng et al., A spherical nucleic acid platform based on self-assembled DNA biopolymer for high-performance cancer therapy, ACS Nano, 7(8):6545-6554 (2013).
Zheng et al., Aptamer nano-flares for molecular detection in living cells, Nano Lett., 9(9):3258-3261 (2009).
Zheng et al., Topical delivery of siRNA-based spherical nucleic acid nanoparticle conjugates for gene regulation, Proceedings of the National Academy of Sciences, 109(30):11975-11980 (2012).
Zhu et al., Matrix metalloprotease 2-responsive multifunctional liposomal nanocarrier for enhanced tumor targeting, ACS Nano., 6(4):3491-3498 (2012).
Zimmermann et al., A novel silver(i)-mediated DNA base pair, J. Am. Chem. Soc., 124(46):13684-13685 (2002).
Radovic-Moreno et al., Immunomodulatory Spherical Nucleic Acids, Proc. Natl. Acad. Sci. U.S.A., 112(13):3892-3897 (2015).
Ries et al., Efficient liposome fusion mediated by lipid-nucleic acid conjugates, Org. Biomol. Chem., 15(42):8936-8945 (2017).
Rincon-Restrepo et al., Vaccine nanocarriers: Coupling intracellular pathways and cellular biodistribution to control CD4 vs CD8 T cell responses, Biomaterials, 132:48-58 (2017).
Rosi et al., Nanostructures in biodiagnostics, Chem. Rev., 105(4):1547-1562 (2005).
Rosi et al., Oligonucleotide-modified gold nanoparticles for intracellular gene regulation, Science, 312(5776):1027-1030 (2006).
Rostovtsev et al., A stepwise huisgen cycloaddition process: copper(I)-catalyzed regioselective "Ligation" of azides and terminal alkynest, Angewandte chemie, 114(14): 2708-2711 (2002).
Sambrook et al., Molecular Cloning: A Laboratory Manual, 2nd Edition, Cold Spring Harbor, New York (1989).
Sanghvi et al., Antisense research and applications, CRC Press, Boca Raton, 276-278 (1993).
Sanghvi, Chapter 15, Antisense research and applications, Crooke, S. T. and Lebleu, B., ed., CRC Press, 289-302 (1993).
Schwartz, A cell culture model forT lymphocyte clonal anergy, Science, 248:1349-1356 (1990).
Seferos et al., Locked nucleic acid-nanoparticle conjugates, ChemBioChem, 8:1230-1232 (2007).
Seferos et al., Nano-flares: probes for transfection and mRNA detection in living cells, J. Am. Chem. Soc., 129(50):15477-15479 (2007).
Seferos et al., Polyvalent DNA nanoparticle conjugates stabilize nucleic acids, Nano Lett., 9(1 ):308-311 (2009).
Senior et al., Stability of small unilamellar liposomes in serum and clearance from the circulation: the effect of the phospholipid and cholesterol components, Life Sci., 30:2123-2136 (1982).
Siutter et al., Conjugation of Ovalbumin to Trimethyl Chitosan Improves Immunogenicity of the Antigen, J. Control. Release, 143(2):207-214 (2010).
Skakuj et al., Conjugation Chemistry-Dependent T-Cell Activation with Spherical Nucleic Acids, Journal of the American Chemical Society, 140(4):1227-1230 (2018).
Slack et al., Rotaxane probes for protease detection by 129 Xe hyperCEST NMR, chemical communications, 53(6):1076-1079 (2017).
Sokolova et al., The use of calcium phosphate nanoparticles encapsulating Toll-like receptor ligands and the antigen hemagglutinin to induce dendritic cell maturation and T cell activation, Biomaterials, 31:5627-5633 (2010).
Sprangers et al., Liposomal spherical nucleic acids for regulating long noncoding RNAs in the nucleus, Small, 13(10):10.1002/smll.201602753 (2016).
Staben et al., Targeted Drug Delivery through the Traceless Release of Tertiary and Heteroaryl Amines from Antibody-Drug Conjugates, Nat. Chem., 8:1112-1119 (2016).
Stengel et al., Determinants for Membrane Fusion Induced by Cholesterol-Modified DNA Zippers, J. Phys. Chem. B., 112:8264-74 (2008).
Stengel et al., DNA-Induced Programmable Fusion of Phospholipid Vesicles, J. Am. Chem. Soc., 129:9584-5 (2007).
Sulkowski et al., The influence of temperature, cholesterol content and pH on liposome stability, J. Mol. Struct., 744-747:737-747 (2005).
Suma et al., Modulated Fragmentation of Proapoptotic Peptide Nanoparticles Regulates Cytotoxicity, J. Am. Chem. Soc., 139(11):4009-4018 (2017).
Swain et al., Expanding roles for CD4+ T cells in immunity to viruses, Nature Reviews Immunology, 12:136-148 (2012).
Switaj et al., CpG Immunostimulatory Oligodeoxynucleotide 1826 Enhances Antitumor Effect of Interleukin 12 Gene-Modified Tumor Vaccine in a Melanoma Model in Mice, Clinical Cancer Research, 10:4165-4175 (2004).
Tan et al., Blurring the Role of Oligonucleotides: Spherical Nucleic Acids as a Drug Delivery Vehicle, J. Am. Chem. Soc., 138(34):10834-10837 (2016).
Thomas, The Interaction of HgCl2 with sodium thymonucleate, J. Am. Chem. Soc., 76(23):6032-6034 (1954).
Tincer et al., Immunostimulatory activity of polysccharidepoly (I:C) nanoparticles, Biomaterial., 32(18):4275-4282 (2011).
Titta et al., Nanoparticle Conjugation of CpG Enhances Adjuvancy for Cellular Immunity and Memory Recall at Low Dose, Proc. Natl. Acad. Sci., 110(49):19902-19907 (2013).
Tiwari et al., Drug delivery systems: An updated review, International journal of pharmaceutical investigation, 2(1):2-11 (2012).
Tondelli et al., Highly efficient cellular uptake of c-myb antisense oligonucleotides through specifically designed polymeric nanospheres, Nucl. Acids Res., 26(23):5425-5431 (1998).
Tzeng et al., Temporally programmed CD8a+ DC activation enhances combination cancer immunotherapy, Cell reports, 17(10):2503-2511 (2016).
Uchida et al., Gallium arsenide nanocrystals prepared in quinoline, J. Phys. Chem., 95:5382 (1992).
Van Der Vlies et al., Synthesis of Pyridyl Disulfide-Functionalized Nanoparticles for Conjugating Thiol-Containing Small Molecules, Peptides, and Proteins, Bioconjug. Chem., 21(4):653-662 (2010).
Veiseh et al., Optical and MRI multifunctional nanoprobe for targeting gliomas, Nano Lett., 5(6):1003-1008 (2005).
Versluis et al., In situ modification of plain liposomes with lipidated coiled coil forming peptides induces membrane fusion, J. Am. Chem. Soc., 135:8057-8062 (2013).
Verthelyi et al., CpG-ODN—Safety Considerations, Microbial DNA and Host Immunity, 385-396 (2002).
Vollmer et al., Characterization of three CpG oligodeoxynucleotide classes with distinct immunostimulatory activities, Eur. J. Immunol., 34:251-62 (2004).
Wang et al., Altering DNA-Programmable Colloidal Crystallization Paths by Modulating Particle Repulsion, Nano Letters, 17:5126-32 (2017).
Wang et al., Nanometer-sized semiconductor clusters: materials synthesis, quantum size effects, and photophysical properties, J. Phys. Chem., 95:525-532 (1991).
Wang et al., Rational vaccinology with spherical nucleic acids, PNAS., 10473-481 (2019).

(56) References Cited

OTHER PUBLICATIONS

Weber et al., Nivolumab versus chemotherapy in patients with advanced melanoma who progressed after anti-CTLA-4 treatment (CheckMate 037): a randomised, controlled, open-label, phase 3 trial, The Lancet Oncology, 16:375-384 (2015).
Weeranta et al., CpG DNA induces stronger immune responses with less toxicity than other adjuvants, Vaccine, 18(17):1755-1762 (2000).
Wei et al., Polyvalent Immunostimulatory Nanoagents with Self-Assembled CpG Oligonucleotide-Conjugated Gold Nanoparticles, Angewandte Chemie International Edition, 51(5):1202-1206 (2012).
Weller, Colloidal semiconductor Q-particles: Chemistry in the transition region between solid state and molecules, Angew. Chem. Int. Ed. Engl., 32(1):41-53 (1993).
Welters et al., Induction of Tumor-Specific CD4+ and CD8+ T-Cell Immunity in Cervical Cancer Patients by a Human Papillomavirus Type 16 E6 and E7 Long Peptides Vaccine, Clin. Cancer Res., 14(1):178-187 (2008).
West et al., Recognition and signaling by toll-like receptors, Annu. Rev. Cell Dev. Biol., 22:409-37 (2006).
Whitehead et al., Knocking down barriers: advances in siRNA delivery, Nat. Rev. Drug. Discov., 8:129-138 (2009).
Willis et al., Liposome-Anchored Vascular Endothelial Growth Factor Aptamers, Bioconjugate Chem. 9 573-582 (1998).
June et al., The B7 and CD28 receptor families, Immunol. Today, 15:321-331 (1994).
Kandimalla et al., Secondary structures in CpG oligonucleotides affect immunostimulatory activity, Biochemical and Biophysical Research Communications, 306:948-953 (2003).
Kapadia et al., Reduction Sensitive PEG Hydrogels for Codelivery of Antigen and Adjuvant to Induce Potent CTLs, Mol. Pharm., 13(10):3381-3394 (2016).
Kapadia et al., Spherical Nucleic Acid Nanoparticles: Therapeutic Potential, BioDrugs, 32:297-309 (2018).
Kasuya et al., Bio-nanocapsule-liposome conjugates for in vivo pinpoint drug and gene delivery, Methods Enzymol., 464:147-166 (2009).
Katz, The Reversible Reaction of Sodium Thymonucleate and Mercuric Chloride, J. Am. Chem. Soc., 74(9):2238-2245 (1952).
Kelly et al., Targeted liposomal drug delivery to monocytes and macrophages, Journal of Drug Delivery, Article ID 727241:1-11 (2011).
Kelty et al., High-throughput synthesis and characterization of nanocrystalline porphyrinic zirconium metal-organic frameworks, Chem. Commun(Camb), 52(50):7854-7857 (2016).
Kemp et al., "Combo" nanomedicine: Co-delivery of multi-modal therapeutics for efficient, targeted, and safe cancer therapy, Advanced Drug Delivery Reviews, 98:3-18 (2016).
Kennedy et al., Multiple roles for CD4 T cells in anti-tumor immune responses, Immunological Reviews, 222(1):129-144 (2008).
Kerkmann et al., Spontaneous Formation of Nucleic Acid-based Nanoparticles Is Responsible for High Interferon-a Induction by CpG-A in Plasmacytoid Dendritic Cells, J. Biol. Chem., 280:8086-8093 (2005).
Khalil et al., The future of cancer treatment: immunomodulation, CARs and combination immunotherapy, Nature reviews Clinical oncology, 13:273-290 (2016).
Kim et al., Cationic solid lipid nanoparticles reconstituted from low density lipoprotein components for delivery of SiRNA, Mol. Pharm., 5(4):622-631 (2008).
Kim et al., Effect of bovine serum albumin on the stability of methotrexate-encapsulated liposomes, Arch. Pharmacal Res., 14:336-341 (1991).
Kim et al., Transmutable nanoparticles with reconfigurable surface ligands, Science, 351:579-582 (2016).
Klebanoff et al., CD8+ T-cell memory in tumor immunology and immunotherapy, Immunological Reviews, 211(1):214-224 (2006).
Klinman, Immunotherapeutic uses of CpG oligodeoxynucleotides, Nat. Rev. Immunol., 4:249-259 (2004).
Koshy et al., Biomaterials for enhancing anti-cancer immunity, Current opinion in biotechnology, 40:1-8 (2016).
Kosturko et al., The crystal and molecular structure of a 2:1 complex of 1-methylthymine-mercury (II), Biochemistry, 13(19):3949-3952 (1974).
Kramer et al., Comparative Study of 5'- and 3'-Linked CpGAntigen Conjugates for the Induction of Cellular Immune Responses, ACS Omega, 2(1):227-235 (2017).
Kramer et al., Intracellular Cleavable CpG Oligodeoxynucleotide-Antigen Conjugate Enhances Anti-Tumor Immunity, Mol. Ther., 25(1):62-70 (2017).
Kreig, Toll-like receptor 9 (TLR9) agonists in the treatment of cancer, Oncogene, 27:116-167 (2008).
Kreutz et al., Antibody-Antigen-Adjuvant Conjugates Enable Co-Delivery of Antigen and Adjuvant to Dendritic Cells in Cis but Only Have Partial Targeting Specificity, PLoS One, 7(7):e40208 (2012).
Krieg, Development of TLR9 agonists for cancer therapy, J. Clin. Invest., 117(5):1184-1194 (2007).
Krieg, Therapeutic potential of Toll-like receptor 9 activation, Nat. Rev. Drug Discov., 5:471-484 (2006).
Kroschwitz, Concise Encyclopedia of Polymer Science and Engineering, John Wiley & Sons, 858-859 (1990).
Kukowska-Latallo et al., Efficient transfer of genetic material into mammalian cells using Starburst polyamidoamine dendrimers, Proc. Natl. Acad. Sci. USA, 93(10):4897-4902 (1996).
Kulkarni et al., Mmp-9 responsive PEG cleavable nanovesicles for efficient delivery of chemotherapeutics to pancreatic cancer, Molecular Pharmaceutics, 11(7):2390-2399 (2014).
Lancaster et al., The physiological regulation of toll-like receptor expression and function in humans, J. Physiol., 563:945-955 (2005).
Laouini et al., Preparation, characterization and applications of liposomes: state of the art, Journal of colloid science and biotechnology, 1:148-168 (2012).
Laramy et al., ACS Nano, 13(2):1412 (2019).
Lee et al., Imageable Antigen-Presenting Gold Nanoparticle Vaccines for Effective Cancer Immunotherapy In vivo, Angewandte Chemie International Edition, 51(35):8800-8805 (2012).
Lee et al., Induction of Potent Antigen-specific Cytotoxic T Cell Response by PLGA-nanoparticles Containing Antigen and TLR Agonist, Immunel. Netw., 13(1):30-33 (2013).
Lee et al., Silver nanoparticle-oligonucleotide conjugates based on DNA with triple cyclic disulfide moieties, Nano Lett., 7(7):2112-2115 (2007).
Lee et al., Trafficking of endosomal Toll-like receptors, Trends Cell Biol., 24(6):360-369 (2014).
Lesieur et al., Size analysis and stability study of lipid vesicles by high-performance gel exclusion chromatography, turbidity, and dynamic light scattering, Analytical Biochemistry, 192(2):334-343 (1991).
Li et al., Combination Delivery of Antigens and CpG by Lanthanides-Based Core-Shell Nanoparticles for Enhanced Immune Response and Dual-Mode Imaging, Advanced Healthcare Materials, 2(10):1309-1313 (2013).
Li et al., Materials based tumor immunotherapy vaccines, Current Opinion in Immunology, 25(2):238-245 (2013).
Li et al., Molecular spherical nucleic acids, PNAS, 115(17):4340-4344 (2018).
Li et al., Nucleolin-targeting liposomes guided by aptamer AS1411 for the delivery of siRNA for the treatment of malignant melanomas, Biomaterials, 35(12):3840-3850 (2014).
Li et al., Polymer- and lipid-based nanoparticle therapeutics for the treatment of liver diseases, Nano Today 5(4):296-312 (2010).
Li et al., Reversible and Chemically Programmable Micelle Assembly with DNA Block-Copolymer Amphiphiles, Nano Lett., 4(6):1055-1058 (2004).
Li et al., Smart asymmetric vesicles with triggered availability of inner cell-penetrating shells for specific intracellular drug delivery, ACS Appl. Mater. Interfaces, 9(21):17727-17735 (2017).
Li et al., Synthesis of nanocrystals of Zr-based metal-organic frameworks with csq-net: significant enhancement in the degradation of a nerve agent simulant, Chem. Commun., 51(54):10925-10928 (2015).
Li et al., Thermal stability of DNA functionalized gold nanoparticles, Bioconjugate chem., 24:1790-1797 (2013).

(56) References Cited

OTHER PUBLICATIONS

Lin et al., Gold Nanoparticle Delivery of Modified CpG Stimulates Macrophases and Inhibits Tumor Growth for Enhanced Immunotherapy, PLOS ONE, 8(5):e63550 (2013).
Liu et al., DNA-based micelles: synthesis, micellar properties and size-dependent cell permeability, Chemistry, 16:3791-3797 (2010).
Liu et al., Freezing directed construction of Bio/Nano interfaces: reagentless conjugation, Denser spherical nucleic acids, and better nanoflares, J. Am. Chem. Soc., 139(28): 9471-9474 (2017).
Liu et al., Membrane anchored immunostimulatory oligonucleotides for in vivo cell modification and localized immunotherapy, Angew. Chem. Int. Ed. Engl., 50(31):7052-7055 (2011).
Liu et al., New poly(d-glucaramidoamine)s induce DNA nanoparticle formation and efficient gene delivery into mammalian cells, J. Am. Chem. Soc., 126(24):7422-7423 (2004).
Akinc et al., A combinatorial library of lipid-like materials for delivery of RNAi therapeutics, Nat. Biotechnol., 26(5):561-569 (2008).
Akinc et al., Targeted delivery of RNAi therapeutics with endogenous and exogenous ligand-based mechanisms, Molecular therapy: the journal nfthe American Society of Gene Therapy, 18(7):1357-1364 (2010).
Alfagih et al., Nanoparticles as adjuvants and nanodelivery systems for mRNA-based vaccines, Pharmaceutics, 13:45 (2021).
Cheng et al., Dendrimer-Based Lipid Nanoparticles Deliver Therapeutic FAH mRNA to Normalize Liver Function and Extend Survival in a Mouse Model of Hepatorenal Tyrosinemia Type I, Advanced Materials, 30(52):e1805308 (2018).
Cheng et al., Selective organ targeting (SORT) nanoparticles for tissue-specific mRNA delivery and CRISPR-Cas gene editing, Nature Nanotechnology, 15:313-320 (2020).
Chinen et al., Spherical Nucleic Acid Nanoparticle Conjugates Enhance G-Quadruplex Formation and Increase Serum Protein Interactions, Angew. Chemie—Int. Ed., 54(2):527-531 (2015).
English Translation of CN 101850117 A "A Compound Immunologic Adjuvant and Vaccine." Originally Published in Chinese on Oct. 6, 2010, 6 printed pages. (Year: 2010).
Ferrer et al., Structure-Dependent Biodistribution of Liposomal Spherical Nucleic Acids, ACS. Nano., 14(2):1682-1693 (2020).
Guan, Chenxia M., Alyssa B. Chinen and Jennifer R. Ferrer, Caroline H. Ko, and Chad A. Mirkin. "Impact of sequence specificity of spherical nucleic acids on macrophage activation in vitro and in vivo." Molecular pharmaceutics 16, No. 10 (2019): 4223-4229.
Hajj et al., Tools for Translation: Non-Viral Materials for Therapeutic MRNA Delivery. Nature Reviews Materials, 2:17056 (2017).
Hayes, Oliver G., Janet R. McMillan, Byeongdu Lee, and Chad A. Mirkin. "DNA-encoded protein Janus nanoparticles." Journal of the American Chemical Society 140, No. 29 (2018): 9269-9274.
International Application No. PCT/US2022/012023, International Preliminary Report on Patentability, mailed Jul. 27, 2023.
International Application No. PCT/US2022/012023, International Search Report and Written Opinion, mailed Mar. 29, 2022.
Jayaraman et al., Maximizing the Potency of SiRNA Lipid Nanoparticles for Hepatic Gene Silencing in Vivo, Angew. Chemie—Int. Ed., 51(34):8529-8533 (2012).
Liang et al., Aptamer-functionalized lipid nanoparticles targeting osteoblasts as a novel RNA interference-based bone anabolic strategy, Nat. Med., 21(3): 288-294 (2015).
Lokugamage et al., Constrained nanoparticles deliver siRNA and sgRNA to T cells in vivo without targeting ligands, Advanced Materials, 31(41):e1902251 (2019).
Love et al., Lipid-like Materials for Low-Dose, in Vivo Gene Silencing, Proc. Natl. Acad. Sci., 107(5):1864-1869 (2010).
Maier et al., Biodegradable Lipids Enabling Rapidly Eliminated Lipid Nanoparticles for Systemic Delivery of RNAi Therapeutics, Mol. Ther., 21(8):1570-1578 (2013).
Patel et al., Naturally-occurring cholesterol analogues in lipid nanoparticles induce polymorphic shape and enhance intracellular delivery of mRNA, Nat. Comm., 11:983 (2020).
Paunovska et al., A Direct Comparison of in Vitro and in Vivo Nucleic Acid Delivery Mediated by Hundreds of Nanoparticles Reveals a Weak Correlation, Nano Lett., 18(3):2148-2157 (2018).
Robson et al., Advantages and Limitations of Current Imaging Techniques for Characterizing Liposome Morphology, Frontiers in Pharmacology, 9:Article 80 (2018).
Sago et al., Nanoparticles That Deliver RNA to Bone Marrow Identified by in Vivo Directed Evolution, J. Am. Chem. Soc., 140(49):17095-17105 (2018).
Sahin et al., MRNA-Based Therapeutics—Developing a New Class of Drugs, Nature Reviews Drug Discovery, 13:759-780 (2014).
Semple et al., Rational Design of Cationic Lipids for SiRNA Delivery, Nat. Biotechnol., 28(2):172-176 (2010).
Veiga et al., Targeted lipid nanoparticles for RNA therapeutics and immunomodulation in leukocytes, Advanced Drug Delivery Reviews, 159:364-376 (2020).
Wang et al (Matrix metalloproteinase 2-responsive micelle for siRNA delivery. Biomaterials 35 (2014) 7622-7634) and Fahmy et al (US 2015/0064265). (Year: 2014).
Wang et al., Delivery of oligonucleotides with lipid nanoparticles, Adv. Drug Deliv. Rev., 87:68-80 (2015).
Wang et al., The Functional Effects of Physical Interactions among Toll-like Receptors 7, 8, and 9, The Journal of Biological Chemistry, 281(49): 37427-37434 (2006).

* cited by examiner (to be continued)

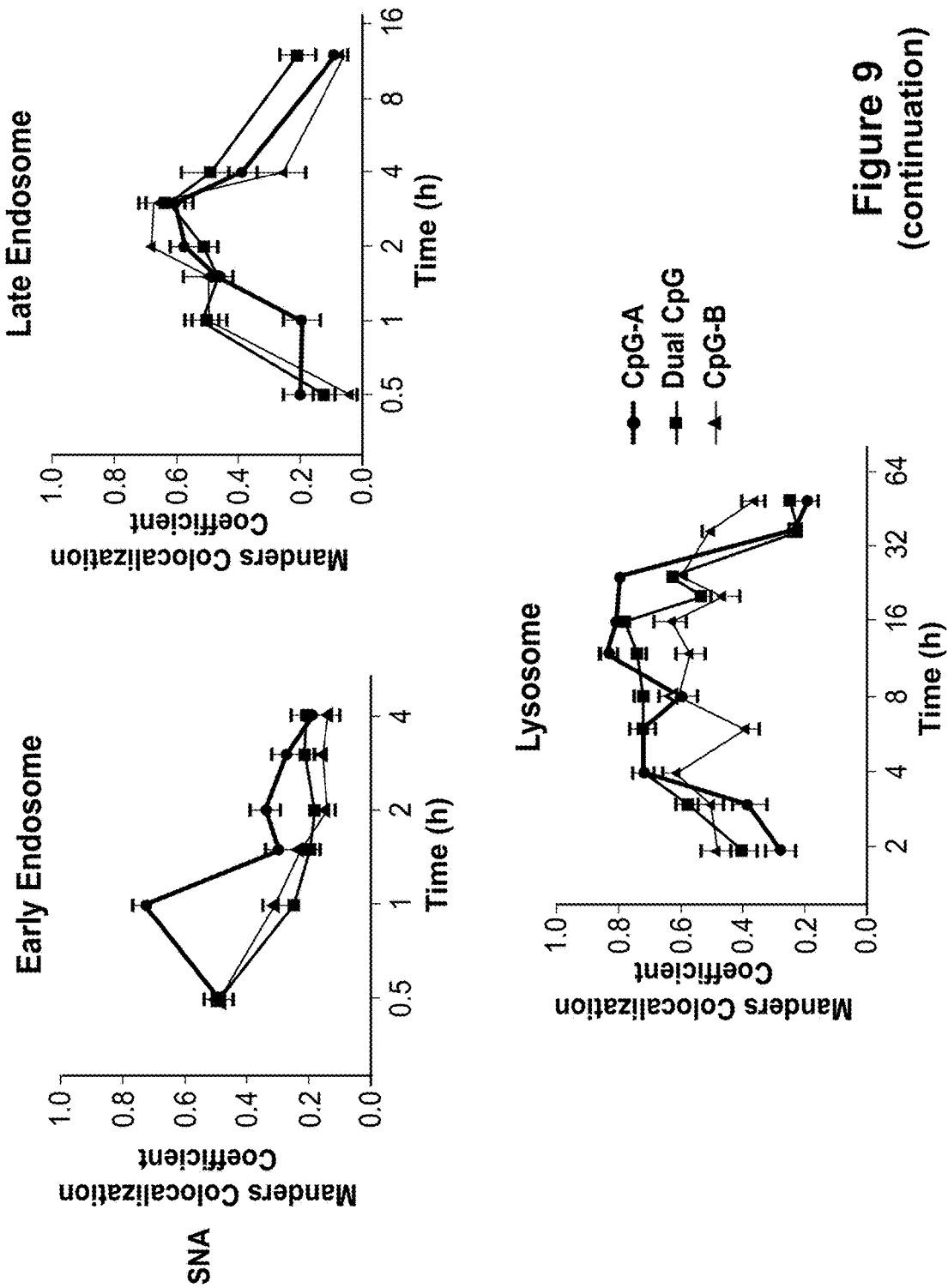
Figure 9 (continuation)

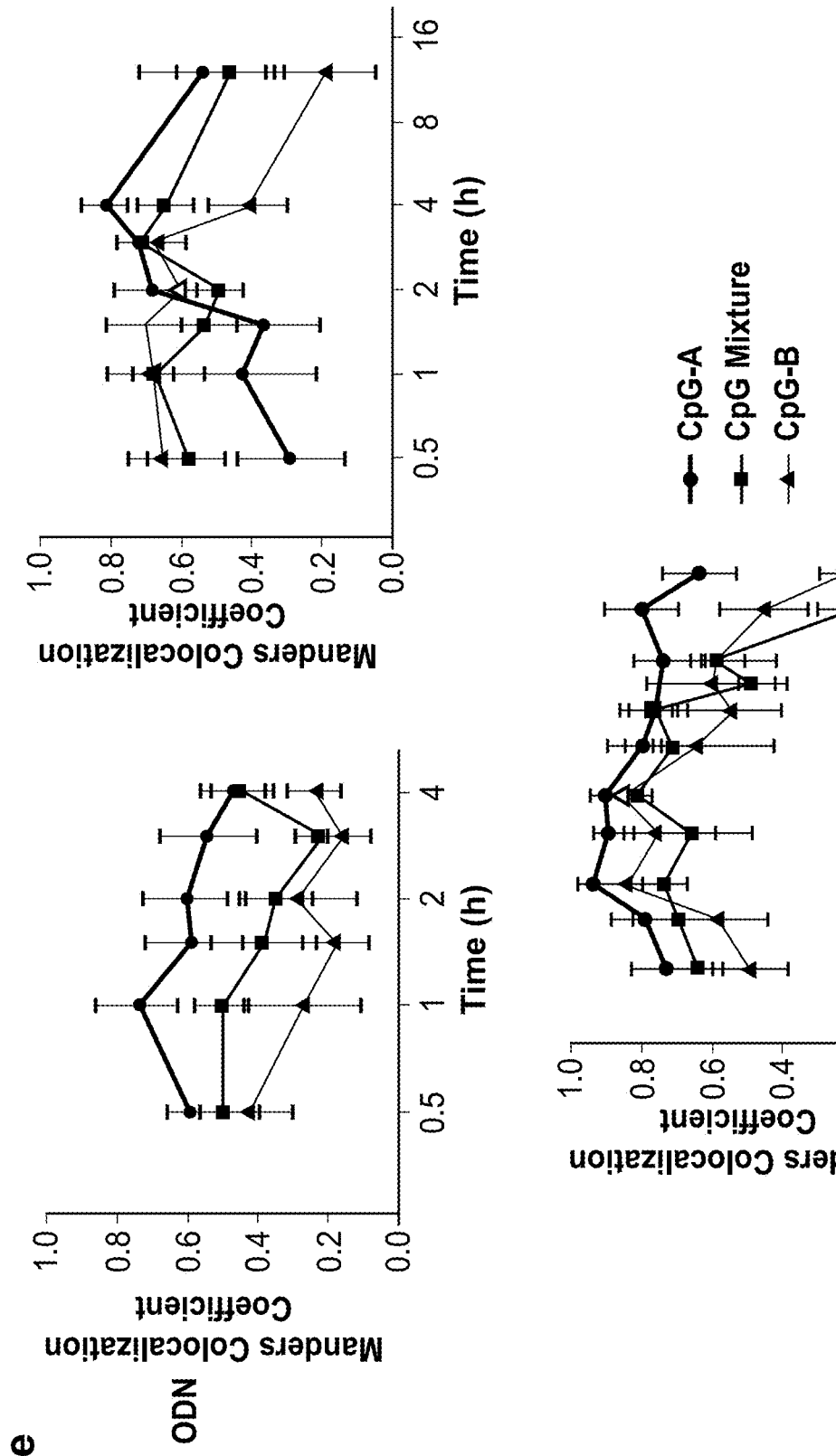
Figure 9 (continuation)

SEQUENCE LISTING

<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 1
tcaacgttga                                                           10

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (Sp18)2-chol

<400> SEQUENCE: 2
ggggtcaacg ttgaggggggg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (Sp18)2-chol

<400> SEQUENCE: 3
tccatgacgt tcctgacgtt                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
ggggtcaacg ttgaggggggg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
tccatgacgt tcctgacgtt                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature

```
<222> LOCATION: (20)..(20)
<223> OTHER INFORMATION: (Sp18)-FAM-(Sp18)-chol

<400> SEQUENCE: 6
ggggtcaacg ttgaggggg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (Sp18)-Cy3-(Sp18)-chol

<400> SEQUENCE: 7
tccatgacgt tcctgacgtt                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (Sp18)-Cy5-(Sp18)-chol

<400> SEQUENCE: 8
tccatgacgt tcctgacgtt                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: FAM

<400> SEQUENCE: 9
ggggtcaacg ttgaggggg                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: Cy5

<400> SEQUENCE: 10
tccatgacgt tcctgacgtt                                                  20

<210> SEQ ID NO 11
<211> LENGTH: 20
<212> TYPE: DNA
<213> ORGANISM: Homo Sapiens

<400> SEQUENCE: 11
```

```
gggggacgat cgtcgggggg                                              20

<210> SEQ ID NO 12
<211> LENGTH: 24
<212> TYPE: DNA
<213> ORGANISM: Homo Sapiens

<400> SEQUENCE: 12
tcgtcgtttt gtcgttttgt cgtt                                         24
```

SEQUENCE MULTIPLICITY WITHIN SPHERICAL NUCLEIC ACIDS

CROSS-REFERENCE TO RELATED APPLICATIONS

This application claims the priority benefit under 35 U.S.C. § 119(e) of U.S. Provisional Patent Application No. 62/927,456, filed Oct. 29, 2019, which is incorporated herein by reference in its entirety.

STATEMENT OF GOVERNMENT INTEREST

This invention was made with government support under grant numbers U54CA199091-01 and R01CA208783-01 awarded by the National Institutes of Health. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "2019-195_Seqlisting.txt", which was created on Oct. 29, 2020 and is 3,023 bytes in size. The subject matter of the Sequence Listing is incorporated herein in its entirety by reference.

BACKGROUND

Spherical nucleic acids (SNAs) are a class of nanostructures consisting of a nanoparticle core surrounded by a shell of highly oriented and densely packed oligonucleotides.[1-2] Such structures are typically more stable than comparable linear strands in biological milieu and exhibit high cellular internalization via scavenger receptor-mediated endocytosis.[3] SNAs made with liposome cores, termed liposomal SNAs (LSNAs), are biocompatible and suitable for a wide variety of biomedical applications.[4-9] To date, with the exception of the use of secondary strands as diluents,[10] material-directing units,[11-12] or probe entities,[13-15] SNAs have been prepared exclusively from a single oligonucleotide sequence.

SUMMARY

Delivering multiple oligonucleotide sequences (e.g., DNA, RNA, etc.) to the same target cell is beneficial in many applications, but direct delivery cannot ensure co-delivery. It is shown herein that multiple oligonucleotide sequences on one spherical nucleic acid (SNA), which is a nanostructure comprising a nanoparticle core surrounded by a shell of highly oriented and densely packed oligonucleotides, enabled efficient co-delivery of several distinct oligonucleotide sequences to the same cell at the pre-determined desired ratios of these sequences.

Thus, the present disclosure is generally directed to spherical nucleic acids (SNAs) comprising a nanoparticle core and an oligonucleotide shell attached to the external surface of the nanoparticle core, wherein the oligonucleotide shell comprises a mixture of oligonucleotides.

Applications of the technology disclosed herein include, but are not limited to: nucleic acid-based therapy, combination therapy, and cancer immunotherapy. Advantages of the technology disclosed herein include, but are not limited to: co-delivery of multiple oligonucleotide sequences to the same cell at controlled ratios for enhanced/synergistic responses; physically (e.g., structural features) and chemically (e.g., backbone chemistry) distinct oligonucleotide sequences.

Accordingly, in some aspects the disclosure provides a spherical nucleic acid (SNA) comprising a nanoparticle core and an oligonucleotide shell attached to the external surface of the nanoparticle core, wherein the oligonucleotide shell comprises a mixture of class A CpG oligonucleotides and class B CpG oligonucleotides, wherein the SNA does not comprise a class C CpG oligonucleotide. In some aspects, the disclosure provides a spherical nucleic acid (SNA) comprising a nanoparticle core and an oligonucleotide shell attached to the external surface of the nanoparticle core, wherein the oligonucleotide shell consists of a mixture of class A CpG oligonucleotides and class B CpG oligonucleotides. In further aspects, the disclosure provides a spherical nucleic acid (SNA) comprising a nanoparticle core and an oligonucleotide shell attached to the external surface of the nanoparticle core, wherein the oligonucleotide shell comprises a mixture of class A CpG oligonucleotides and class B CpG oligonucleotides, wherein the ratio of class A CpG oligonucleotides to class B CpG oligonucleotides in the mixture is about 4:1 to about 1:1. In some embodiments, the class A CpG oligonucleotides each comprise (i) an internal palindrome sequence containing a CpG motif and (ii) an at least partially phosphorothioated poly(G) sequence at its 5' and/or 3' ends. In some embodiments, the class A CpG oligonucleotide is DNA. In further embodiments, the class B CpG oligonucleotides each comprise a fully phosphorothioated sequence comprising one or more CpG motifs. In some embodiments, the class B CpG oligonucleotide is DNA. In some embodiments, the oligonucleotide shell comprises about 5 to about 150 oligonucleotides. In further embodiments, the oligonucleotide shell comprises about 5 to about 50 oligonucleotides. In further embodiments, the oligonucleotide shell comprises about 75 to about 100 oligonucleotides. In some embodiments, the ratio of class A CpG oligonucleotides to class B CpG oligonucleotides in the mixture is about 7:3. In further embodiments, the ratio of class A CpG oligonucleotides to class B CpG oligonucleotides in the mixture is about 4:1 to about 1:1. In some embodiments, each class A CpG oligonucleotide is about 10 to about 50 nucleotides in length. In further embodiments, each class A CpG oligonucleotide is about 15 to about 26 nucleotides in length. In some embodiments, each class B CpG oligonucleotide is about 10 to about 50 nucleotides in length. In some embodiments, each class B CpG oligonucleotide is about 18 to about 28 nucleotides in length. In some embodiments, a SNA of the disclosure further comprises an inhibitory oligonucleotide. In further embodiments, the inhibitory oligonucleotide is an antagonist oligonucleotide, antisense DNA, small interfering RNA (siRNA), an aptamer, a short hairpin RNA (shRNA), a DNAzyme, or an aptazyme. In some embodiments, the nanoparticle core is a metallic core, a semiconductor core, an insulator core, an upconverting core, a micellar core, a dendrimer core, a liposomal core, a polymer core, a metal-organic framework core, a protein core, or a combination thereof. In some embodiments, the polymer is polylactide, a polylactide-polyglycolide copolymer, a polycaprolactone, a polyacrylate, alginate, albumin, polypyrrole, polythiophene, polyaniline, polyethylenimine, poly(methyl methacrylate), poly(lactic-co-glycolic acid) (PLGA), or chitosan. In some embodiments, the nanoparticle core is gold, silver, platinum, aluminum, palladium, copper, cobalt, indium, cadmium selenide, iron oxide, fullerene, metal-organic framework, silica, zinc sulfide, or nickel.

In some embodiments, the nanoparticle core is a protein core. In further embodiments, the protein core is an enzyme, a therapeutic protein, a structural protein, a defensive protein, a storage protein, a transport protein, a hormone, a receptor protein, a motor protein, or a fluorescent protein. In some embodiments, a SNA of the disclosure further comprises an additional agent. In further embodiments, the additional agent is a protein, a small molecule, or a peptide, or a combination thereof. In some embodiments, the protein is an antibody, an antigen, a cytokine, a chemokine, an interferon, or a combination thereof. In some embodiments, the SNA is from about 1 to about 150 nanometers (nm) in diameter. In some embodiments, the oligonucleotide shell comprises about 4 to about 1000 oligonucleotides.

In some aspects, the disclosure provides a composition comprising a plurality of spherical nucleic acids (SNAs) of the disclosure.

In further aspects, the disclosure provides a method of inhibiting expression of a gene comprising the step of hybridizing a polynucleotide encoding the gene product with a spherical nucleic acid (SNA) or composition of the disclosure, wherein hybridizing between the polynucleotide and one or more oligonucleotides in the oligonucleotide shell occurs over a length of the polynucleotide with a degree of complementarity sufficient to inhibit expression of the gene product. In some embodiments, expression of the gene product is inhibited in vivo. In some embodiments, expression of the gene product is inhibited in vitro.

In some aspects, the disclosure provides a method for up-regulating activity of a toll-like receptor (TLR), comprising contacting a cell having the toll-like receptor with a spherical nucleic acid (SNA) or composition of the disclosure. In some embodiments, the oligonucleotide shell further comprises one or more oligonucleotides that is a TLR agonist. In various embodiments, the toll-like receptor is chosen from the group consisting of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13.

In some aspects, the disclosure provides a method for down-regulating activity of a toll-like receptor (TLR), comprising contacting a cell having the toll-like receptor with a spherical nucleic acid (SNA) or composition of the disclosure. In some embodiments, the oligonucleotide shell further comprises one or more oligonucleotides that is a TLR antagonist. In further embodiments, the toll-like receptor is chosen from the group consisting of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13. In some embodiments, the method is performed in vitro. In some embodiments, the method is performed in vivo.

In some aspects, the disclosure provides a method of treating a disorder comprising administering an effective amount of a SNA or composition of the disclosure to a subject in need thereof, wherein the administering treats the disorder. In some embodiments, the disorder is cancer, an infectious disease, an autoimmune disease, or a combination thereof.

DETAILED DESCRIPTION

Figure 1:
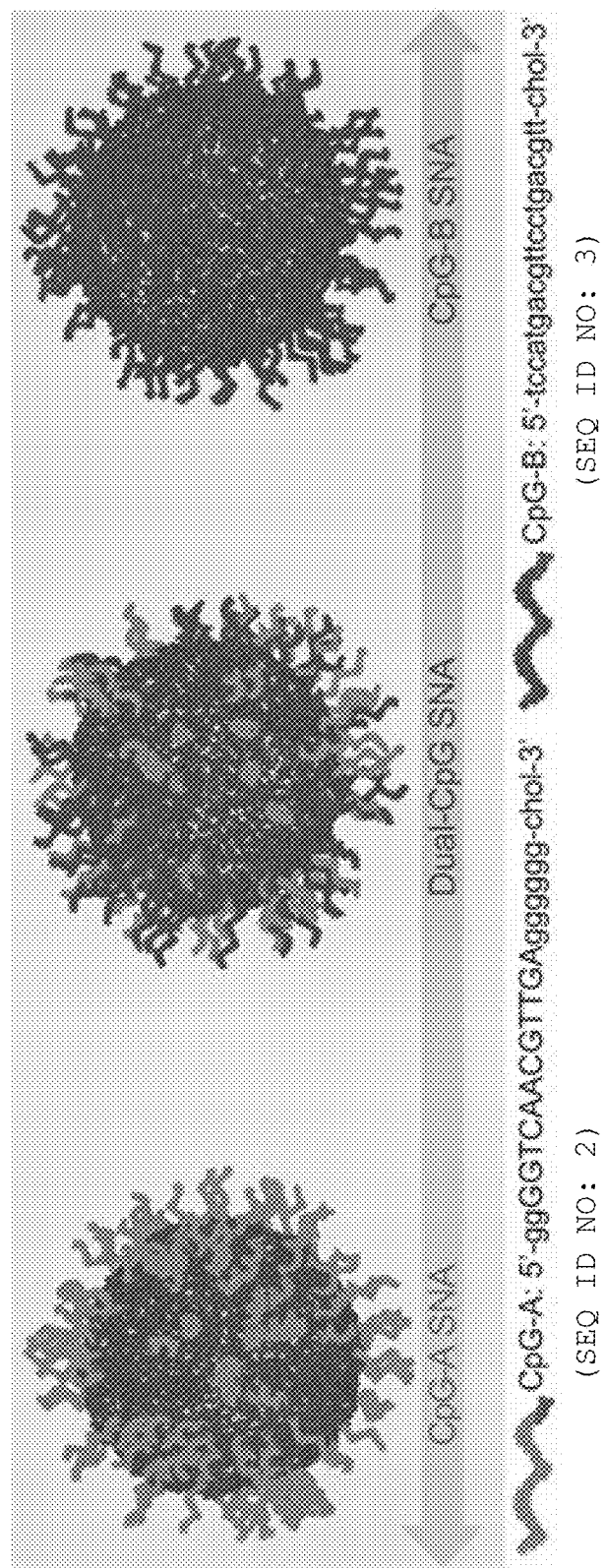
FIG. 1 depicts SNA designs with sequence multiplicity. Upper case letters=nucleobases with PO backbone; lower case letters=nucleobases with PS backbone; chol=cholesterol anchor.

Spherical nucleic acids (SNAs) are a novel class of nanoscale nucleic acids with demonstrated utility in a wide variety of biomedical applications, including gene regulation, cancer immunotherapy, and intracellular detection. To date, SNAs have been primarily generated from a single class of oligonucleotide, but the delivery of multiple classes of oligonucleotides with defined ratios to the same target cell would be advantageous for myriad biological applications. There are numerous applications where it may be beneficial to deliver multiple oligonucleotide sequences to the same target cell.[16] Therefore, the present disclosure elucidates the additive effects of sequence multiplicity (i.e., multiple distinct oligonucleotide sequences on a single SNA construct) on the chemical and physical properties of SNAs in the context of a cell-regulatory process, immunostimulation.

Oligonucleotides have been commonly encapsulated inside liposomes or polymers, but such process is somewhat limited. Multiple sequence encapsulation efficiency is not guaranteed, as some sequences are more easily encapsulated than others, and the encapsulation ratio may have large variations since the encapsulated entities cannot exchange. Some sequences, such as class A CpG, cannot be encapsulated. Spherical nucleic acids can overcome these challenges and incorporate a variety of physically (e.g., structural features) and chemically (e.g., backbone chemistry) distinct oligonucleotide sequences with more controlled ratios. Sequence multiplicity spherical nucleic acids (SNAs) as described herein provide a platform for co-delivery of multiple oligonucleotide sequences at controlled ratios for synergistic therapeutic effects.

As used in this specification and the appended claims, the singular forms "a," "an," and "the" include plural reference unless the context clearly dictates otherwise.

The terms "class A CpG oligonucleotide" and "CpG-A" are interchangeable as used herein. The terms "class B CpG oligonucleotide" and "CpG-B" are interchangeable as used herein. The terms "class C CpG oligonucleotide" and "CpG-C" are interchangeable as used herein.

The terms "polynucleotide" and "oligonucleotide" are interchangeable as used herein.

As used herein, the term "about," when used to modify a particular value or range, generally means within 20 percent, e.g., within 10 percent, 5 percent, 4 percent, 3 percent, 2 percent, or 1 percent of the stated value or range.

Unless otherwise stated, all ranges contemplated herein include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

Spherical Nucleic Acids (SNAs)

As described herein, SNAs comprise a nanoparticle core surrounded by a shell of highly oriented oligonucleotides. In various embodiments, an oligonucleotide shell is formed when at least 10% of the available surface area of the exterior surface of a nanoparticle core includes an oligonucleotide. In further embodiments at least 20%, 30%, 40%, 50%, 60%, 70%, 80%, 90%, 95%, 96%, 97%, 98% or 99% of the available surface area of the exterior surface of the nanoparticle core includes an oligonucleotide. The oligonucleotides of the oligonucleotide shell may be oriented in a variety of directions. In some embodiments the oligonucleotides are oriented radially outwards. The oligonucleotide shell comprises one or more oligonucleotides attached to the external surface of the nanoparticle core. The nanoparticle core can either be organic (e.g., a liposome), inorganic (e.g., gold, silver, or platinum), or hollow (e.g., silica-based). The spherical architecture of the polynucleotide shell confers unique advantages over traditional nucleic acid delivery methods, including entry into nearly all cells independent of transfection agents and resistance to nuclease degradation. Furthermore, SNAs can penetrate biological barriers, including the blood-brain (see, e.g., U.S. Patent Application Publication No. 2015/0031745, incorporated by reference herein in its entirety) and blood-tumor barriers as well as the epidermis (see, e.g., U.S. Patent Application Publication No. 2010/0233270, incorporated by reference herein in its entirety).

SNAs can range in size from about 1 nanometer (nm) to about 500 nm, about 1 nm to about 400 nm, about 1 nm to about 300 nm, about 1 nm to about 200 nm, about 1 nm to about 150 nm, about 1 nm to about 100 nm, about 1 nm to about 90 nm, about 1 nm to about 80 nm in diameter, about 1 nm to about 70 nm in diameter, about 1 nm to about 60 nm in diameter, about 1 nm to about 50 nm in diameter, about 1 nm to about 40 nm in diameter, about 1 nm to about 30 nm in diameter, about 1 nm to about 20 nm in diameter, about 1 nm to about 10 nm, about 10 nm to about 150 nm in diameter, about 10 nm to about 140 nm in diameter, about 10 nm to about 130 nm in diameter, about 10 nm to about 120 nm in diameter, about 10 nm to about 110 nm in diameter, about 10 nm to about 100 nm in diameter, about 10 nm to about 90 nm in diameter, about 10 nm to about 80 nm in diameter, about 10 nm to about 70 nm in diameter, about 10 nm to about 60 nm in diameter, about 10 nm to about 50 nm in diameter, about 10 nm to about 40 nm in diameter, about 10 nm to about 30 nm in diameter, or about 10 nm to about 20 nm in diameter. In some embodiments, the SNA is about 1.4 nm in diameter. In further embodiments, the SNA is, is at least, or is less than about 100 nm, 90 nm, 80 nm, 70 nm, 60 nm, 50 nm, 40 nm, 30 nm, 20, or 10 nm in diameter (or in mean diameter when there are a plurality of SNAs). In further aspects, the disclosure provides a plurality of SNAs, each SNA comprising an oligonucleotide shell attached to the external surface of the nanoparticle core, wherein the oligonucleotide shell comprises or consists of a mixture of class A CpG oligonucleotides and class B CpG oligonucleotides. Thus, in some embodiments, the size of the plurality of SNAs is from about 10 nm to about 150 nm (mean diameter), about 10 nm to about 140 nm in mean diameter, about 10 nm to about 130 nm in mean diameter, about 10 nm to about 120 nm in mean diameter, about 10 nm to about 110 nm in mean diameter, about 10 nm to about 100 nm in mean diameter, about 10 nm to about 90 nm in mean diameter, about 10 nm to about 80 nm in mean diameter, about 10 nm to about 70 nm in mean diameter, about 10 nm to about 60 nm in mean diameter, about 10 nm to about 50 nm in mean diameter, about 10 nm to about 40 nm in mean diameter, about 10 nm to about 30 nm in mean diameter, or about 10 nm to about 20 nm in mean diameter. In some embodiments, the mean diameter of the plurality of SNAs is about 1.4 nm. In some embodiments, the diameter (or mean diameter for a plurality of SNAs) of the SNAs is from about 10 nm to about 150 nm, from about 30 to about 100 nm, or from about 40 to about 80 nm. In some embodiments, the size of the nanoparticles used in a method varies as required by their particular use or application. The variation of size is advantageously used to optimize certain physical characteristics of the SNAs, for example, the amount of surface area to which oligonucleotides may be attached as described herein. It will be understood that the foregoing diameters of SNAs can apply to the diameter of the nanoparticle core itself or to the diameter of the nanoparticle core and the oligonucleotide shell attached thereto. Further description of nanoparticle cores is provided herein below.

Oligonucleotides

CpG Oligonucleotides

Previous work has shown that SNAs with excellent immunostimulatory and immunomodulatory properties can be generated by employing synthetic oligonucleotides (e.g., oligodeoxynucleotides) that contain unmethylated cytosine-guanosine sequences, known as a CpG motif (CpG oligonucleotide (e.g., a CpG ODN), as the oligonucleotide shell.[5-8] Treatment with immunostimulatory SNAs has demonstrated superior antitumor efficacy in multiple mouse models of cancer.[5, 8] CpG oligonucleotides (e.g., ODNs), oligonucleotides that mimic the genome of most bacteria and DNA viruses, are toll-like receptor 9 (TLR9) ligands that induce downstream activation of the myeloid differentiation primary response gene 88 (MyD88)-dependent signaling pathway, which leads to secretion of type I interferons (IFN) and cytokines.[17-18] CpG oligonucleotides (e.g., ODNs) are generally categorized into a few classes. Among them, class A CpG oligonucleotides and class B CpG oligonucleotides were the first two classes identified and are optimal in activating different immune pathways, while other CpG classes show intermediate responses.[19] In some embodiments, CpG-A has a partial phosphodiester (PO) backbone that comprises or consists of an internal CpG-containing palindrome and a partial phosphorothioate (PS) backbone that comprises or consists of poly(G) sequences on the terminals of the strands, while in further embodiments CpG-B comprises a fully PS backbone with hexamer CpG motifs. It has been reported in the literature that the combination of CpG-A and CpG-B ODNs have shown striking synergy, resulting in in vivo mouse survival after tumor challenge.[20]

In various aspects, the present disclosure describes immune activation as a function of, for example and without limitation, the combination (and in some embodiments, the ratio) of class A CpG oligonucleotides and class B CpG oligonucleotides in the context of the SNA platform. Such dual-CpG SNAs are shown herein to enhance immune cell activation relative to a SNA comprising only a single class of CpG oligonucleotide (e.g., class B CpG oligonucleotides). In any of the aspects or embodiments of the disclosure, the SNA does not comprise a class C CpG oligonucleotide (CpG-C).

Class A CpG oligonucleotides, class B CpG oligonucleotides, and class C CpG oligonucleotides are generally understood in the art. CpG oligonucleotides are also described in, e.g., U.S. Pat. No. 6,552,006, Krieg, J Clin Invest. 117(5): 1184-1194 (2007), and Hanagata, Int J Nanomedicine 7: 2181-2195 (2012), each of which is incorporated by reference herein in its entirety.

Class A CpG oligonucleotides are characterized by the ability to induce high levels of interferon-alpha while having minimal effects on TLR9-dependent NF-κB signaling and proinflammatory cytokine (e.g., IL-6) production. In general, class A CpG oligonucleotides are characterized by a central palindromic phosphodiester (PO) CpG motif and a poly(G) sequence at its 3' end. Typically, at least the C of the CpG dinucleotide is unmethylated. In various embodiments, a class A CpG oligonucleotide comprises a central CpG-containing palindromic sequence and an at least partially phosphorothioated (PS) poly(G) sequence at its 5' and/or 3' end. In various embodiments, "at least partially phosphorothioated" means that about 40%, about 50%, about 60%, about 70%, about 80%, about 90%, or 100% of the guanines in the poly(G) sequence are phosphorothioated. In various embodiments, a class A CpG oligonucleotide contains all (i.e., 100%) PS or all PO internucleotide linkages. In some embodiments, the central palindromic CpG motif is or comprises TCAACGTTGA (SEQ ID NO: 1). In any of the aspects or embodiments of the disclosure, a class A CpG oligonucleotide is a DNA molecule. In any of the aspects or embodiments of the disclosure a class A CpG oligonucleotide is a single-stranded DNA molecule. In some embodiments, a class A CpG oligonucleotides comprises (i) an internal palindrome sequence containing a CpG motif and (ii) an at least partially phosphorothioated poly(G) sequence at its 5' and/or 3' ends.

Typically, CpG-B oligonucleotides comprise a full PS backbone with one or more CpG dinucleotides. In various embodiments, a CpG oligonucleotide of the disclosure comprises about 3 to 8 CpG motifs. In further embodiments, a CpG oligonucleotide of the disclosure comprises about 2 to 10, 2 to 9, 2 to 8, 2 to 7, 2 to 6, 2 to 5, 3 to 10, 3 to 9, 3 to 8, 3 to 7, or 3 to 6 CpG motifs. In further embodiments, a CpG oligonucleotide of the disclosure comprises or consists of 2, 3, 4, 5, 6, 7, 8, 9, 10, or more CpG motifs. CpG-B oligonucleotides strongly activate B cells and TLR9-dependent NF-κB signaling but weakly stimulate IFN-α secretion. In any of the aspects or embodiments of the disclosure, a class B CpG oligonucleotide comprises a fully phosphorothioated backbone (i.e., 100% phosphorothioate internucleotide linkages) with one or more CpG motifs. In some embodiments, the CpG motif is a hexamer CpG motif. In some embodiments, the hexamer CpG motif is or comprises GTCGTT. In any of the aspects or embodiments of the disclosure, a class B CpG oligonucleotide is a DNA molecule. In any of the aspects or embodiments of the disclosure a class B CpG oligonucleotide is a single-stranded DNA molecule.

In general, CpG-C oligonucleotides combine features of both classes A and B. Typically, CpG-C oligonucleotides comprise a complete PS backbone and a CpG-containing palindromic motif. C-Class CpG ODNs induce strong IFN-α production as well as B cell stimulation. In various embodiments, a class C CpG oligonucleotide comprises a phosphorothioate backbone, a phosphodiester backbone, or a combination thereof. In some embodiments, a class C CpG oligonucleotide is a DNA molecule. In some embodiments, a class C CpG oligonucleotide is a single-stranded DNA molecule.

As used herein, a "poly(G) sequence" is a nucleotide sequence of three or more consecutive G's, e.g., 5'-GGG-3', occurring at the 5' end and/or the 3' end of an oligonucleotide. As used herein, "CpG" refers to a "CpG-motif containing oligonucleotide," i.e., the entire oligonucleotide. A "CpG motif" as used herein is the "CG" sequence within an oligonucleotide that is the ligand for TLR9 binding and activation (while the rest of the oligonucleotide sequence, in various embodiments, helps the oligonucleotide form a structure that facilitates CpG motif binding to TLR9. A "palindrome" or "palindromic sequence" refers to a sequence of nucleotides along an oligonucleotide strand that reads the same in the 5'→3' direction as its complementary strand reads in the 5' →3' direction. Palindromic sequences in a single stranded oligonucleotide can fold into a hairpin structure. By way of example, a palindromic sequence is TCAACGTTGA (SEQ ID NO: 1).

Oligonucleotide Features

It will be understood that all features of oligonucleotides described herein (e.g., type (DNA/RNA/chimeric), single/double stranded, length, sequence, modified forms) apply to all oligonucleotides described herein, including CpG oligonucleotides and oligonucleotides that are not CpG oligonucleotides (e.g., an inhibitory oligonucleotide). The disclosure provides spherical nucleic acids (SNAs) comprising a nanoparticle core and an oligonucleotide shell attached to the external surface of the nanoparticle core. In some embodiments, the oligonucleotide shell comprises a mixture of class A CpG oligonucleotides and class B CpG oligonucleotides, wherein the SNA does not comprise a class C CpG oligonucleotide. In some embodiments, the oligonucleotide shell consists of a mixture of class A CpG oligonucleotides and class B CpG oligonucleotides. In some embodiments, the oligonucleotide shell comprises a mixture of class A CpG oligonucleotides and class B CpG oligonucleotides, wherein the ratio of class A CpG oligonucleotides to class B CpG oligonucleotides in the mixture is about 4:1 to about 1:1.

Oligonucleotides (e.g., CpG oligonucleotides) of the disclosure include, in various embodiments, DNA oligonucleotides, RNA oligonucleotides, modified forms thereof, or a combination thereof. Thus, in some embodiments, the CpG oligonucleotide is DNA oligonucleotide, RNA oligonucleotide, a modified oligonucleotide, or a combination thereof. In various embodiments, an oligonucleotide shell of the disclosure comprises DNA oligonucleotides, RNA oligonucleotides, modified oligonucleotides, or a combination thereof.

In any aspects or embodiments described herein, an oligonucleotide is single-stranded, double-stranded, or partially double-stranded. In various embodiments, an oligonucleotide shell of the disclosure comprises single stranded oligonucleotides, double stranded oligonucleotides, partially double stranded oligonucleotides, or a combination thereof.

As described herein, modified forms of oligonucleotides are also contemplated by the disclosure which include those having at least one modified internucleotide linkage. In some embodiments, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function, e.g., as a probe in hybridization. Examples of universal bases include but are not limited to 5'-nitroindole-2'-deoxyriboside, 3-nitropyrrole, inosine and hypoxanthine.

The term "nucleotide" or its plural as used herein is interchangeable with modified forms as discussed herein and otherwise known in the art. The term "nucleobase" or its plural as used herein is interchangeable with modified forms as discussed herein and otherwise known in the art. Nucleotides or nucleobases comprise the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, oligonucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still further embodiments, oligonucleotide mimetics wherein both one or more sugar and/or one or more internucleotide linkage of the nucleotide units are replaced with "non-naturally occurring" groups. The bases of the oligonucleotide are maintained for hybridization.

In some aspects, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still further embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligonucleotide consists of 2 to 4, desirably 3, groups/atoms selected from —$CH_2$—, —O—, —S—, —$NR^H$—, >C=O, >C=$NR^H$, >=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—NR—, —$NR^H$—CO—O—, —NR—CO—$NR^H$, —$NR^H$—CS—$NR^H$—, —$NR^H$—C(=$NR^H$)—$NR^H$—, —$NR^H$—CO—$CH_2$—$NR^H$—CO—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—NRHC, —O—$NR^H$—$CH_2$—, —O—$NR^H$, —O—$CH_2$—S—, —S—$CH_2$—, —$OH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$ H—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—O—P(—O,S)—O—, —O—P(S)$_2$—O—, —NR" P(O)$_2$—O—, —O—P(O,$NR^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[($CH_2$)$_n$O]$_m$CH$_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, or an RNA cleaving group. In one aspect, a modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In some aspects, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

In various aspects, an oligonucleotide of the disclosure (e.g., a CpG oligonucleotide), or a modified form thereof, is generally about 10 nucleotides to about 100 nucleotides in length. More specifically, an oligonucleotide of the disclosure is about 10 to about 90 nucleotides in length, about 10 to about 80 nucleotides in length, about 10 to about 70 nucleotides in length, about 10 to about 60 nucleotides in length, about 10 to about 50 nucleotides in length about 10 to about 45 nucleotides in length, about 10 to about 40 nucleotides in length, about 10 to about 35 nucleotides in length, about 10 to about 30 nucleotides in length, about 10 to about 25 nucleotides in length, about 10 to about 20 nucleotides in length, about 10 to about 15 nucleotides in length, about 18 to about 28 nucleotides in length, about 15 to about 26 nucleotides in length, and all oligonucleotides intermediate in length of the sizes specifically disclosed to the extent that the oligonucleotide is able to achieve the desired result. In further embodiments, an oligonucleotide of the disclosure is about 5 nucleotides to about 1000 nucleotides in length. In further embodiments, an oligonucleotide of the disclosure is about 5 to about 900 nucleotides in length, about 5 to about 800 nucleotides in length, about 5 to about 700 nucleotides in length, about 5 to about 600 nucleotides in length, about 5 to about 500 nucleotides in length about 5 to about 450 nucleotides in length, about 5 to about 400 nucleotides in length, about 5 to about 350 nucleotides in length, about 5 to about 300 nucleotides in length, about 5 to about 250 nucleotides in length, about 5 to about 200 nucleotides in length, about 5 to about 150 nucleotides in length, about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 40 nucleotides in length, about 5 to about 30 nucleotides in length, about 5 to about 20 nucleotides in length, about 5 to about 10 nucleotides in length, and all oligonucleotides intermediate in length of the sizes specifically disclosed to the extent that the oligonucleotide is able to achieve the desired result. Accordingly, in various embodiments, an oligonucleotide of the disclosure is or is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or more nucleotides in length. In further embodiments, an oligonucleotide of the disclosure is less than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or more nucleotides in length. In various embodiments, a SNA comprises a plurality of oligonucleotides that all have the same length/sequence, while in some embodiments, the plurality of oligonucleotides comprises one or more oligonucleotide that have a different length and/or sequence relative to at least one other oligonucleotide in the plurality.

In some embodiments, the oligonucleotide is an aptamer. Accordingly, all features and aspects of oligonucleotides described herein (e.g., length, type (DNA, RNA, modified forms thereof), optional presence of spacer) also apply to aptamers. Aptamers are oligonucleotide sequences that can be evolved to bind to various target analytes of interest. Aptamers may be single stranded, double stranded, or partially double stranded.

Methods of attaching detectable markers (e.g., fluorophores, radiolabels) and additional moieties (e.g., an antibody) as described herein to an oligonucleotide are known in the art.

In various aspects, a SNA of the disclosure has the ability to bind to a plurality of targets (e.g., polynucleotides, proteins). In some embodiments, a SNA further comprises one or more oligonucleotides that are not CpG oligonucleotides. Such oligonucleotides that are not CpG oligonucleotides may be inhibitory oligonucleotides as described herein. Thus, in some embodiments, a SNA of the disclosure comprises one or more oligonucleotides having a sequence sufficiently complementary to the target polynucleotide to hybridize under the conditions being used. In some embodiments, the SNA comprises two or more oligonucleotides that are not identical, i.e., at least one of the attached oligonucleotides differ from at least one other attached oligonucleotide in that it has a different length and/or a different sequence. For example, if a specific polynucleotide is targeted, a single SNA has the ability to bind to multiple copies of the same target. In some embodiments, a single SNA has the ability to bind to different targets Accordingly, in various aspects, a single SNA may be used in a method to inhibit expression of more than one gene product. In various embodiments, oligonucleotides are thus used to target specific polynucleotides, whether at one or more specific regions in the target polynucleotide, or over the entire length of the target polynucleotide as the need may be to effect a desired level of inhibition of gene expression. Accordingly, in various aspects and embodiments of the disclosure, a SNA of the disclosure possesses immunostimulatory activity and inhibition of gene expression activity.

Nanoparticle surface density. A surface density adequate to make the nanoparticles stable and the conditions necessary to obtain it for a desired combination of nanoparticles and oligonucleotides can be determined empirically. In general, oligonucleotides of the disclosure are attached to the nanoparticle core at a surface density of at least about 2 pmoles/cm$^2$. In some aspects, the surface density is about or at least about 15 pmoles/cm$^2$. Methods are also provided wherein oligonucleotides are bound to the nanoparticle core at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more. Alternatively, the density of oligonucleotides attached to the SNA is measured by the number of oligonucleotides attached to the SNA. With respect to the surface density of oligonucleotides attached to an SNA, it is contemplated that a SNA as described herein comprises about 1 to about 2,500, or about 1 to about 500 oligonucleotides on its surface. In various embodiments, a SNA comprises about 10 to about 500, or about 10 to about 300, or about 10 to about 200, or about 10 to about 190, or about 10 to about 180, or about 10 to about 170, or about 10 to about 160, or about 10 to about 150, or about 10 to about 140, or about 10 to about 130, or about 10 to about 120, or about 10 to about 110, or about 10 to about 100, or 10 to about 90, or about 10 to about 80, or about 10 to about 70, or about 10 to about 60, or about 10 to about 50, or about 10 to about 40, or about 10 to about 30, or about 10 to about 20 oligonucleotides in the shell of oligonucleotides attached to the nanoparticle core. In some embodiments, a SNA comprises about 80 to about 140 oligonucleotides in the shell of oligonucleotides attached to the nanoparticle core. In further embodiments, a SNA comprises at least about 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 oligonucleotides in the shell of oligonucleotides attached to the nanoparticle core. In further embodiments, a SNA comprises or consists of 1, 2, 3, 4, 5, 10, 20, 30, 40, 45, 50, 55, 60, 65, 70, 75, 80, 85, 90, 95, 100, 105, 110, 115, 120, 125, 127, 130, 135, 140, 145, 150, 155, 160, 165, 170, 175, 180, 185, 190, 195, 200, 300, 400, 500, 600, 700, 800, 900, or 1000 oligonucleotides in the shell of oligonucleotides attached to the nanoparticle core. In still further embodiments, the shell of oligonucleotides attached to the nanoparticle core of the SNA comprises 2, 3, 4, 5, 6, 7, 8, 9, 10, 11, 12, 13, 14, 15, 16, 17, 18, 19, 20, or more oligonucleotides. In some embodiments, the shell of oligonucleotides attached to the nanoparticle core of the SNA comprises at least 20 oligonucleotides. In some embodiments, the shell of oligonucleotides attached to the nanoparticle core of the SNA consists of 127.5 oligonucleotides. In some embodiments, the shell of oligonucleotides attached to the nanoparticle core of the SNA comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more oligonucleotides. In various embodiments, about 2 to about 1000, or about 2 to about 100 oligonucleotides are attached to the external surface of a nanoparticle core. In further embodiments, about 10 to about 1000, or about 10 to about 750, or about 10 to about 500, or about 10 to about 250, or about 10 to about 100, or about 50 to about 1000, or about 50 to about 750, or about 50 to about 500, or about 50 to about 250, or about 100 to about 1000, or about 100 to about 500, or about 2 to about 90, or about 2 to about 80, or about 2 to about 70, or about 2 to about 60, or about 2 to about 50, or about 2 to about 40, or about 2 to about 30, or about 2 to about 20, or about 2 to about 10, or about 10 to about 100, or about 10 to about 90, or about 10 to about 80, or about 10 to about 70, or about 10 to about 60, or about 10 to about 50, or about 10 to about 40, or about 10 to about 30, or about 10 to about 20, or about 20 to about 100, or about 20 to about 90, or about 20 to about 80, or about 20 to about 70, or about 20 to about 60, or about 20 to about 50, or about 20 to about 40, or about 20 to about 30 oligonucleotides are attached to the external surface of a nanoparticle core. In still further embodiments, at least 1, at least 2, at least 3, at least 4, at least 5, at least 6, at least 7, at least 8, at least 9, or at least 10 oligonucleotides are attached to the nanoparticle core.

In any of the aspects or embodiments of the disclosure, a SNA comprises a mixture of class A CpG oligonucleotides and class B CpG oligonucleotides. In various embodiments, the number of class A CpG oligonucleotides and class B CpG oligonucleotides attached to a nanoparticle core are varied to achieve SNAs having various ratios of class A CpG oligonucleotides to class B CpG oligonucleotides. In some embodiments, the ratio of class A CpG oligonucleotides to class B CpG oligonucleotides in the mixture is or is about 4:1 to about 1:1. In some embodiments, the ratio of class A CpG oligonucleotides to class B CpG oligonucleotides in the mixture is or is about 7:3. In further embodiments, the ratio of class A CpG oligonucleotides to class B CpG oligonucleotides in the mixture is or is about 4:1 to about 2:1, or about 4:1 to about 3:1, or about 3:1 to about 2:1, or about 3:1 to about 1:1. In still further embodiments, the ratio of class A CpG oligonucleotides to class B CpG oligonucleotides in the mixture is, is about, or is at least about 1:1, 1:9, 1:4, 3:7, 9:1, 2:1, 7:3, 6:4, 3:1, or 4:1. In still further embodiments, the ratio of class A CpG oligonucleotides to class B CpG oligonucleotides in the mixture is less than about 1:1, 1:9, 1:4, 3:7, 9:1, 2:1, 7:3, 6:4, 3:1, or 4:1.

In some embodiments, a SNA of the disclosure further comprises one or more class C CpG oligonucleotides.

Spacers. In some aspects, an oligonucleotide (e.g., CpG oligonucleotide) is attached to a nanoparticle through a spacer (and, in some embodiments, additionally through a linker). "Spacer" as used herein means a moiety that serves to increase distance between the nanoparticle and the oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences.

In some aspects, the spacer when present is an organic moiety. In some aspects, the spacer is a polymer, including but not limited to a water-soluble polymer, a nucleic acid, a polypeptide, an oligosaccharide, a carbohydrate, a lipid, an ethylglycol, or a combination thereof. In any of the aspects or embodiments of the disclosure, the spacer is an oligo (ethylene glycol)-based spacer. In various embodiments, an oligonucleotide comprises 1, 2, 3, 4, 5, or more spacer (e.g., Spacer-18 (hexaethyleneglycol)) moieties. In further embodiments, the spacer is an alkane-based spacer (e.g., C12). In some embodiments, the spacer is an oligonucleotide spacer (e.g., T5). An oligonucleotide spacer may have any sequence that does not interfere with the ability of the oligonucleotide to perform an intended function (e.g., stimulate an immune response or inhibit gene expression). In certain aspects, the bases of the oligonucleotide spacer are all adenylic acids, all thymidylic acids, all cytidylic acids, all guanylic acids, all uridylic acids, or all some other modified base.

In various embodiments, the length of the spacer is or is equivalent to at least about 2 nucleotides, at least about 3 nucleotides, at least about 4 nucleotides, at least about 5 nucleotides, 5-10 nucleotides, 10 nucleotides, 20 nucleotides, 10-30 nucleotides, or even greater than 30 nucleotides.

Olicionucleotide attachment to a nanoparticle core. Oligonucleotides contemplated for use according to the disclosure include those attached to a nanoparticle core through any means (e.g., covalent or non-covalent attachment). Regardless of the means by which the oligonucleotide is attached to the nanoparticle, attachment in various aspects is effected through a 5' linkage, a 3' linkage, some type of internal linkage, or any combination of these attachments. In some embodiments, the oligonucleotide is covalently attached to a nanoparticle. In further embodiments, the oligonucleotide is non-covalently attached to a nanoparticle. In further embodiments, the oligonucleotide is attached to a nanoparticle via a combination of covalent and non-covalent linkage.

Methods of attachment are known to those of ordinary skill in the art and are described in U.S. Publication No. 2009/0209629, which is incorporated by reference herein in its entirety. Methods of attaching RNA to a nanoparticle are generally described in PCT/US2009/65822, which is incorporated by reference herein in its entirety. Methods of associating oligonucleotides with a liposomal particle are described in PCT/US2014/068429, which is incorporated by reference herein in its entirety.

Methods of attaching oligonucleotides to a protein core are described, e.g., in U.S. Patent Application Publication No. 2017/0232109 and Brodin et al., J Am Chem Soc. 137(47): 14838-41 (2015), each of which is incorporated by reference herein in its entirety. In general, a polynucleotide can be modified at a terminus with an alkyne moiety, e.g., a DBCO-type moiety for reaction with the azide of the protein surface:

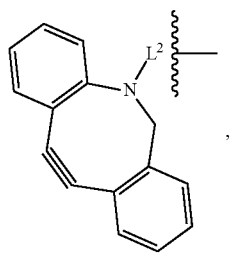

, where L is a linker to a terminus of the polynucleotide. $L^2$ can be $C_{1-10}$ alkylene, alkylene-Y—, and —C(O)—$C_{1-10}$ alkylene-Y-alkylene-$(OCH_2CH_2)_m$—Y—; wherein each Y is independently selected from the group consisting of a bond, C(O), O, NH, C(O)NH, and NHC(O); and m is 0, 1, 2, 3, 4, or 5. For example, the DBCO functional group can be attached via a linker having a structure of

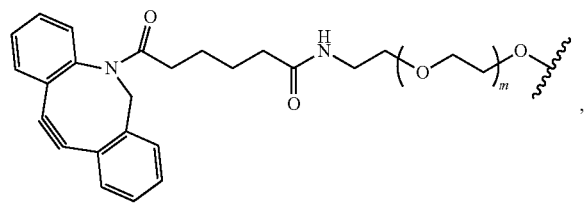

, where the terminal "0" is from a terminal nucleotide on the polynucleotide. Use of this DBCO-type moiety results in a structure between the polynucleotide and the protein, in cases where a surface amine is modified, of:

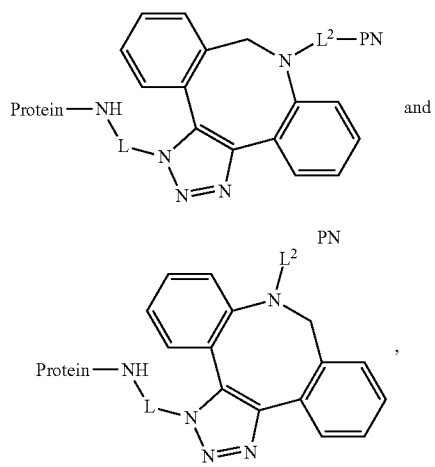

, where L and $L^2$ are each independently selected from $C_{1-10}$ alkylene, alkylene-Y—, and —C(O)—$C_{1-10}$ alkylene-Y—$C_{1-10}$ alkylene-$(OCH_2CH_2)_m$—Y—; each Y is independently selected from the group consisting of a bond, C(O), O, NH, C(O)NH, and NHC(O); m is 0, 1, 2, 3, 4, or 5; and PN is the polynucleotide. Similar structures where a surface thiol or surface carboxylate of the protein are modified can be made in a similar fashion to result in comparable linkage structures.

The protein can be modified at a surface functional group (e.g., a surface amine, a surface carboxylate, a surface thiol) with a linker that terminates with an azide functional group: Protein-X-L-$N_3$, X is from a surface amino group (e.g., —NH—), carboxylic group (e.g., —C(O)— or —C(O)O—), or thiol group (e.g., —S—) on the protein; L is selected from $C_{1-10}$ alkylene, —Y—C(O)—$C_{1-10}$ alkylene-Y—, and —Y—C(O)—$C_{1-10}$ alkylene-Y-alkylene-$(OCH_2CH_2)_m$—Y—; each Y is independently selected from the group consisting of a bond, C(O), O, NH, C(O)NH, and NHC(O); and m is 0, 1, 2, 3, 4, or 5. Introduction of the "L-$N_3$" functional group to the surface moiety of the protein can be accomplished using well-known techniques. For example, a surface amine of the protein can be reacted with an activated ester of a linker having a terminal $N_3$ to form an amide bond between the amine of the protein and the carboxylate of the activated ester of the linker reagent.

The polynucleotide can be modified to include an alkyne functional group at a terminus of the polynucleotide: Polynucleotide-$L_2$-X-E-R; $L^2$ is selected from $C_{1-10}$ alkylene, alkylene-Y—, and —C(O)—$C_{1-10}$ alkylene-Y-alkylene-$(OCH_2CH_2)_m$—Y—; each Y is independently selected from the group consisting of a bond, C(O), O, NH, C(O)NH, and NHC(O); m is 0, 1, 2, 3, 4, or 5; and X is a bond and R is H or $C_{1-10}$alkyl; or X and R together with the carbons to which they are attached form a 8-10 membered carbocyclic or 8-10 membered heterocyclic group. In some cases, the polynucleotide has a structure

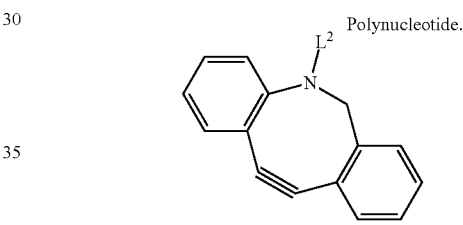

The protein, with the surface modified azide, and the polynucleotide, with a terminus modified to include an alkyne, can be reacted together to form a triazole ring in the presence of a copper (II) salt and a reducing agent to generate a copper (I) salt in situ. In some cases, a copper (I) salt is directly added. Contemplated reducing agents include ascorbic acid, an ascorbate salt, sodium borohydride, 2-mercaptoethanol, dithiothreitol (DTT), hydrazine, lithium aluminum hydride, diisobutylaluminum hydride, oxalic acid, Lindlar catalyst, a sulfite compound, a stannous compound, a ferrous compound, sodium amalgam, tris(2-carboxyethyl) phosphine, hydroquinone, and mixtures thereof.

The surface functional group of the protein can be attached to the polynucleotide using other attachment chemistries. For example, a surface amine can be directed conjugated to a carboxylate or activated ester at a terminus of the polynucleotide, to form an amide bond. A surface carboxylate can be conjugated to an amine on a terminus of the polynucleotide to form an amide bond. Alternatively, the surface carboxylate can be reacted with a diamine to form an amide bond at the surface carboxylate and an amine at the other terminus. This terminal amine can then be modified in a manner similar to that for a surface amine of the protein. A surface thiol can be conjugated with a thiol moiety on the polynucleotide to form a disulfide bond. Alternatively, the thiol can be conjugated with an activated ester on a terminus of a polynucleotide to form a thiocarboxylate.

Nanoparticle Core

In general, nanoparticles contemplated by the disclosure include any compound or substance with a high loading capacity for an oligonucleotide as described herein, including for example and without limitation, a protein, a metal, a semiconductor, a liposomal particle, a polymer-based particle (e.g., a poly (lactic-co-glycolic acid) (PLGA) particle), insulator particle compositions, and a dendrimer (organic versus inorganic). Thus, in various embodiments, the nanoparticle core is organic (e.g., a liposome), inorganic (e.g., gold, silver, or platinum), porous (e.g., silica-based or metal organic-framework-based), or hollow. In any of the aspects or embodiments of the disclosure, the nanoparticle core is a protein core.

Thus, the disclosure contemplates nanoparticle cores that comprise a variety of inorganic materials including, but not limited to, metals, semi-conductor materials or ceramics as described in U.S. Patent Publication No 20030147966. For example, metal-based nanoparticles include those described herein. In various embodiments, the nanoparticle core is a metallic core, a semiconductor core, an insulator core, an upconverting core, a micellar core, a dendrimer core, a liposomal core, a polymer core, a metal-organic framework core, a protein core, or a combination thereof. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g., polypeptides such as BSA, polysaccharides, etc.), other biological materials (e.g., carbohydrates), and/or polymeric compounds are also contemplated for use in producing nanoparticles. In some embodiments, the polymer is polylactide, a polylactide-polyglycolide copolymer, a polycaprolactone, a polyacrylate, alginate, albumin, polypyrrole, polythiophene, polyaniline, polyethylenimine, poly(methyl methacrylate), chitosan, or a related structure. In some embodiments, the polymer is poly(lactic-co-glycolic acid) (PLGA).

Liposomal particles, for example as disclosed in International Patent Application No. PCT/US2014/068429 and U.S. Pat. No. 10,792,251 (each of which is incorporated by reference herein in its entirety) are also contemplated by the disclosure. Hollow particles, for example as described in U.S. Patent Publication Number 2012/0282186 (incorporated by reference herein in its entirety) are also contemplated herein. Liposomes of the disclosure have at least a substantially spherical geometry, an internal side and an external side, and comprise a lipid bilayer. The lipid bilayer comprises, in various embodiments, a lipid from the phosphocholine family of lipids or the phosphoethanolamine family of lipids. In various embodiments, the lipid is 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), cardiolipin, lipid A, cell-derived lipids, or a combination thereof.

In some embodiments, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe_3O_4$, $Fe_2O_3$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992). In some embodiments, the nanoparticle is an iron oxide nanoparticle. In further embodiments, the nanoparticle core is gold, silver, platinum, aluminum, palladium, copper, cobalt, indium, cadmium selenide, iron oxide, fullerene, metal-organic framework, zinc sulfide, or nickel.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramido-amine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold).

In any of the aspects or embodiments of the disclosure, the nanoparticle core is a protein. As used herein, "protein" is used interchangeably with "polypeptide" and refers to one or more polymers of amino acid residues. In various embodiments of the disclosure, a protein core comprises or consists of a single protein (i.e., a single polymer of amino acids), a multimeric protein, a peptide (e.g., a polymer of amino acids that between about 2 and 50 amino acids in length), or a synthetic fusion protein of two or more proteins. Synthetic fusion proteins include, without limitation, an expressed fusion protein (expressed from a single gene) and post-expression fusions where proteins are conjugated together chemically. Protein/oligonucleotide core-shell nanoparticles are also generally described in U.S. Patent Application Publication No. 2017/0232109, which is incorporated by reference herein in its entirety.

Proteins are understood in the art and include without limitation an enzyme, a therapeutic protein (e.g., adenosine deaminase, phosphatase and tensin homolog (PTEN), an interleukin (e.g., IL-1, IL-2, IL-6, IL-10, IL-12, etc.), an interferon (e.g., IFN-α, IFN-β, IFN-γ), or tumor necrosis factor alpha (TNF-α), a structural protein (e.g., actin), an antibody, a storage protein (e.g., ovalbumin), a transport protein (e.g., hemoglobin), a hormone (e.g., insulin), a receptor protein (e.g., G-Protein Coupled Receptors), a motor protein (e.g., kinesin, dynein, or myosin), an immunogenic protein (e.g., ovalbumin or a stimulator of interferon genes (STING) protein) or a fluorescent protein (e.g., green fluorescent protein (GFP)). In various embodiments, proteins contemplated by the disclosure include without limitation those having catalytic, signaling, therapeutic, or transport activity.

Proteins of the present disclosure may be either naturally occurring or non-naturally occurring. Proteins optionally include a spacer as described herein.

Naturally occurring proteins include without limitation biologically active proteins (including antibodies) that exist in nature or can be produced in a form that is found in nature by, for example, chemical synthesis or recombinant expression techniques. Thus, a protein core of the disclosure is or comprises, in some embodiments, an antibody. Naturally occurring proteins also include lipoproteins and post-translationally modified proteins, such as, for example and without limitation, glycosylated proteins. Antibodies contemplated for use in the methods and compositions of the present disclosure include without limitation antibodies that recognize and associate with a target molecule either in vivo or in vitro.

Structural proteins contemplated by the disclosure include without limitation actin, tubulin, collagen, and elastin.

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure. The term "peptide" typically refers to short (e.g., about 2-50 amino acids in length) polypeptides/proteins. Non-naturally occurring proteins are prepared, for example, using an automated protein synthesizer or, alternatively, using recombinant expression techniques using a modified polynucleotide which encodes the desired protein.

As used herein a "fragment" of a protein is meant to refer to any portion of a protein smaller than the full-length protein or protein expression product. As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it. As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, proteins are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

Proteins include antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

SNA Synthesis

As described herein, SNAs of the disclosure generally comprise a nanoparticle core and an oligonucleotide shell comprising a mixture of CpG oligonucleotides. CpG oligonucleotides of the disclosure are immunostimulatory oligonucleotides, that is, they are capable of activating an immune cell. SNAs of the disclosure are therefore synthesized such that an oligonucleotide shell comprising a mixture of CpG oligonucleotides is attached to the external surface of a nanoparticle core. In some embodiments, the disclosure contemplates that a SNA comprises one or more oligonucleotides encapsulated within the SNA (e.g., within the nanoparticle core of the SNA). Syntheses of SNAs is described in detail herein (e.g., Example 1).

Uses of SNAs in Gene Regulation/Therapy

It is contemplated that in any of the aspects or embodiments of the disclosure, a SNA as disclosed herein possesses the ability to regulate gene expression. Thus, in some embodiments, a SNA of the disclosure comprises a nanoparticle core and an oligonucleotide shell attached to the external surface of the nanoparticle core, wherein the oligonucleotide shell comprises a mixture of class A CpG oligonucleotides and class B CpG oligonucleotides, and the SNA further comprises one or more oligonucleotides having gene regulatory activity (e.g., inhibition of target gene expression or target cell recognition). In some embodiments, a SNA of the disclosure comprises one or more oligonucleotides that is an inhibitory oligonucleotide as described herein. Accordingly, in some embodiments the disclosure provides methods for inhibiting gene product expression, and such methods include those wherein expression of a target gene product is inhibited by about or at least about 5%, about or at least about 10%, about or at least about 15%, about or at least about 20%, about or at least about 25%, about or at least about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% compared to gene product expression in the absence of a SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of SNA and a specific oligonucleotide. In various aspects, the methods include use of an oligonucleotide branch sufficiently complementary to a target polynucleotide as described herein.

Accordingly, methods of utilizing a SNA of the disclosure in gene regulation therapy are provided. This method comprises the step of hybridizing a target polynucleotide encoding the gene product with one or more oligonucleotides of a SNA that are complementary to all or a portion of the target polynucleotide, wherein hybridizing between the target polynucleotide and the oligonucleotide occurs over a length of the target polynucleotide with a degree of complementarity sufficient to inhibit expression of the gene product. The inhibition of gene expression may occur in vivo or in vitro.

In various embodiments, the inhibitory oligonucleotide utilized in the methods of the disclosure is RNA, DNA, or a modified form thereof. In various embodiments, the inhibitory oligonucleotide is antisense DNA, small interfering RNA (siRNA), an aptamer, a short hairpin RNA (shRNA), a DNAzyme, or an aptazyme.

Uses of SNAs in Immune Regulation

Toll-like receptors (TLRs) are a class of proteins, expressed in sentinel cells, that play a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that respond to specific oligonucleotides are located inside special intracellular compartments, called endosomes. The mechanism of modulation of, for example and without limitation, TLR 4, TLR 8 and TLR 9 receptors, is based on DNA-protein interactions.

As described herein, synthetic immunostimulatory oligonucleotides that contain CpG motifs that are similar to those found in bacterial DNA stimulate a similar response of the TLR receptors. Thus, CpG oligonucleotides of the disclosure have the ability to function as TLR agonists. Other TLR agonists contemplated by the disclosure include, without limitation, single-stranded RNA and small molecules (e.g., R848 (Resiquimod)). Therefore, immunomodulatory oligonucleotides have various potential therapeutic uses, including treatment of immune deficiency and cancer. Thus, in some embodiments, a SNA of the disclosure is used in a method to modulate the activity of a toll-like receptor (TLR).

In further embodiments, a SNA of the disclosure comprises an oligonucleotide that is a TLR antagonist. In some embodiments, the immunostimulatory oligonucleotide is a double-stranded DNA (dsDNA).

In some embodiments, down regulation of the immune system would involve knocking down the gene responsible for the expression of the Toll-like receptor. This antisense approach involves use of a SNA of the disclosure to knock down the expression of any toll-like protein.

Accordingly, in some embodiments, methods of utilizing SNAs as described herein for modulating toll-like receptors are disclosed. The method either up-regulates or down-regulates the Toll-like-receptor activity through the use of a TLR agonist or a TLR antagonist, respectively. The method comprises contacting a cell having a toll-like receptor with a SNA of the disclosure, thereby modulating the activity and/or the expression of the toll-like receptor. The toll-like receptors modulated include one or more of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and/or toll-like receptor 13.

Uses of SNAs to Treat a Disorder

In some embodiments, a SNA of the disclosure is used to treat a disorder. As used herein, "treat" or "treating" means to eliminate, reduce, or ameliorating the disorder or one or more symptoms thereof. Thus, in some aspects, the disclosure provides methods of treating a disorder comprising administering an effective amount of the SNA of the disclosure to a subject (e.g., a human subject) in need thereof, wherein the administering treats the disorder. In various embodiments, the disorder is cancer, an infectious disease, an autoimmune disease, or a combination thereof. An "effective amount" of the SNA is an amount sufficient to activate an innate immune response. Thus, methods of activating an innate immune response are also contemplated herein, such methods comprising administering a SNA of the disclosure to a subject in need thereof in an amount effective to activate an innate immune response in the subject.

A SNA of the disclosure can be administered via any suitable route, such as parenteral administration, intramuscular injection, subcutaneous injection, intradermal administration, and/or mucosal administration such as oral or intranasal. Additional routes of administration include but are not limited to intravenous, intraperitoneal, intranasal administration, intra-vaginal, intra-rectal, and oral administration. A combination of different routes of administration, separately or at the same time, is also contemplated by the disclosure.

Compositions

The disclosure also provides compositions that comprise a SNA of the disclosure, or a plurality thereof. In some embodiments, the composition further comprises a pharmaceutically acceptable carrier. The term "carrier" refers to a vehicle within which the SNA as described herein is administered to a subject. Any conventional media or agent that is compatible with the SNAs according to the disclosure can be used. The term carrier encompasses diluents, excipients, adjuvants and a combination thereof.

Additional Agents

The SNAs provided herein optionally further comprise an additional agent, or a plurality thereof. The additional agent is, in various embodiments, simply associated with an oligonucleotide in the shell of oligonucleotides attached to the nanoparticle core of the SNA, and/or the additional agent is associated with the nanoparticle core of the SNA, and/or the additional agent is encapsulated in the SNA. In some embodiments, the additional agent is associated with the end of an oligonucleotide that is not attached to the nanoparticle core (e.g., if the oligonucleotide is attached to the nanoparticle core through its 3' end, then the additional agent is associated with the 5' end of the oligonucleotide). Alternatively, in some embodiments, the additional agent is associated with the end of an oligonucleotide that is attached to the nanoparticle core (e.g., if the oligonucleotide is attached to the nanoparticle core through its 3' end, then the additional agent is associated with the 3' end of the oligonucleotide). In some embodiments, the additional agent is covalently associated with an oligonucleotide in the shell of oligonucleotides that is attached to the nanoparticle core of the SNA. In some embodiments, the additional agent is non-covalently associated with an oligonucleotide in the shell of oligonucleotides that is attached to the nanoparticle core of the SNA. However, it is understood that the disclosure provides SNAs wherein one or more additional agents are both covalently and non-covalently associated with oligonucleotides in the shell of oligonucleotides that is attached to the nanoparticle core of the SNA. It will also be understood that non-covalent associations include hybridization, protein binding, and/or hydrophobic interactions. In some embodiments, an additional agent is administered separately from a SNA of the disclosure. Thus, in some embodiments, an additional agent is administered before, after, or concurrently with a SNA of the disclosure to treat a disorder.

Additional agents contemplated by the disclosure include without limitation a protein (e.g., a therapeutic protein), a small molecule, a peptide, or a combination thereof. These additional agents are described herein. Proteins and peptides are described herein and may be used as a nanoparticle core, an additional agent, or both. In some embodiments, the additional agent is a chemotherapeutic agent.

The term "small molecule," as used herein, refers to a chemical compound or a drug, or any other low molecular weight organic compound, either natural or synthetic. By "low molecular weight" is meant compounds having a molecular weight of less than 1500 Daltons, typically between 100 and 700 Daltons.

REFERENCES

1. Mirkin, C. A.; Letsinger, R. L.; Mucic, R. C.; Storhoff, J. J., A DNA-based method for rationally assembling nanoparticles into macroscopic materials. Nature 1996, 382, 607.
2. Cutler, J. I.; Auyeung, E.; Mirkin, C. A., Spherical nucleic acids. J. Am. Chem. Soc. 2012, 134, 1376.
3. Choi, C. H.; Hao, L.; Narayan, S. P.; Auyeung, E.; Mirkin, C. A., Mechanism for the endocytosis of spherical nucleic acid nanoparticle conjugates. Proc. Natl. Acad. Sci. U.S.A 2013, 110, 7625.
4. Banga, R. J.; Chernyak, N.; Narayan, S. P.; Nguyen, S. T.; Mirkin, C. A., Liposomal spherical nucleic acids. J. Am. Chem. Soc. 2014, 136, 9866.
5. Radovic-Moreno, A. F.; Chernyak, N.; Mader, C. C.; Nallagatla, S.; Kang, R. S.; Hao, L.; Walker, D. A.; Halo, T. L.; Merkel, T. J.; Rische, C. H.; Anantatmula, S.; Burkhart, M.; Mirkin, C. A.; Gryaznov, S. M., Immunomodulatory spherical nucleic acids. Proc. Natl. Acad. Sci. U.S.A 2015, 112, 3892.
6. Guan, C.; Chernyak, N.; Dominguez, D.; Cole, L.; Zhang, B.; Mirkin, C. A., RNA-Based Immunostimulatory Liposomal Spherical Nucleic Acids as Potent TLR7/8 Modulators. Small 2018, 14, e1803284.
7. Ferrer, J. R.; Wertheim, J. A.; Mirkin, C. A., Dual Toll-Like Receptor Targeting Liposomal Spherical Nucleic Acids. Bioconjug. Chem. 2019, 30, 944.
8. Wang, S.; Qin, L.; Yamankurt, G.; Skakuj, K.; Huang, Z.; Chen, P. C.; Dominguez, D.; Lee, A.; Zhang, B.; Mirkin, C. A., Rational vaccinology with spherical nucleic acids. Proc. Natl. Acad. Sci. U.S.A 2019, 116, 10473.
9. Yamankurt, G.; Berns, E. J.; Xue, A.; Lee, A.; Bagheri, N.; Mrksich, M.; Mirkin, C. A., Exploration of the nanomedicine-design space with high-throughput screening and machine learning. Nat Biomed Eng 2019, 3, 318.
10. Jin, R.; Wu, G.; Li, Z.; Mirkin, C. A.; Schatz, G. C., What controls the melting properties of DNA-linked gold nanoparticle assemblies? J. Am. Chem. Soc. 2003, 125, 1643.
11. Xu, X.; Rosi, N. L.; Wang, Y.; Huo, F.; Mirkin, C. A., Asymmetric functionalization of gold nanoparticles with oligonucleotides. J. Am. Chem. Soc. 2006, 128, 9286.
12. Kim, Y.; Macfarlane, R. J.; Jones, M. R.; Mirkin, C. A., Transmutable nanoparticles with reconfigurable surface ligands. Science 2016, 351, 579.
13. Nam, J. M.; Stoeva, S. I.; Mirkin, C. A., Bio-bar-code-based DNA detection with PCR-like sensitivity. J. Am. Chem. Soc. 2004, 126, 5932.
14. Prigodich, A. E.; Lee, 0. S.; Daniel, W. L.; Seferos, D. S.; Schatz, G. C.; Mirkin, C. A., Tailoring DNA structure to increase target hybridization kinetics on surfaces. J. Am. Chem. Soc. 2010, 132, 10638.
15. Prigodich, A. E.; Randeria, P. S.; Briley, W. E.; Kim, N. J.; Daniel, W. L.; Giljohann, D. A.; Mirkin, C. A., Multiplexed nanoflares: mRNA detection in live cells. Anal. Chem. 2012, 84, 2062.
16. Ming, X.; Laing, B., Bioconjugates for targeted delivery of therapeutic oligonucleotides. Adv Drug Deliv Rev 2015, 87, 81.
17. Krieg, A. M., Therapeutic potential of Toll-like receptor 9 activation. Nat. Rev. Drug Discov. 2006, 5, 471.
18. Klinman, D. M., Immunotherapeutic uses of CpG oligodeoxynucleotides. Nat. Rev. Immunol. 2004, 4, 249.
19. Vollmer, J.; Weeratna, R.; Payette, P.; Jurk, M.; Schetter, C.; Laucht, M.; Wader, T.; Tluk, S.; Liu, M.; Davis, H. L.; Krieg, A. M., Characterization of three CpG oligodeoxynucleotide classes with distinct immunostimulatory activities. Eur. J. Immunol. 2004, 34, 251.
20. Blazar, B. R.; Krieg, A. M.; Taylor, P. A., Synthetic unmethylated cytosine-phosphate-guanosine oligodeoxynucleotides are potent stimulators of antileukemia responses in naive and bone marrow transplant recipients. Blood 2001, 98, 1217.
21. Ashley, C. E.; Carnes, E. C.; Phillips, G. K.; Padilla, D.; Durfee, P. N.; Brown, P. A.; Hanna, T. N.; Liu, J.; Phillips, B.; Carter, M. B.; Carroll, N. J.; Jiang, X.; Dunphy, D. R.; Willman, C. L.; Petsev, D. N.; Evans, D. G.; Parikh, A. N.; Chackerian, B.; Wharton, W.; Peabody, D. S.; Brinker, C. J., The targeted delivery of multicomponent cargos to cancer cells by nanoporous particle-supported lipid bilayers. Nat. Mater. 2011, 10, 389.
22. Irvine, D. J., Drug delivery: One nanoparticle, one kill. Nat. Mater. 2011, 10, 342.
23. Kerkmann, M.; Costa, L. T.; Richter, C.; Rothenfusser, S.; Battiany, J.; Hornung, V.; Johnson, J.; Englert, S.; Ketterer, T.; Heckl, W.; Thalhammer, S.; Endres, S.; Hartmann, G., Spontaneous formation of nucleic acid-based nanoparticles is responsible for high interferon-alpha induction by CpG-A in plasmacytoid dendritic cells. J. Biol. Chem. 2005, 280, 8086.
24. de Titta, A.; Ballester, M.; Julier, Z.; Nembrini, C.; Jeanbart, L.; van der Vlies, A. J.; Swartz, M. A.; Hubbell, J. A., Nanoparticle conjugation of CpG enhances adjuvancy for cellular immunity and memory recall at low dose. Proc. Natl. Acad. Sci. U.S.A 2013, 110, 19902.
25. Basu, S.; Wickstrom, E., Temperature and salt dependence of higher order structure formation by antisense c-myc and c-myb phosphorothioate oligodeoxyribonucleotides containing tetraguanylate tracts. Nucleic Acids Res. 1997, 25, 1327.
26. Förster, T., Zwischenmolekulare Energiewanderung und Fluoreszenz. Annalen der Physik 2006, 437, 55.
27. Meckes, B.; Banga, R. J.; Nguyen, S. T.; Mirkin, C. A., Enhancing the Stability and Immunomodulatory Activity of Liposomal Spherical Nucleic Acids through Lipid-Tail DNA Modifications. Small 2018, 14, 1702909.
28. Dearman, R. J.; Cumberbatch, M.; Maxwell, G.; Basketter, D. A.; Kimber, I., Toll-like receptor ligand activation of murine bone marrow-derived dendritic cells. Immunology 2009, 126, 475.
29. Lee, B. L.; Barton, G. M., Trafficking of endosomal Toll-like receptors. Trends Cell Biol. 2014, 24, 360.
30. Majer, O.; Liu, B.; Barton, G. M., Nucleic acid-sensing TLRs: trafficking and regulation. Curr. Opin. Immunol. 2017, 44, 26.
31. Schwartz, R. H., A cell culture model for T lymphocyte clonal anergy. Science 1990, 248, 1349.
32. Lancaster, G. I.; Khan, Q.; Drysdale, P.; Wallace, F.; Jeukendrup, A. E.; Drayson, M. T.; Gleeson, M., The physiological regulation of toll-like receptor expression and function in humans. J Physiol 2005, 563, 945.
33. June, C. H.; Bluestone, J. A.; Nadler, L. M.; Thompson, C. B., The B7 and CD28 receptor families. Immunol. Today 1994, 15, 321.
34. Madaan, A.; Verma, R.; Singh, A. T.; Jain, S. K.; Jaggi, M., A stepwise procedure for isolation of murine bone marrow and generation of dendritic cells. Journal of Biological Methods 2014, 1, el.
35. Borlinghaus, R. T.; Kappel, C., HyVolution—the smart path to confocal super-resolution. Nat. Methods 2016, 13, I.
36. Manders, E. M.; Stap, J.; Brakenhoff, G. J.; van Driel, R.; Aten, J. A., Dynamics of three-dimensional replication patterns during the S-phase, analysed by double labelling of DNA and confocal microscopy. J. Cell Sci. 1992, 103, 857.
37. Manders, E. M. M.; Verbeek, F. J.; Aten, J. A., Measurement of co-localization of objects in dual-colour confocal images. J. Microsc. 1993, 169, 375.

The following examples are given merely to illustrate the present disclosure and not in any way to limit its scope.

EXAMPLES

The following examples describe the synthesis and evaluation of spherical nucleic acids (SNAs) incorporating two physically and chemically distinct classes of oligonucleotides (ODNs) at programmed ratios. These SNAs are single entity agents that entered the same target cell at defined stoichiometries, and as such allow one to control important cell signaling and regulatory processes. To study the effect of sequence multiplicity within such structures, SNAs were synthesized consisting of a mixture of class A CpG and class B CpG, immunostimulatory ODNs that activate two different toll-like receptor 9 (TLR9) signaling pathways, each in a sequence-specific fashion. These dual-CpG SNAs exhibited high cellular uptake and co-delivery of the two ODNs, relative to mixtures of the linear ODN counterparts, and remained highly associated inside the cell over time. Furthermore, the dual-CpG SNAs augmented dendritic cell (DC) maturation, compared to the same amounts of oligonucleotides delivered in linear or SNA form but not conjugated to one another. Consequently, these structures constitute a platform for designing oligonucleotide-based combination therapeutics with highly tailorable activities.

The studies presented herein incorporate two physically- and chemically-distinct oligonucleotide sequences with onto the same SNA construct in controlled ratios. The resulting SNAs showed strong intracellular association of the two oligonucleotide sequences over extended periods of time, sequence-independent intracellular trafficking, and sequence- and ratio-dependent downstream activations, in addition to the known advantageous SNA properties of superior cellular uptake and enhanced activation as compared to their linear counterparts. The findings described herein provide vital insights about the design of SNAs as a platform for the delivery of multifunctional therapeutics.

To study the effect of sequence multiplicity within such structures, SNAs consisting of two physically (e.g., structural features) and chemically (e.g., backbone chemistry) distinct oligonucleotide sequences were synthesized with class A CpGs and class B CpGs, which are immunostimulatory ODNs that activate two different toll-like receptor 9 (TLR9) signaling pathways, each in a sequence-specific fashion. These dual-CpG SNAs exhibited high cellular uptake and co-delivery of the two ODNs, relative to mixtures of the linear ODN counterparts, and remained highly associated inside the cell over time. Furthermore, the dual-CpG SNAs augmented dendritic cell maturation, compared to the same amounts of oligonucleotides delivered in linear or SNA form but not conjugated to one another. Consequently, these structures constitute a platform for designing oligonucleotide-based combination therapeutics with highly tailorable activities.

Delivering multiple entities on the same particle to immune cells is beneficial over administration of simple mixtures of the individual components, because the nanoparticle scaffold allows for delivery of programmed ratios of each component to the same target cell.[21-22] In this study, two physically (e.g., structural features) and chemically (e.g., backbone chemistry) distinct oligonucleotide sequences, CpG-A (ODN 1585) and CpG-B (ODN 1826), were incorporated into LSNAs (FIG. 1) to study the intracellular trafficking of the SNAs and their downstream activation of DCs.

Example 1

Materials and Methods 1,2-dioleoyl-sn-glycero-3-phosphocholine (DOPC) was purchased from Avanti Polar Lipids as a solution in chloroform. TLR9 ligands CpG ODN 1585 (Class A), 1826 (Class B), and their corresponding GpC control sequences were synthesized on an ABI 3900 DNA oligo synthesizer with all reagents purchased from Glen Research (See below).

Synthesis of oligionucleotides. Oligonucleotides were synthesized using an ABI 3900 DNA oligo synthesizer on a standard controlled pore glass (GPG) solid phase support following the manufacturer's protocol. All modified phosphoramidites were purchased from Glen Research. The products were purified by reverse phase high-performance liquid chromatography (HPLC). Syntheses were verified by matrix-assisted laser desorption/ionization-time-of-flight mass spectrometry (MALDI-TOF), and the concentrations were determined by UV-visible spectroscopy. A complete list of oligonucleotides synthesized can be found in Table 1.

µg/mL Zeocin (InvivoGen). Reagents for reporter cell line assays (Quanti-Blue and Quanti-Luc) were also purchased from InvivoGen.

Preparation of liposomal SNAs (LSNAs). In a typical synthesis, 4 mL of a chloroform solution of DOPC lipid (25 mg/mL) was transferred into a glass vial, and the lipid dried

TABLE 1

List of oligonucleotide sequences used herein.

| Strand | DNA sequence from 5' to 3 | SEQ ID NO: |
|---|---|---|
| ODN 1585 (CpG-A)-chol | ggGGTCAACGTTGAgggggg-(Sp18)$_2$-chol | 2 |
| ODN 1826 (CpG-B)-chol | tccatgacgttcctgacgtt-(Sp18)$_2$-chol | 3 |
| Linear CpG-A | ggGGTCAACGTTGAgggggg | 4 |
| Linear CpG-B | tccatgacgttcctgacgtt | 5 |
| Fluorescein-CpG-A-chol | ggGGTCAACGTTGAgggggg-(Sp18)-FAM-(Sp18)-chol | 6 |
| Cy3-CpG-B-chol | tccatgacgttcctgacgtt-(Sp18)-Cy3-(Sp18)-chol | 7 |
| Cy5-CpG-B-chol | tccatgacgttcctgacgtt-(Sp18)-Cy5-(Sp18)-chol | 8 |
| Linear fluorescein-CpG-A | ggGGTCAACGTTGAgggggg-FAM | 9 |
| Linear Cy5-CpG-B | tccatgacgttcctgacgtt-Cy5 | 10 |

Notations and abbreviations:
1. Upper-case letter bases denote phosphodiester backbone, and lower-case letter bases denote phosphorothioate backbone. Underlined portion indicates palindrome.
2. "chol" refers to 1-dimethoxytrityloxy-3-O-(N-cholesteryl-3-aminopropyl)-triethylenegly-col-glyceryl-2-O-succinoyl-long chain alkylamino-CPG (3'-Cholesteryl-TEG CPG).
3. "Sp18" refers to 18-O-dimethoxytritylhexaethyleneglycol,1-[(2-cyanoethyl)-(N,N-diisopropyl)]-phosphoramidite (Spacer phosphoramidite 18).
4. "FAM" refers to 1-dimethoxytrityloxy-2-(N-thiourea-(di-O-pivaloyl-fluorescein)-4-aminobutyl)-propyl-3-O-(2-cyanoethyl)-(N,N-diisopropyl)-phosphoramidite (Fluorescein phosphoramidite).
5. "Cy3" refers to 1-[3-(4-monomethoxytrityloxy)propyl]-1'-[3-[(2-cyanoethyl)-(N,N-diisopropyl) phosphoramidityl]propyl]-3,3,3',3'-tetramethylindocarbocyanine chloride (Cyanine 3 phosphoramidite).
6. "Cy5" refers to 1-[3-(4-monomethoxytrityloxy)propyl]-1'-[3-[(2-cyanoethyl)-(N,N-diisopropyl) phosphoramidityl]propyl]-3,3,3',3'-tetramethylindodicarbocyanine chloride (Cyanine 5 phosphoramidite).

Cell lines. Bone marrow-derived dendritic cells (BMDCs) were collected from C57BL/6 wildtype mice and processed following the literature protocol[34], and the cells were cultured in RPMI 1640 medium (Gibco) supplemented with 10% fetal bovine serum (FBS, Atlanta Biologicals), 100 U/mL penicillin-streptomycin (pen-strep, Gibco), and 20 ng/mL recombinant mouse granulocyte-macrophage colony stimulating factor (GM-CSF, eBioScience). JAWSII, an immortal murine BMDC cell line, was purchased from ATCC (CRL-11904) and cultured in alpha minimum essential medium (Gibco) supplemented with 1 mM sodium pyruvate (Gibco), 5 ng/mL GM-CSF, 20% FBS, and 100 U/mL pen-strep. RAW Dual cells, a RAW 264.7 murine macrophage reporter cell line for IRF and nuclear factor κB (NF-κB), was purchased from InvivoGen and cultured in Dulbecco's Modified Eagle Medium, 10% FBS, 100 U/mL pen-strep, 100 µg/mL Normocin (InvivoGen), and 200 under nitrogen gas for 30 minutes and stored in vacuo overnight to completely remove organic solvent and generate a thin lipid film. The film was then rehydrated in 10 mL of PBS. The resulting suspension was vortexed for 30 seconds and sonicated for 30 minutes. Following five freeze-thaw cycles, the suspension underwent serial extrusions in 200-nm, 100-nm, 80-nm, and 50-nm track-etch membranes to obtain uniform-size liposomes. Liposomes were concentrated using 50K MWCO MicroKros tangential flow filtration (Spectrum Labs), and the final concentration was measured using the phosphatidylcholine assay kit (Sigma). To functionalize oligonucleotides onto the surface of liposomes, 100 µM 3'-cholesterol-functionalized oligonucleotides were mixed with a predetermined amount of liposomes, calculated following Table 2. Samples were held overnight at 37° C. under shaking at 500 rpm. Formulation of CpG and dual-CpG SNAs is shown in Table 2.

TABLE 2

Dual-CpG SNA composition.

| Sample # | CpG-A mol % | CpG-A: liposome (µM/µM) | CpG-A conc. (µM) | CpG-B mol % | CpG-B: liposome (µM/µM) | CpG-B conc. (µM) | liposome conc. (µM) |
|---|---|---|---|---|---|---|---|
| 1 | 100% | 150 | 100 | 0% | 0 | 0 | 0.667 |
| 2 | 90% | 135 | 90 | 10% | 7.5 | 10 | 0.733 |
| 3 | 70% | 105 | 70 | 30% | 22.5 | 30 | 0.867 |
| 4 | 50% | 75 | 50 | 50% | 37.5 | 50 | 1.000 |

TABLE 2-continued

Dual-CpG SNA composition.

| Sample # | CpG-A mol % | CpG-A: liposome (μM/μM) | CpG-A conc. (μM) | CpG-B mol % | CpG-B: liposome (μM/μM) | CpG-B conc. (μM) | liposome conc. (μM) |
|---|---|---|---|---|---|---|---|
| 5 | 30% | 45 | 30 | 70% | 52.5 | 70 | 1.133 |
| 6 | 10% | 15 | 10 | 90% | 67.5 | 90 | 1.267 |
| 7 | 0% | 0 | 0 | 100% | 75 | 100 | 1.333 |

Materials characterization. To assess CpG-A incorporation into SNAs, agarose gel electrophoresis was performed using 1% agarose (Sigma) with SYBR Safe DNA gel stain in 0.5× Tris/Borate/EDTA (TBE) (ThermoFisher Scientific) under 120 V for 1 hour. To assess dual-CpG loading, fluorophore-labeled oligonucleotides (FAM-CpG-A and Cy5-CpG-B) were used, and agarose gel electrophoresis was performed using 0.5% agarose in 1×TBE without further staining. Dynamic light scattering (DLS) and zeta potential measurements were performed using a Malvern Zetasizer Nano with approximately 10 nM samples by particle. Cryogenic transmission electron microscopy (CryoTEM) was performed with a Hitachi HT7700 TEM with a Gatan cryo-transfer holder, and imaging was performed under a 120-kV accelerating voltage. CryoTEM samples were prepared by loading 4 μL of sample (100 μM CpG SNA stock solution or 1.33 μM liposome solution) onto 300-mesh copper TEM grids with lacey carbon films (Electron Microscopy Sciences) using a FEI Vitrobot Mark IV with its chamber equilibrated at 4° C. and 100% humidity. The samples were blotted for 5 s and plunged into liquid ethane before they were transferred and stored in liquid nitrogen. Förster resonance energy transfer (FRET) measurements were performed using a Synergy plate reader (Biotek) with 10 nM samples by oligonucleotides. FRET efficiency was calculated as:

$$E = 1 - \frac{F_{DA}}{F_D}$$

where $F_{DA}$ and $F_D$ are the donor fluorescence intensities with and without an acceptor, respectively.

Confocal microscopy and image analysis. $2 \times 10^4$ JAWSII cells in 0.5 mL cell phenol red-free culture medium were plated on gelatin-coated 15-mm coverslips in 24-well plates overnight and incubated with 5 μM SNA by CpG oligonucleotide concentration. Fluorescein-labeled CpG-A ODN and/or Cy5-labeled CpG-B ODN were used, and the high concentration was used to ensure detectable signal after a prolonged time. To track the same amount of SNAs trafficking over time, all cells were treated for 30 minutes. For the 30 minute time points in the intracellular trafficking studies, cells were incubated with media containing either SNAs or linear CpG ODNs for 30 minutes, then washed, removed from media, fixed, and stained. For all other time points, cells were incubated in SNA or CpG-containing media for 30 minutes, washed twice, and incubated with fresh media for the additional amount of time prior to fixation and staining. At the end of the treatment, coverslips were incubated in 4% paraformaldehyde in PBS (diluted from a 32% aqueous solution from Electron Microscopy Sciences) for 15 minutes for fixation and 0.2% Triton-X in PBS (diluted from Triton-X from Sigma) for 10 minutes for permeation.

Figure 2:
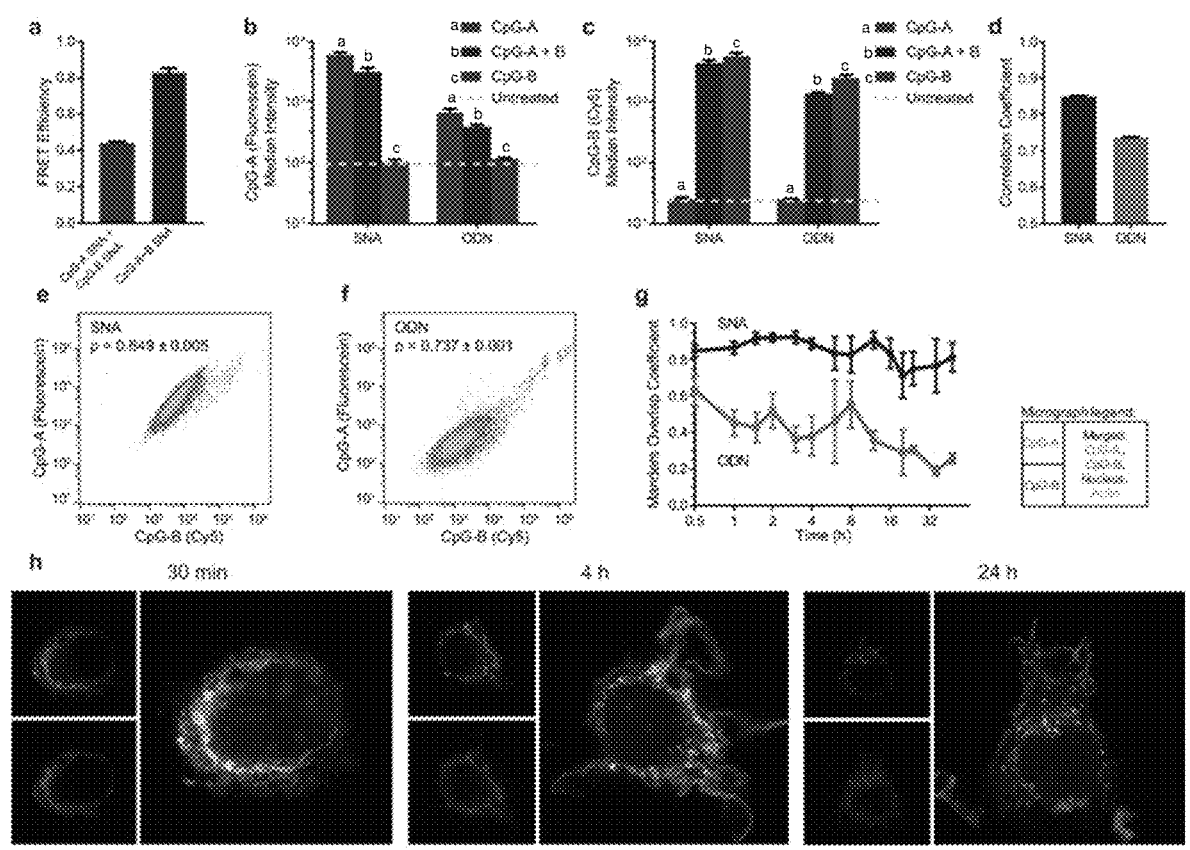
FIG. 2 shows the characterization of dual-CpG SNAs (50:50 mol ratio CpG-A to CpG-B). (a) FRET efficiency comparison between FAM-CpG-A SNA/Cy3-CpG-B SNA mixture and dual-CpG SNA. Fluorescence signals of (b) FAM-CpG-A and (c) Cy5-CpG-B after 30-minute treatments in single-component or dual-CpG form. (d) Pearson correlation coefficient (p) between CpG-A and CpG-B uptake in dual-CpG SNA and linear CpG mixture forms. Representative flow cytometry data of (e) dual-CpG SNA and (f) linear CpG mixture uptake. (g) Manders overlap coefficients between CpG-A and CpG-B in dual-CpG SNA and linear CpG mixture forms over time after cellular uptake. (h) Representative confocal microscopy images of dual-CpG SNA 30 minutes, 4 hours, and 24 hours after initial uptake. All dual-CpG data shown in this figure incorporated a 1:1 ratio of CpG-A:CpG-B.

For the CpG association study (FIG. 2), the cells were incubated in Image-iT™ FX Signal Enhancer (ThermoFisher Scientific) for 30 minutes and then in Alexa Fluor 568 Phalloidin for 30 minutes. Phalloidin labels the actin of the cytoskeleton, which here serves as the confirmation of DC structure (the dendrite growth over time may also serve as confirmation of dendritic cell maturation, though it is difficult to quantify). For the intracellular trafficking study, coverslips were incubated in 2% bovine serum albumin (BSA) and 0.2% Triton-X in PBS for 1 hour for blocking. Rabbit anti-EEA1 (ABclonal), rabbit anti-Rab9 (Abclonal), rabbit anti-LAMP1 (Abcam), and rabbit anti-LC3 (Sigma-Aldrich) primary antibodies diluted 1:1000 in 1% BSA, 0.1% Triton-X in PBS were used for early endosome, late endosome, lysosome, and autophagosome labeling, respectively. Alexa Fluor 568-labeled goat anti-rabbit IgG H&L secondary antibody (Abcam) diluted 1:1000 in 1% BSA, 0.1% Triton-X in PBS was used to fluorescently tag the intracellular organelle markers. All treatment and staining steps used 0.4 mL volumes, and coverslips were washed twice using 1 mL PBS or thrice using PBS-Triton-X (for antibody washes) after each step. After staining, coverslips were mounted onto glass slides using ProLong Glass with NucBlue nuclear stain (ThermoFisher Scientific) and cured overnight. Confocal microscopy was performed using Leica TCS SP8 LSCM with hybrid detectors (HyD) and HyVolution.[35]

Data processing and colocalization calculations were performed using the Leica Application Suite X (for HyVolution) and an in-house Matlab script. A total of 25 cells were included for the analysis for each sample. Images of individual detection channels were exported as grayscale maps and denoised using deep neural network. Z-stack layers of whole cells were arranged into a three-dimensional array as pseudo-3D reconstruction of the cell image for each channel. Colocalization analysis provides a quantitative means to evaluate the qualitative confocal image data. Manders overlap and colocalization coefficients[36-37] were used in this study to analyze the colocalization of color pairs from the confocal images. For analyzing the association of the two CpG ODNs, the Manders overlap coefficient, a parameter describing the degree of overlap between two components in an image, was calculated. The Manders overlap coefficient, a derivative of the Pearson's correlation coefficient, is defined as:

$$r = \frac{\sum_i a_i \cdot b_i}{\sqrt{\sum_i (a_i)^2 \cdot \sum_i (b_i)^2}}$$

where $a_i$ and $b_i$ are the grey-scale values of the individual voxels i of the color components a and b, which in this case, were the fluorescein and Cy5 signals. For analysis of colocalization of CpG ODN in the organelles, the Manders colocalization coefficient was used which is defined by:

$$M_{ab} = \frac{\sum_i a_{i,b_i>0}}{\sum_i a_i}$$

so that Mab measures the fluorescence fraction of a colocalized with b, which in this case was the ODN signal (fluorescein and/or Cy5) colocalized in the organelle (Alexa Fluor 568). This coefficient was useful since it does not consider the pixels of the second signal (organelles) that do not overlap with the first signal (ODN). Both Manders overlap and colocalization coefficients are signal intensity independent, which made them advantageous in this study to compare markers that may have different signal intensities caused by different uptake amount (SNA vs. linear oligonucleotides), CpG signal decrease over time, and difference in organelle antibody labeling.

Flow Cytometry. All antibodies and staining buffers were purchased from BD Biosciences, and all antibodies were mixed and diluted to 1:200 in staining buffer. For the uptake study, $3 \times 10^5$ cells were treated with fluorescein-labeled CpG-A and/or Cy5-labeled CpG-B oligonucleotides with a total oligonucleotide concentration of 1 µM in 1.2 mL microtubes. After a 30-minute incubation at 37° C., cells were washed three times with 1 mL PBS and stained with 100 µL of antibody solution containing rat anti-mouse CD11b and hamster anti-mouse CD11c. Pearson correlation calculations were performed using fluorescein (G) and Cy5 (R) signals of each cell into the formula:

$$\rho(G, R) = \frac{1}{N-1} \sum_{i=1}^{N} \left( \frac{G_i - \mu_G}{\sigma_G} \right) \left( \frac{R_i - \mu_R}{\sigma_R} \right)$$

where $\mu_G$ and $\sigma_G$ are the mean and standard deviation of G, respectively, and $\mu_R$ and $\sigma_R$ are the mean and standard deviation of R, respectively. For the dendritic cell activation study, $3 \times 10^5$ cells were incubated with 200 µL of 1 µM CpG (linear or SNA) containing media for 24 hours in 1.2 mL microtubes. The cells were then washed three times with 1 mL PBS and stained with 100 µL of antibody solution containing rat anti-mouse CD11b, hamster anti-mouse CD11c, hamster anti-mouse CD80, and rat anti-mouse CD86 for 15 minutes at 4° C. The cells were then fixed with 3.7% paraformaldehyde in PBS for 20 minutes at room temperature. Flow cytometry was completed with a BD LSRFortessa flow cytometer system. 30,000 events were collected for each sample, and DCs gated with CD11c+ population. Color compensation was performed using the AbC total antibody compensation bead kit (ThermoFisher Scientific). Data analysis was performed using FlowJo and Matlab.

Cytokine and IFN measurements. Cytokine and IFN release were measured using Luminex 200. Assays were performed using mouse magnetic Luminex assay kits purchased from R&D Systems for cytokines and ThermoFisher Scientific for IFN-α. $2 \times 10^5$ cells were treated with 200 µL media containing 100 nM CpG (linear or SNA) in a round-bottom 96-well plate for 24 hours, and after centrifugation for 5 minutes at 1,000 rpm, the cell supernatants were collected and transferred to the Luminex assay plate without further dilution. Sample processing and measurements were performed following the manufacturer's specific protocols. Data analysis was performed using Milliplex Analyst software.

Results and Discussion

Figure 3:
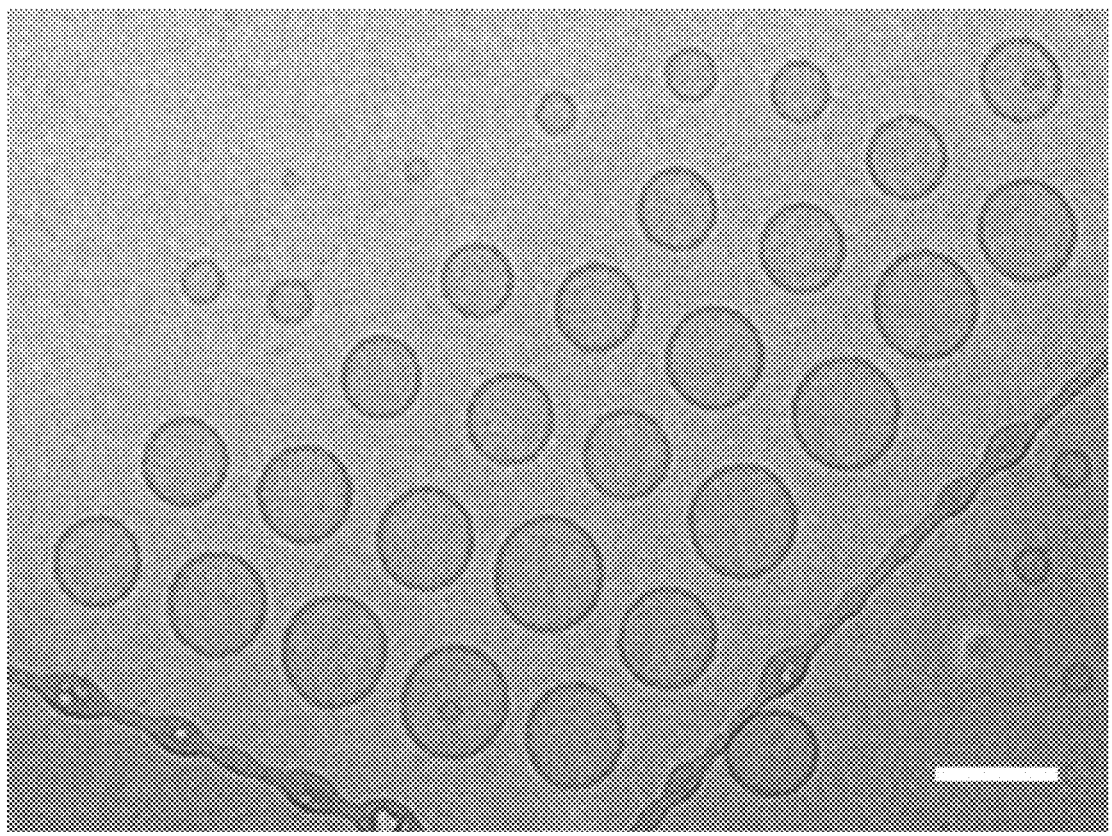
FIG. 3 shows a CryoTEM image of LSNAs functionalized with 75 equivalents of class B CpG oligodeoxynucleotide (ODN). Scale bar: 100 nm.
Figure 4:
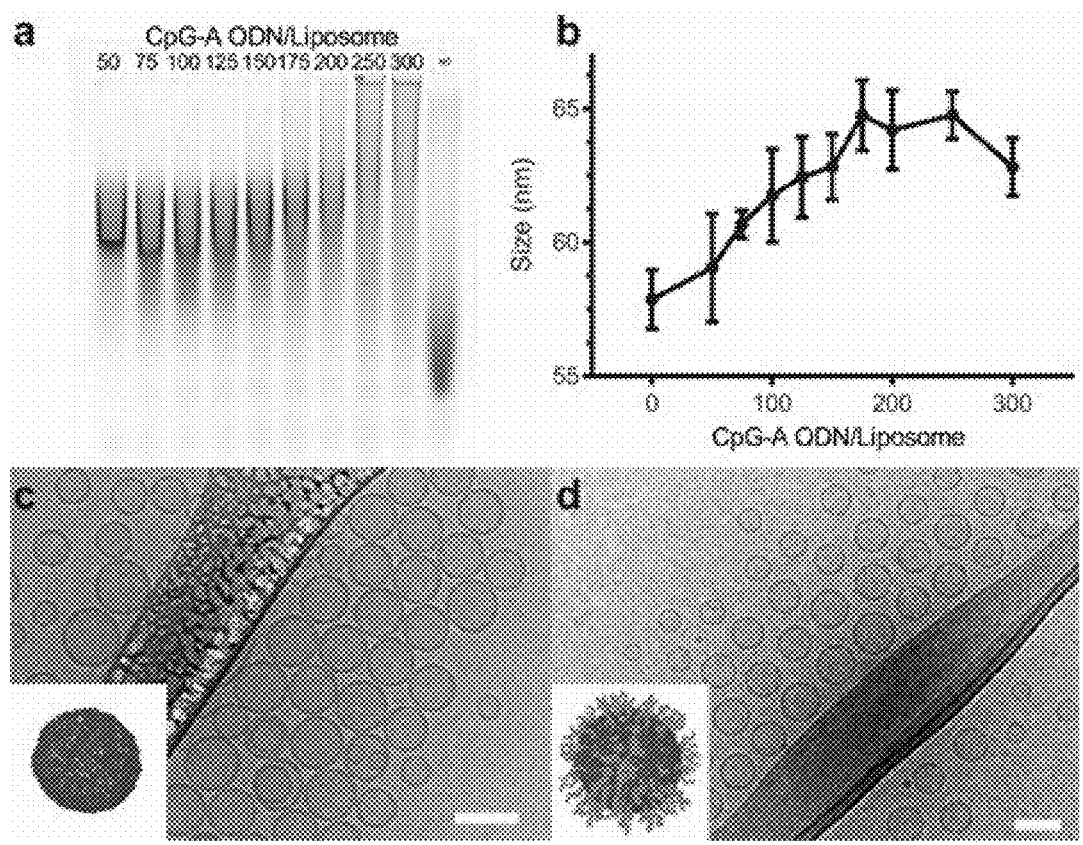
FIG. 4 shows the characterization of CpG-A SNAs. (a) Agarose gel electrophoresis of liposomes functionalized with different amounts of cholesterol-labeled CpG-A ODN; the symbol ∞ indicates free cholesterol-labeled CpG-A ODN. (b) Hydrodynamic size of CpG-A SNAs as measured by DLS. CryoTEM images of: (c) bare liposomes and (d) SNAs functionalized with 150 CpG-A ODN. Scale bars: 100 nm.
Figure 5:
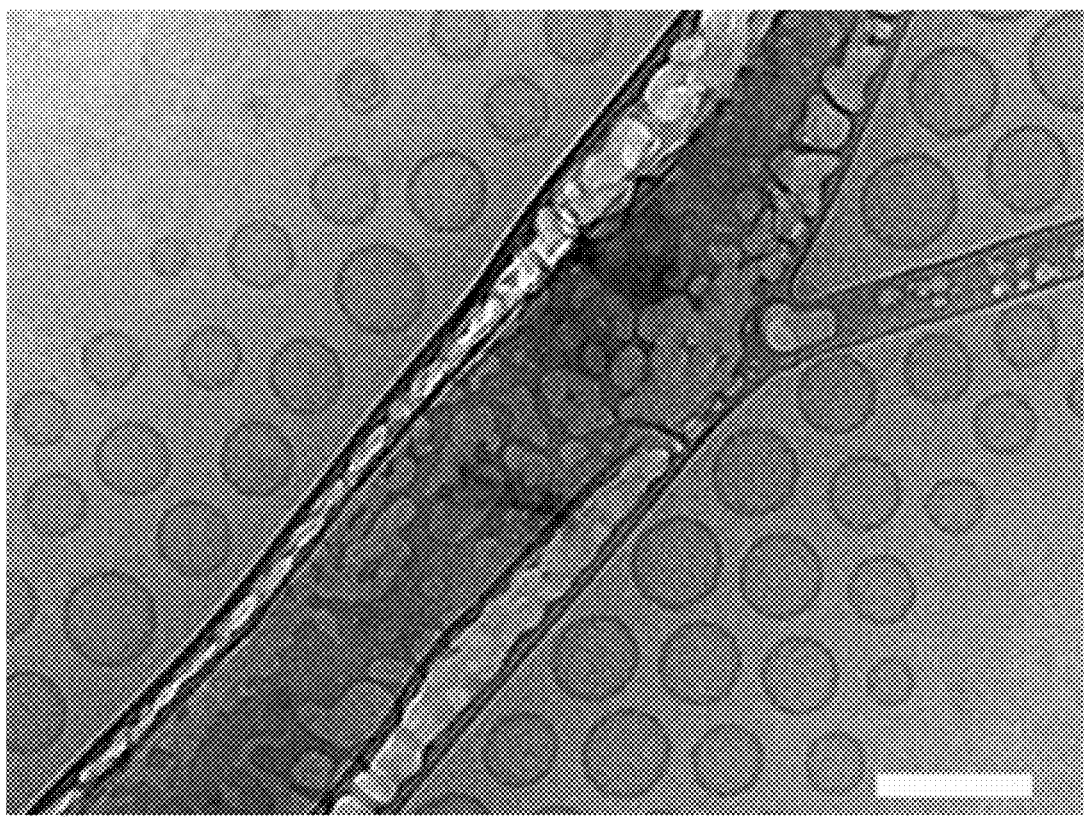
FIG. 5 shows a CryoTEM image of LSNAs functionalized with 50 equivalents of class A CpG ODN. Scale bar: 100 nm.
Figure 19:
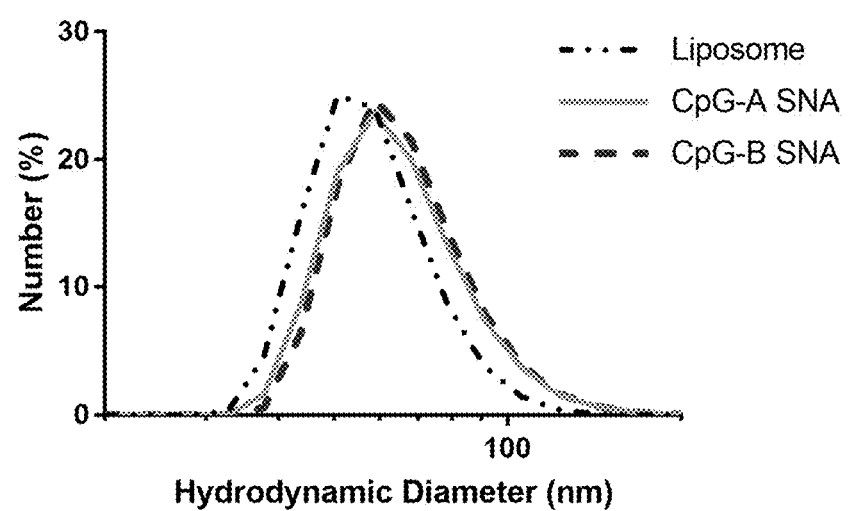
FIG. 19 shows DLS characterization of liposomes and LSNAs.

To generate SNAs, 3'-cholesterol-terminated oligonucleotides and 50-nm 1,2-dioleoyl-sn-glycero-3-phosphocholine (DOPC) liposomes were mixed in a predetermined ratio to achieve the desired CpG ODN loading on the SNA scaffold.[4, 8] First, single-component SNAs, comprised of either all CpG-A or all CpG-B DNA, were synthesized and characterized to understand the impact of sequence and secondary DNA structure on the DNA loading of SNAs. In particular, CpG-B SNAs (FIG. 3) have been well-characterized and studied as cancer immunotherapeutics with a maximal loading of 75 CpG-B ODN per 50 nm liposome.[5, 8-9] Conversely, CpG-A ODN has been proposed to have nanoparticle-like properties because it contains a poly(G) sequence that forms G-quadruplexes that can potentially stabilize the palindrome sequence.[23-24] Thus, CpG-A is rarely incorporated into nanomaterials and has never been used as a component of SNAs. However, these higher-order structures of CpG-A are salt- and temperature-dependent;[23, 25] thus, it was hypothesized that CpG-A aggregation could be circumvented by incorporating CpG-A into SNAs during the SNA assembly process (as is shown herein). Therefore, the oligonucleotide content of CpG-A in SNAs was first studied and it was determined through agarose gel electrophoresis that up to 150 cholesterol-terminated CpG-As could be inserted into 50-nm DOPC liposomes (FIG. 4a). This observation was confirmed by the size increase trend, as function of oligonucleotide equivalents, determined by dynamic light scattering (DLS, FIGS. 4b and 19). Cryogenic transmission electron microscopy (CryoTEM) analysis revealed that unfunctionalized liposomes pack tightly together, presumably due to the absence of negatively charged surface ligands and therefore minimized electrostatic repulsion between particles (FIG. 4c). However, when the liposomes were transformed into SNAs through their external modification with CpG-A, there was a marked increase in interparticle spacing (FIG. 4d), a trend that was also observed with CpG-B liposomal SNAs (FIG. 3). For example, CpG-A SNA interparticle spacing increased with increased oligonucleotide loading from 21.0±3.5 nm (50 strands/SNA, FIG. 5) to 27.7±3.7 nm (150 strands/SNA, FIG. 4d). These results not only showed that higher oligonucleotide loading density lead to higher particle surface coverage, but also created more radially oriented ODNs within the SNA structure. When the DNA: liposome ratio exceeded 150:1, an upward shift in mobility by gel electrophoresis was observed (FIG. 4a), indicating a significant size increase in the population, presumably due to aggregation of the SNAs caused by sequence self-complementarity (as discussed herein below). To avoid aggregation-specific effects on cellular uptake and downstream immune activation, SNAs incorporating 150 strands of CpG-A ODN per particle were used in further studies.

Figure 6:
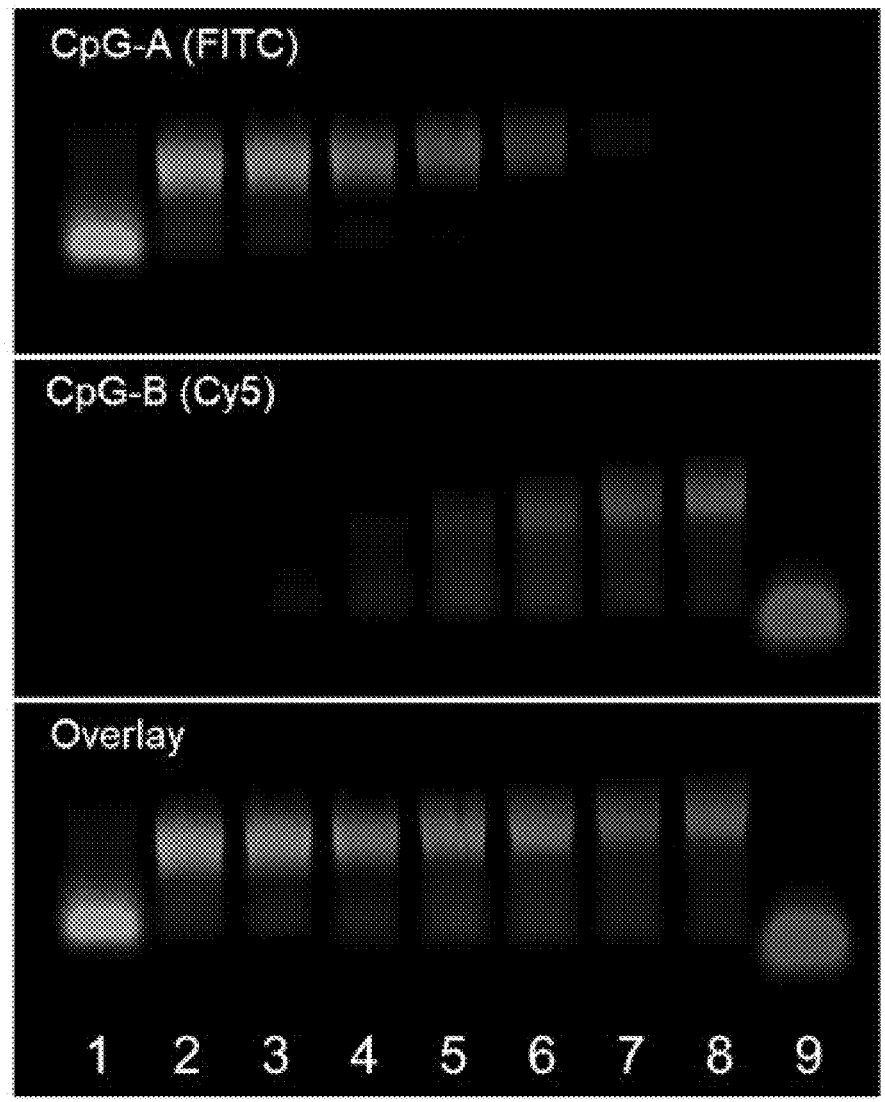
FIG. 6 shows an agarose gel showing CpG components in dual-CpG SNAs. Lanes from left to right: 1: free CpG-A, 2: CpG-A SNA, 3-7: 10%, 30%, 50%, 70%, and 90% dual-CpG SNAs, 8: CpG-B SNA, 9: free CpG-B.
Figure 7:
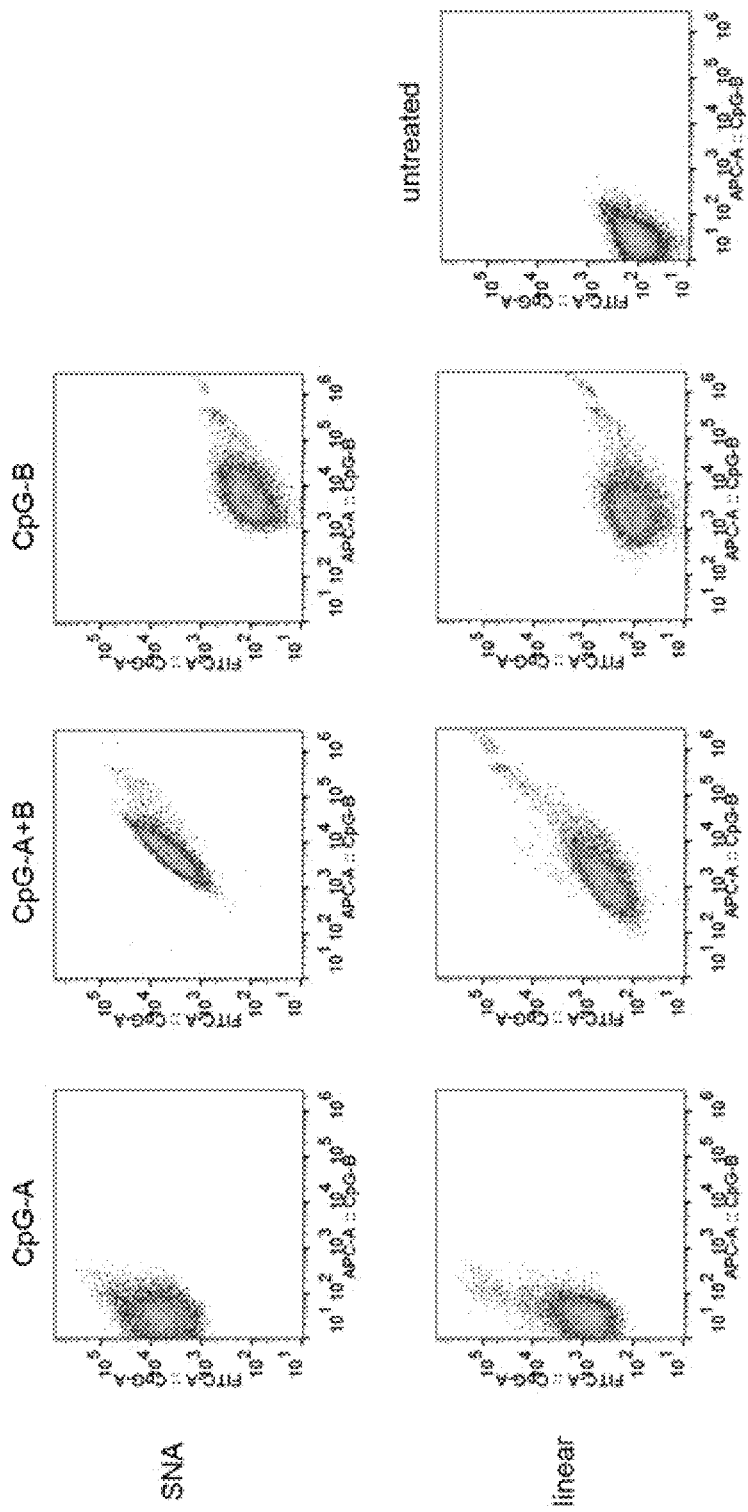
FIG. 7 shows representative flow cytometry data of SNA and linear CpG mixture uptake after 30 minutes of treatment.
Figure 20:
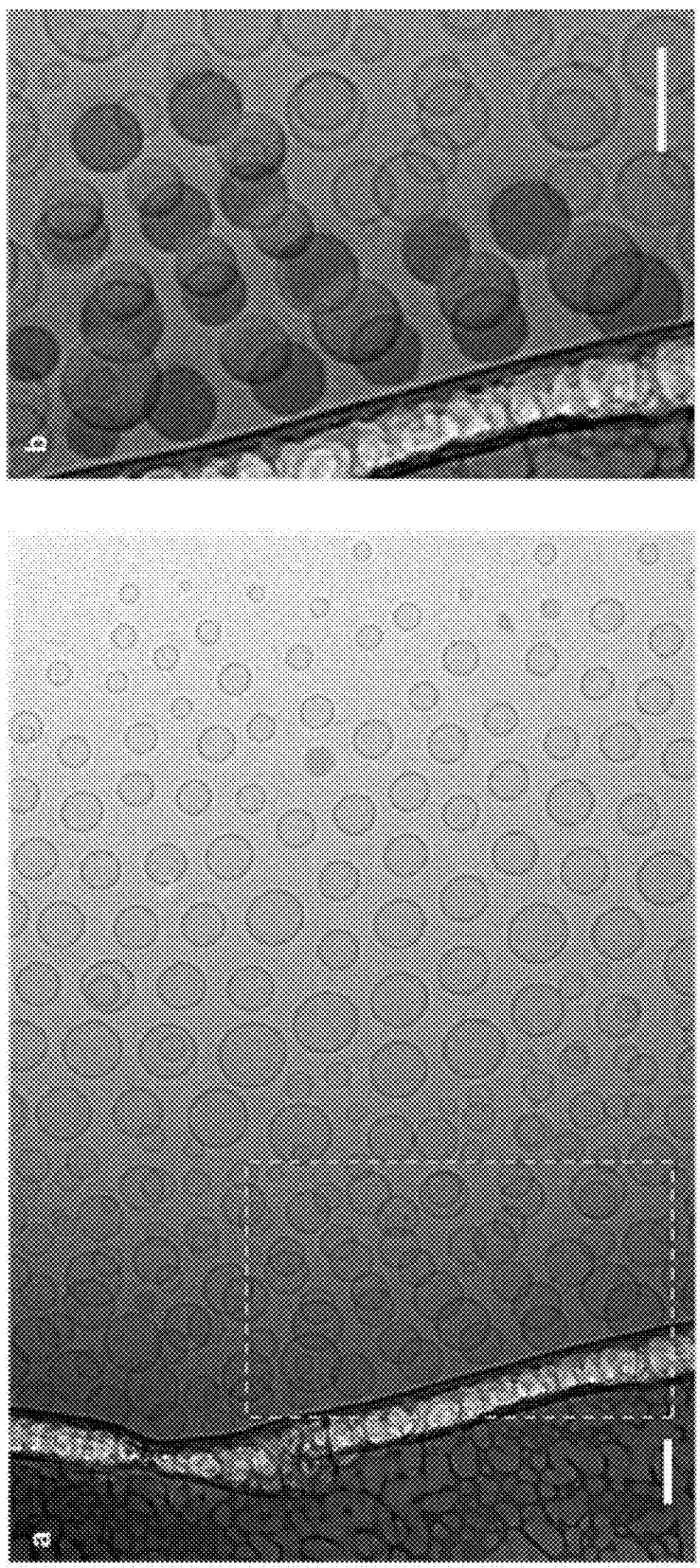
FIG. 20 shows a CryoTEM image of mixed-CpG SNAs packed in two layers. Scale bars: 100 nm. (b) shows a zoomed in-view of the boxed portion with false color to show the layered structure.

SNAs incorporating both classes of CpG ODN on the same nanoparticle scaffold were next synthesized by incorporating CpG-A and CpG-B into unfunctionalized DOPC liposomes at defined ratios (Table 2), based on the determined saturation limits of each single-component SNA. Agarose gel electrophoresis revealed that both CpG classes were incorporated into SNAs (FIG. 6). To confirm the successful dual functionalization of SNAs with both CpG ODN, Förster resonance energy transfer (FRET), the energy transfer process from one excited fluorophore to an acceptor fluorophore (such as from fluorescein to Cy3) when donor and acceptor are within the Förster radius, was employed.[26-27] Dual-CpG SNAs functionalized with 50% fluorescein-labeled CpG-A and 50% Cy3-labeled CpG-B showed a significantly higher FRET efficiency as compared to a 50:50 mixture of two distinct sets of SNAs, each incorporating one fluorophore-labeled class of CpG ODN (FIG. 2a). Such significantly higher FRET efficiency indicated that the two CpG ODN classes were in closer proximity when functionalized on the same SNA compared to when they were functionalized on separate SNAs, reflecting successful dual sequence functionalization on the same SNA. The dual-CpG SNAs were also evaluated by CryoTEM analysis (FIG. 20).

Figure 8:
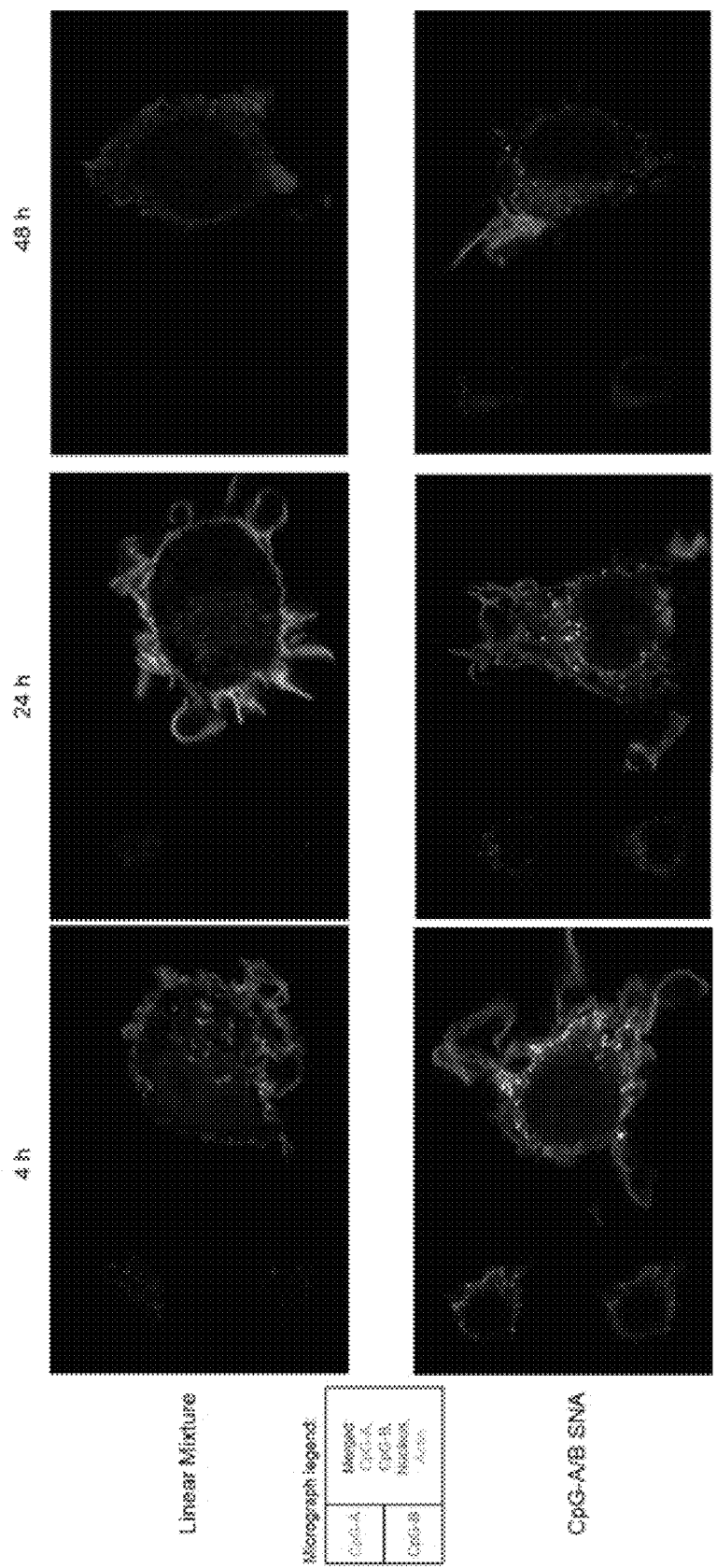
FIG. 8 shows representative confocal microscopy images of linear CpG mixture and dual-CpG SNA at different time points.

To evaluate the uptake and immunogenicity of dual-CpG SNAs, mouse bone marrow-derived dendritic cells (DCs), a TLR9-presenting cell line widely utilized for in vitro immune stimulation studies using CpG ODNs, were used as a model system.[28] DCs incubated with SNAs showed significantly higher uptake as compared to cells treated with linear ODNs (FIG. 2b-c) after 30 minutes. Dual-CpG SNAs showed similar uptake to SNAs functionalized with a single class of CpG ODN (FIGS. 2b-c and 7) on a per particle basis. As expected, the fluorescence of cells treated with dual-CpG SNAs incorporating fluorescein-labeled CpG-A and Cy5-labeled CpG-B at a 50:50 mol ratio was roughly half the intensity of cells treated with single-component SNAs, as each CpG component encompassed half of the total CpG ODN incorporated into the dual-CpG SNA scaffold. Furthermore, cells treated with 50:50 dual-CpG SNAs showed a Pearson correlation coefficient (p), a measure of the linear correlation between CpG-A uptake and CpG-B uptake, greater than 0.8 (p=0.849±0.005), indicating that dual-CpG SNAs provided better co-delivery of the two components as compared to a 50:50 mixture of the two linear CpG ODNs (not on SNAs) which did not show a strong correlation of co-delivery (FIGS. 2d-f and 7). Confocal microscopy revealed that even after extended periods (e.g., 48 hours), the fluorescence from the two labeled CpG components of 50:50 dual-CpG SNAs still strongly overlapped, quantified by high Manders overlap coefficients, while fluorescence from cells treated with a 50:50 mixture of both linear labeled CpG ODNs showed little overlap (FIGS. 2g-h and 8).

Figure 9:
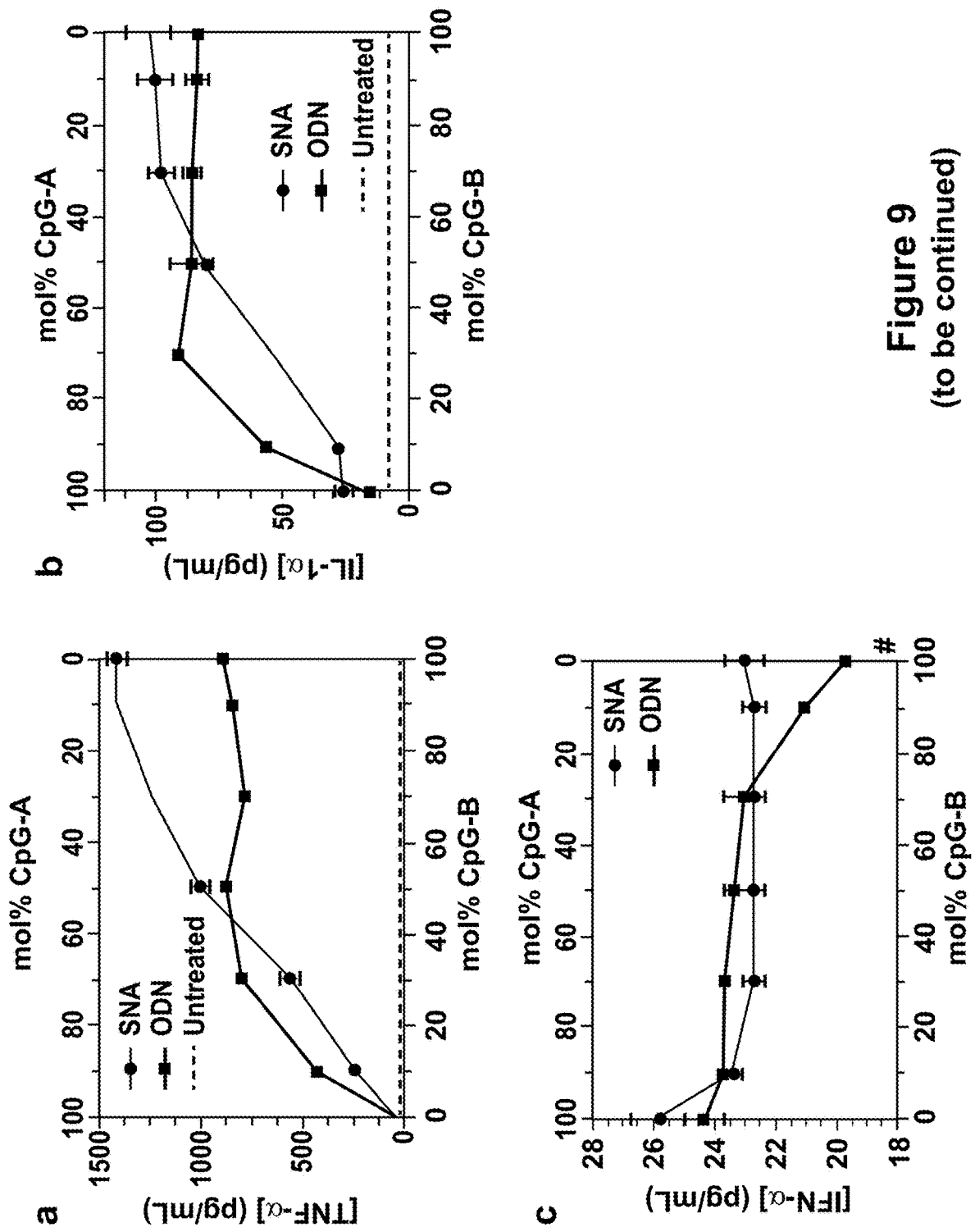
FIG. 9 shows cytokine and IFN production following intracellular localization. Production of (a) TNF-α, (b) IL-1a, and (c) IFN-α (#signal below the lower limit of detection for untreated samples). Manders overlap coefficient of (d) CpG-SNAs or (e) CpG ODN in intracellular markers over time. Dual-CpG data shown in (d) and (e) incorporated a 1:1 ratio of CpG-A to CpG-B.
Figure 10:
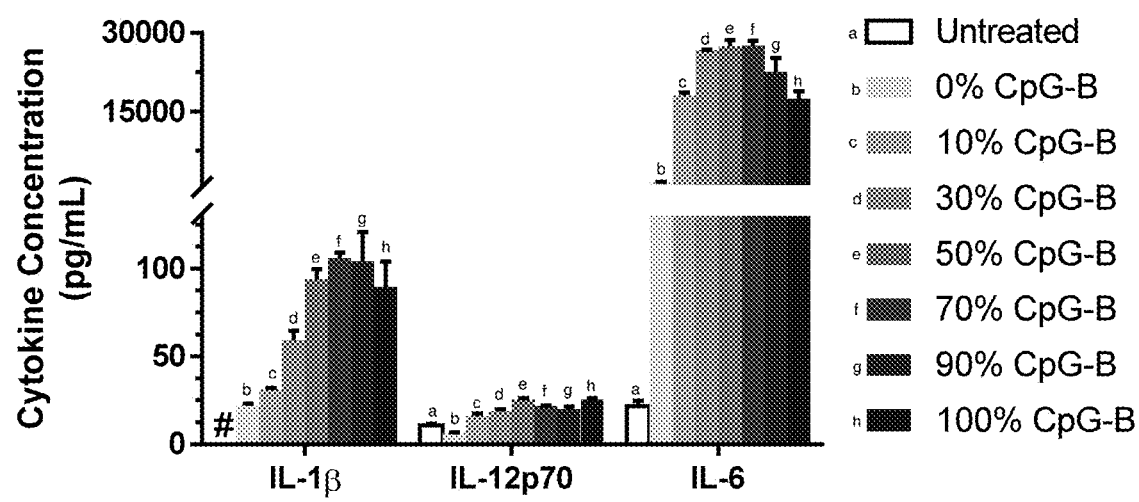
FIG. 10 shows IL-1β, IL-12p70, and IL-6 production.

Although CpG ODNs activate TLR9 and lead to the secretion of cytokines and interferons, different classes of CpG ODN induce different immune responses, due in part to different intracellular trafficking of the oligonucleotides.[29-30] After entering cells, CpG-A binds to TLR9 preferentially in the early endosome, which activates the interferon regulatory factor 7 (IRF7) pathway and leads to the secretion of type I IFN (e.g., IFN-α). In contrast, CpG-B activates TLR9 primarily in the late endosome, where the nuclear factor κB (NF-κB) pathway is predominately activated and secretes proinflammatory cytokines. The detailed mechanisms of different activation pathways are still not completely understood, but it is proposed that both the sequence of the oligonucleotides and the pH of the intracellular organelles may contribute. Both factors likely impact the morphology of the CpG-TLR9 complex and consequently the extra-organelle portion of TLR9 responsible for downstream activation. Thus, a series of dual-CpG SNAs with different ratios of CpG-A to CpG-B loading were generated, ranging from 0% CpG-B (100% CpG-A) to 100% CpG-B (0% CpG-A) to study the effects of codelivery on downstream activation, with oligonucleotide loading confirmed by agarose gel electrophoresis (FIG. 6). After incubating DCs with 1 μM SNAs (by total CpG concentration) for 24 hours, it was found that high CpG-B loading promoted cytokine secretion (FIGS. 9a-b and 10), indicative of activation of the NF-κB pathway, while high CpG-A loading led to high IFN-α production, indicative of activation of the IRF7 pathway (FIG. 9c). Further, cells treated with single-component CpG-A SNAs or CpG-B SNAs stimulated higher cytokine and interferon production as compared to their linear counterparts. Interestingly, although cytokine secretion increased steadily with increasing CpG-B loading in SNAs, the linear ODN mixture reached a maximum level of cytokine secretion at 30% CpG-B, with no enhanced cytokine production observed at higher ratios of CpG-B to CpG-A (FIG. 9a-b). Similar behavior was observed for IFN-α production by linear ODN mixtures as a function of CpG-A ratios (FIG. 9c).

Figure 11:
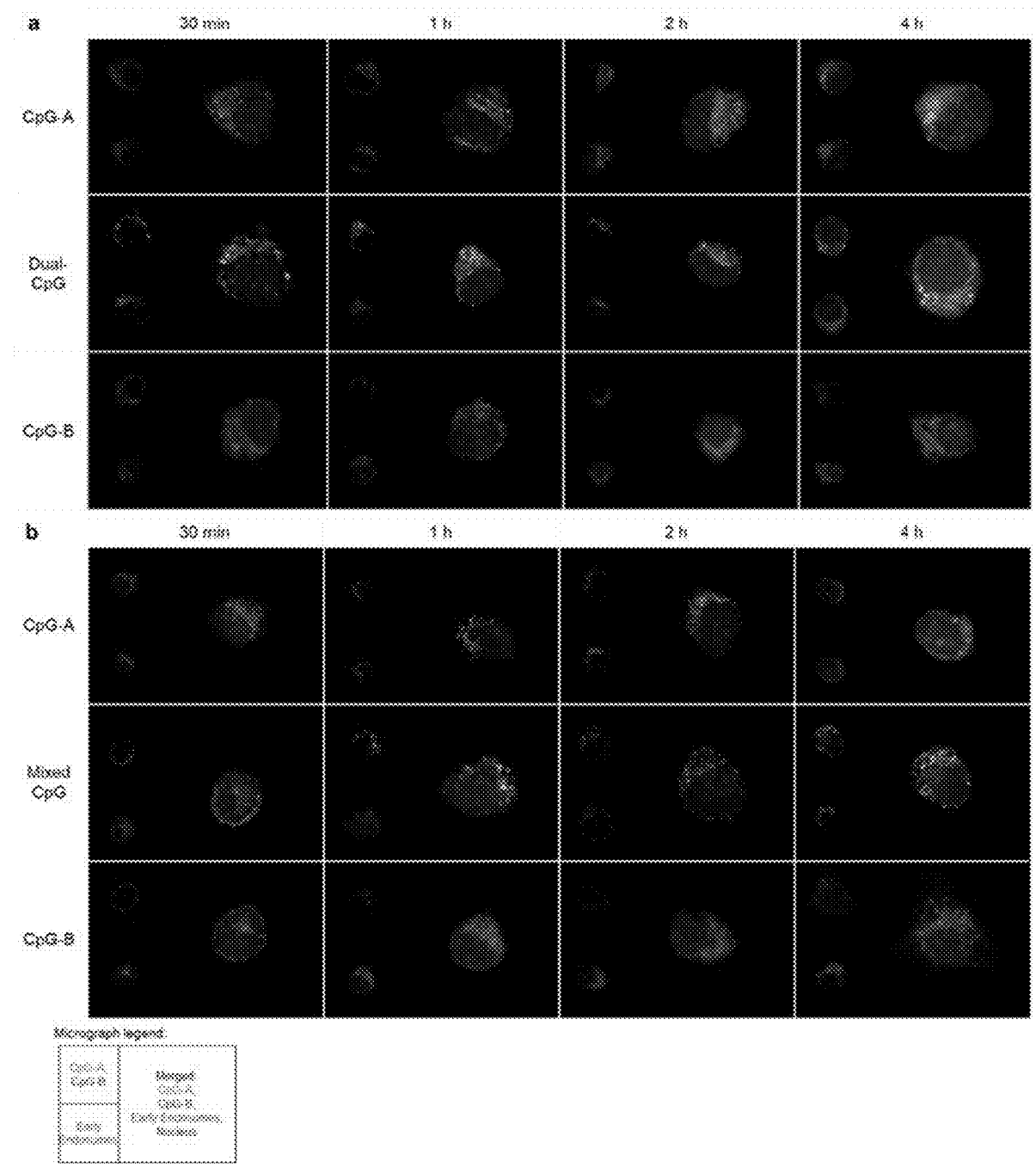
FIG. 11 shows confocal images of JAWS II cells treated with (a) CpG SNAs or (b) linear CpG ODNs and their relative localization in early endosomes.
Figure 12:
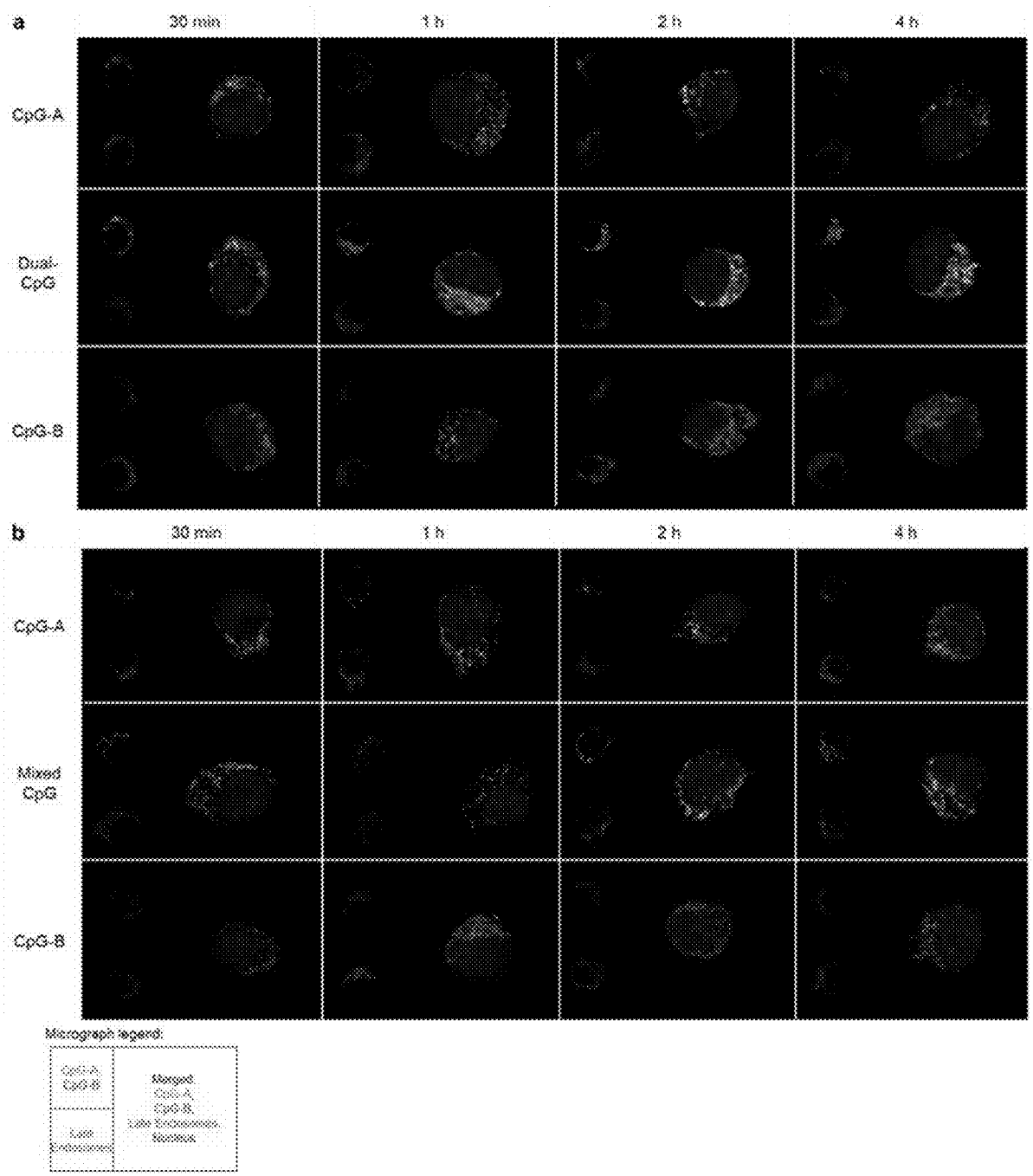
FIG. 12 shows confocal images of JAWS II cells treated with (a) CpG SNAs or (b) linear CpG ODNs and their relative localization in late endosomes.
Figure 13:
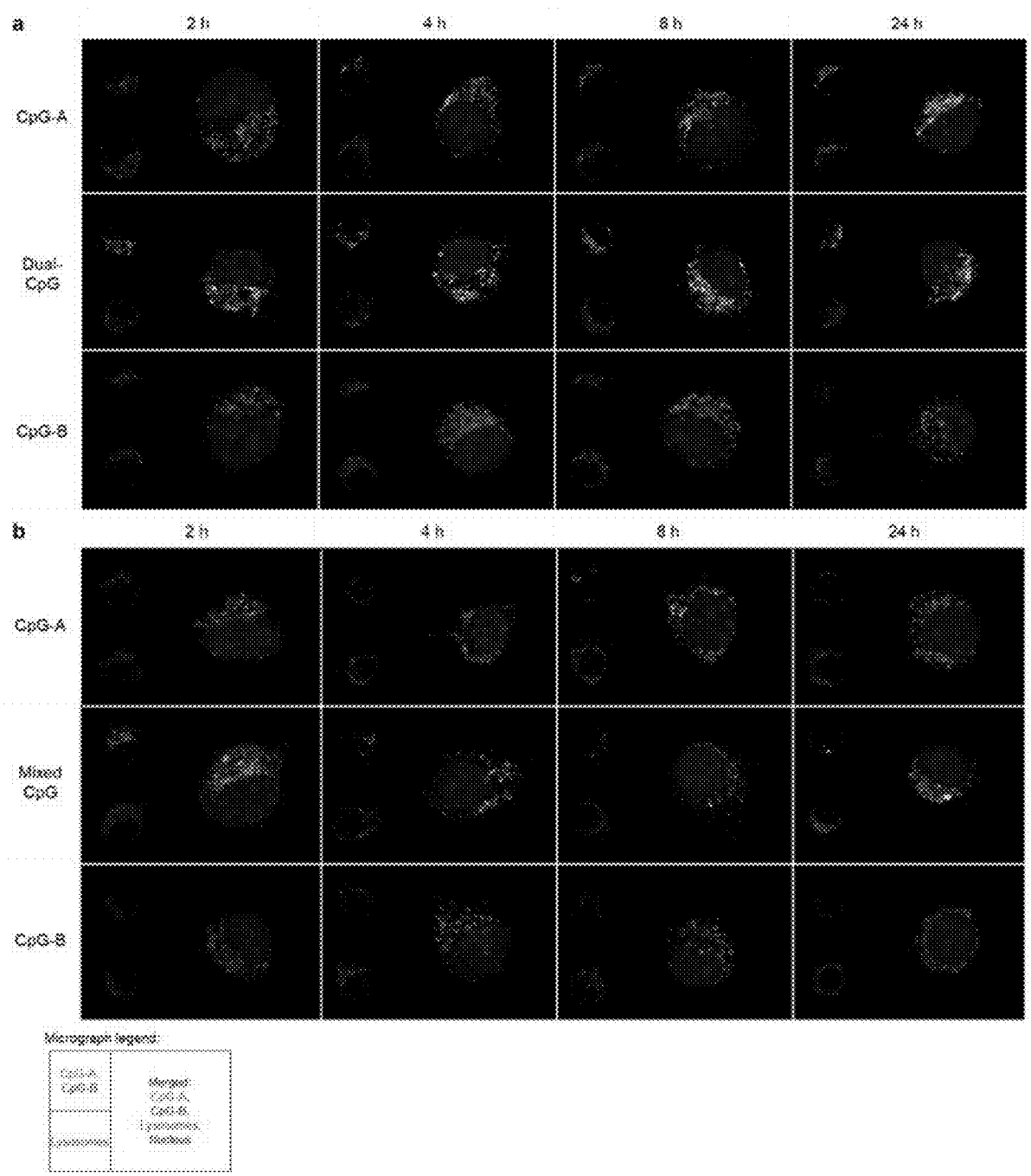
FIG. 13 shows confocal images of JAWS II cells treated with (a) CpG SNAs or (b) linear CpG ODNs and their relative localization in lysosomes.
Figure 14:
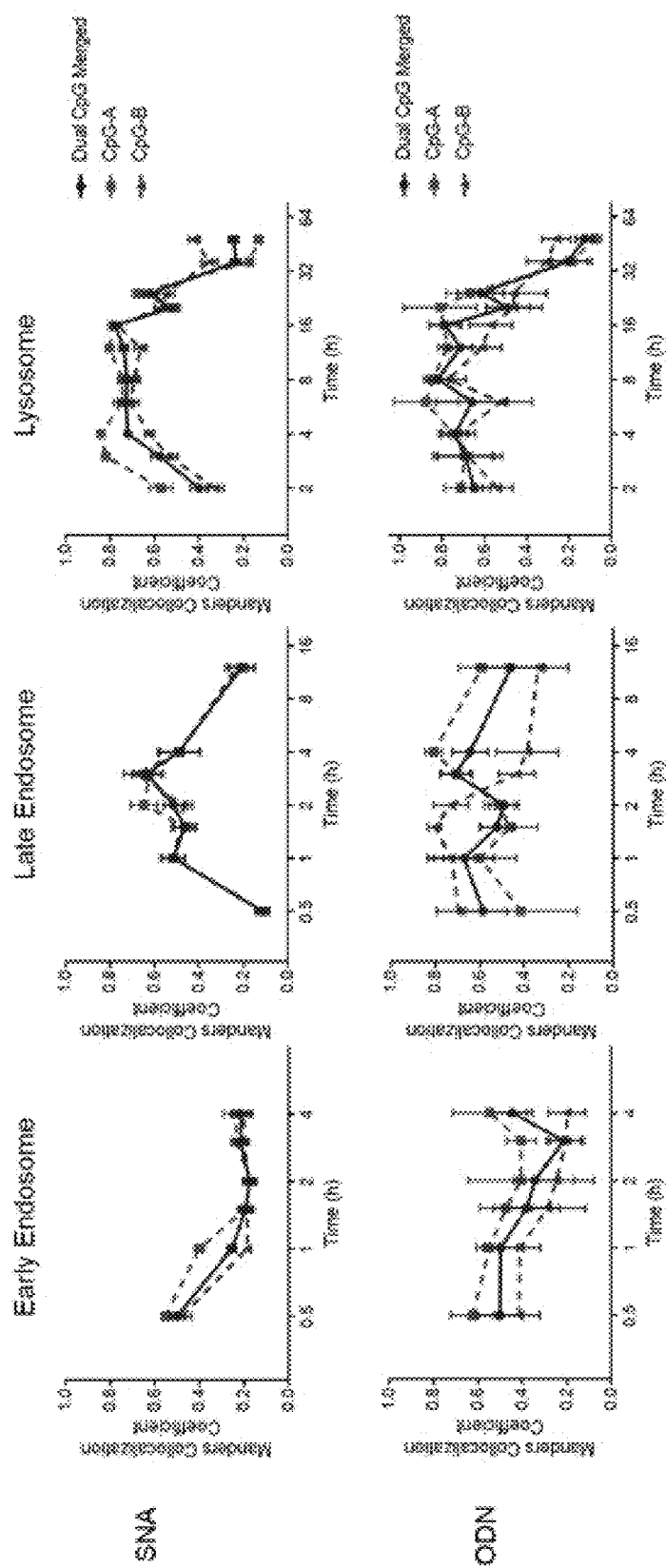
FIG. 14 shows Manders overlap coefficient of dual-CpG in intracellular markers over time as shown in FIG. 9d-e, with CpG-A and CpG-B coefficients plotted separately.

It was hypothesized that the differences in immune activation by SNAs as compared to linear ODNs was a result of the difference in intracellular trafficking of the two constructs. In the case of linear CpG ODNs, each component traveled independently to its preferred intracellular pathway for downstream activation, since the two components were not structurally associated. However, CpG-A and CpG-B were coupled onto the same entity in dual-CpG SNAs and remained highly associated over time (FIG. 2g). Thus, CpG-A and CpG-B were trafficked to the same location, leading to only a portion of each CpG type delivered to its preferred intracellular organelle for TLR9 activation. To confirm this hypothesis, the intracellular trafficking of different SNAs was studied using confocal microscopy (FIGS. 11-13), as well as the localization of CpG in intracellular organelles (FIGS. 9d-e, and 14). It was found that the trafficking of CpG-A and CpG-B ODNs was primarily dictated by the SNA scaffold, with sequence identity having minimal effect on intracellular trafficking when the ODNs were on an SNA. Conversely, the trafficking of mixtures of linear ODNs was dictated by each ODN sequence identity. CpG SNAs, regardless of sequence, were trafficked to early endosomes, late endosomes, and lysosomes at approximately the same rates and on the same timescales (FIG. 9d). In general, SNAs colocalized with the early endosome after uptake, followed by a rapid decrease with a concomitant increase of colocalization with the late endosome. There was only 0.5 hour difference between CpG-A and CpG-B SNAs that colocalized with the early endosome, and all SNAs showed colocalization with the late endosome with a peak at approximately 2-3 hours. Colocalization of SNAs in lysosomes steadily increased, reaching a plateau at 4 hours which was maintained up to 24 hours. On the contrary, mixtures of linear CpG-A and CpG-B ODNs were trafficked very differently (FIG. 9e). After uptake, linear CpG-A ODN maintained high colocalization with the early endosome, where CpG-A/TLR9 binding is preferred, with a slight decrease in colocalization over time. In contrast, linear CpG-B ODN showed high colocalization with the late endosome at early time points, indicating very rapid traveling to late endosomes, where CpG-B/TLR9 binding is favored. These results will guide the design of SNAs for preferentially delivering various oligonucleotide sequences to specific intracellular organelles following this particular spatiotemporal path, which is otherwise impossible to control for the corresponding linear ODN counterparts.

Figure 15:
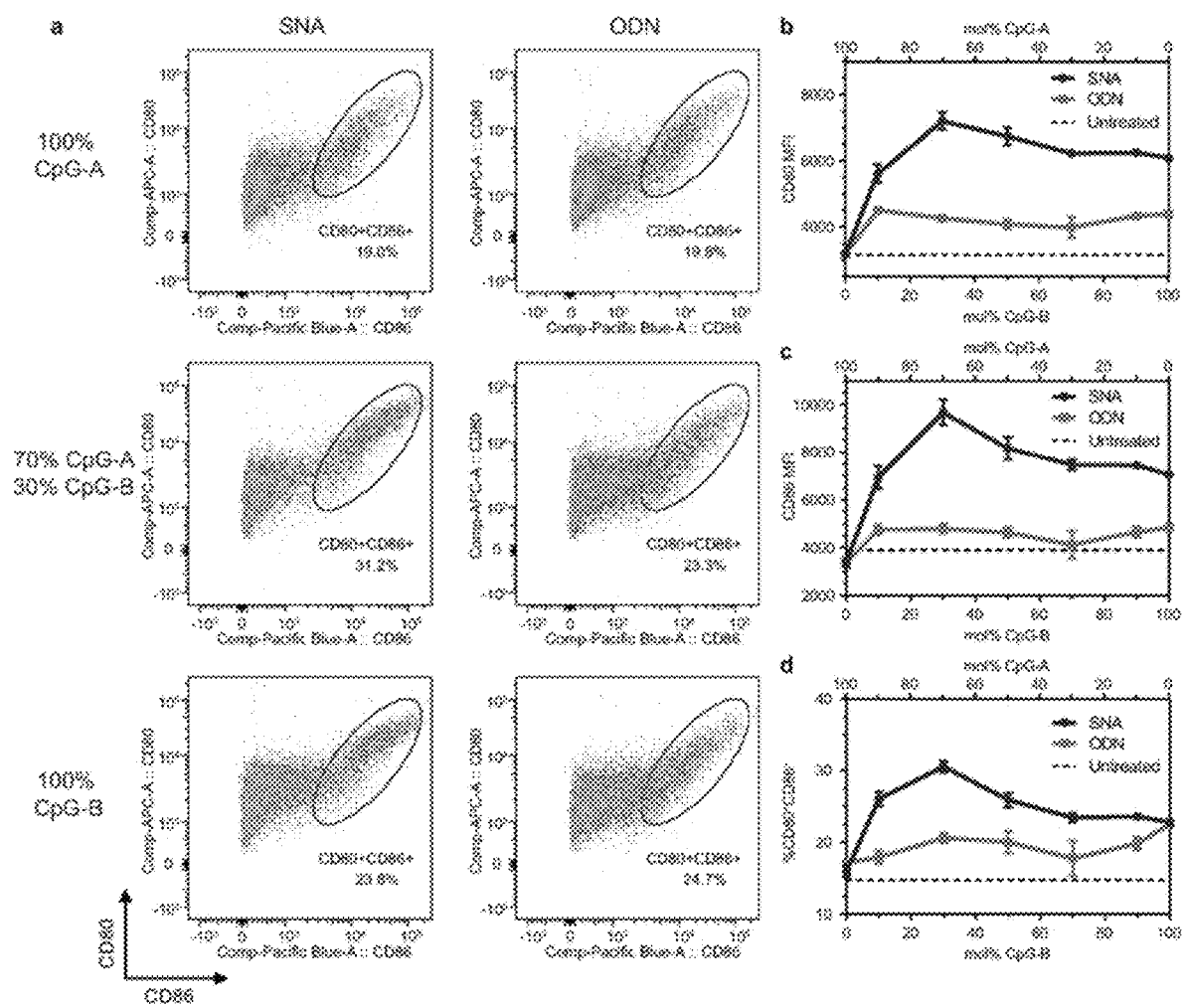
FIG. 15 shows DC costimulation marker activation. (a) Representative flow cytometry data for CD80 and CD86 expression after 24 h treatment of CpG SNAs or linear CpG ODNs. Mean fluorescence intensity (MFI) of (b) CD80 and (c) CD86 expression. (d) Percentage of CD80+/CD86+ double-positive cell population after treatment.
Figure 16:
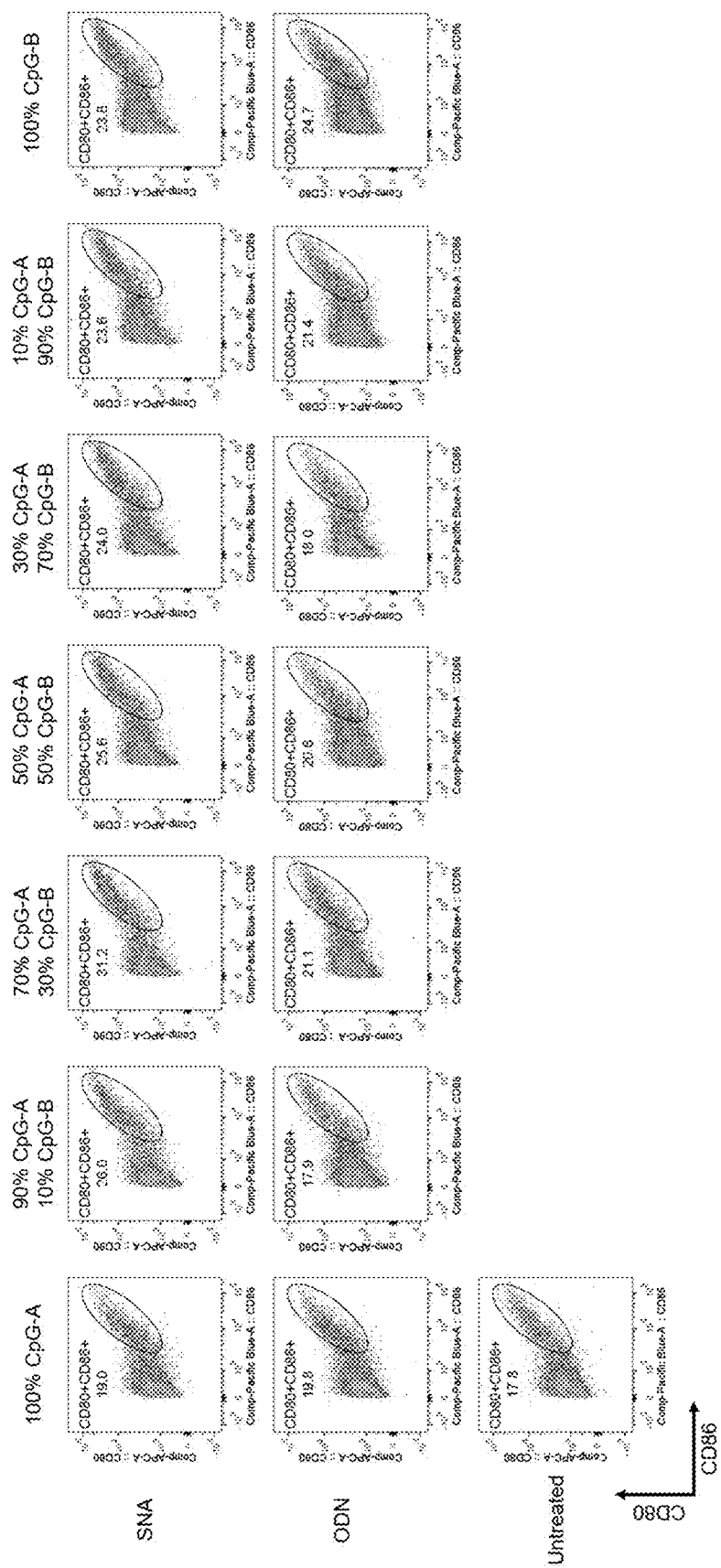
FIG. 16 shows representative flow cytometry data for CD80 and CD86 expression after a 24 hour treatment with CpG SNAs or linear CpG ODNs. Median value from triplicated experiment is shown.

It was further hypothesized that maximum DC activation could be achieved by codelivering an intermediate ratio of CpG-A and CpG-B on the same SNA. Costimulation markers are antigen non-specific signaling proteins that are necessary for antigen-presenting cells (e.g., DCs) to activate T cells.[31] In addition to cytokine, chemokine, and interferon productions, TLR9 activation also leads to the upregulation of CD80 and CD86 (also known as B7-1 and B7-2, respectively), two proteins that can bind to CD28 on T cells for critical costimulation and T cell activation.[32-33] After incubating DCs with dual-CpG SNAs for 24 hours, SNAs at different CpG-A/B ratios demonstrated almost consistently superior performances to incubation with linear CpG ODNs at the same ratios (FIGS. 15 and 16). Expression of CD80 and CD86 peaked at 70 mol % CpG-A and 30 mol % CpG-B ratio on SNAs, and the percentage of the $CD80^+/CD86^+$ double-positive population was also the highest at this CpG ratio. These results showed that dual-CpG SNAs with controlled oligonucleotide ratios can achieve maximal DC maturation, potentially because of the unique intracellular trafficking pathway taken by SNAs, allowing cells to take advantage of activation by both CpG classes. After SNAs enter cells, a relatively higher amount of CpG-A than CpG-B was needed to effectively bind TLR9 in the early endosome and induce significant downstream activation, because SNAs only remain in the early endosome for a brief time (FIG. 9d). Conversely, a relatively lower amount of CpG-B was needed because the SNAs remain colocalized with the late endosome for extended periods, where CpG-B is processed. It was found that 70 mol % CpG-A and 30 mol % CpG-B was the optimal ODN ratio on dual-CpG SNAs to achieve maximal activation (FIG. 15).

Figure 17:
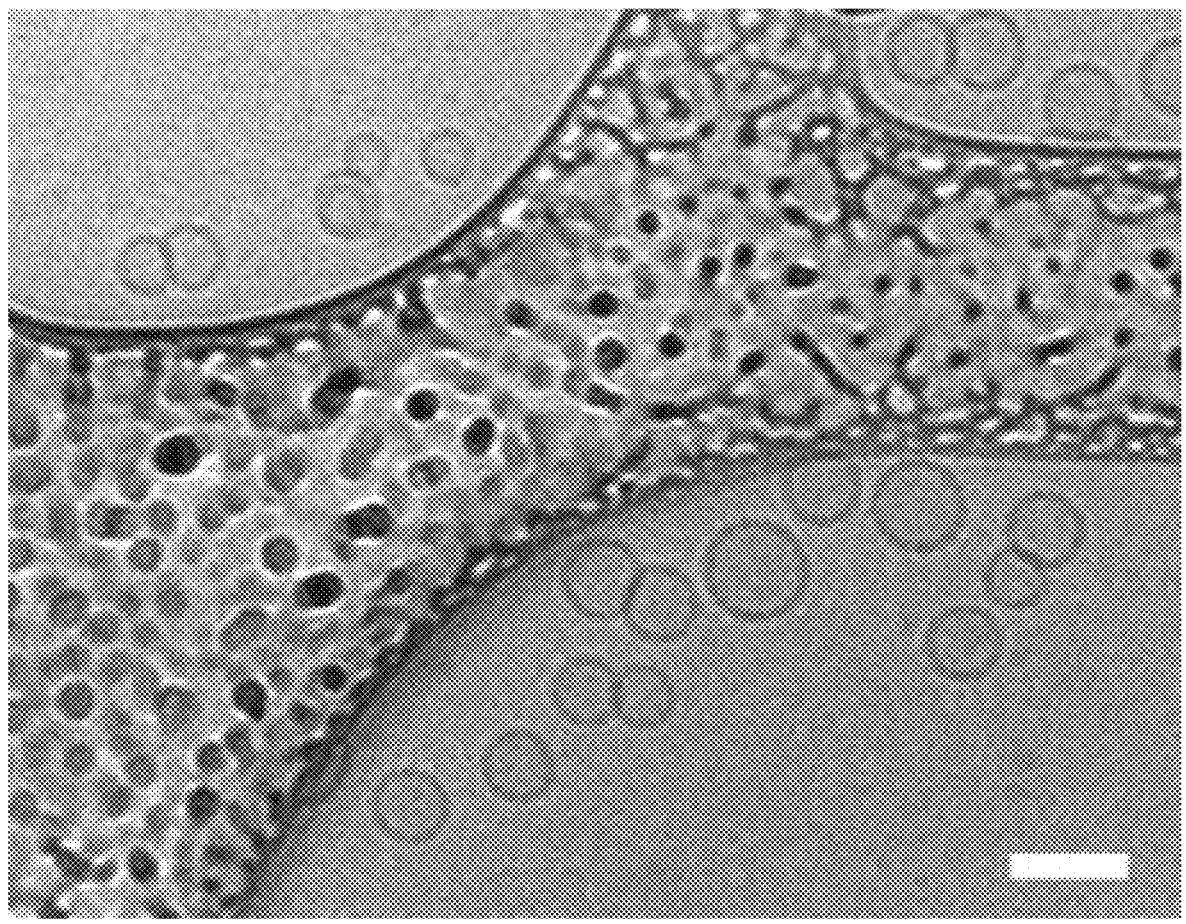
FIG. 17 shows a CryoTEM image of LSNAs functionalized with 300 equivalents of class A CpG ODN. Scale bar: 100 nm.
Figure 18:
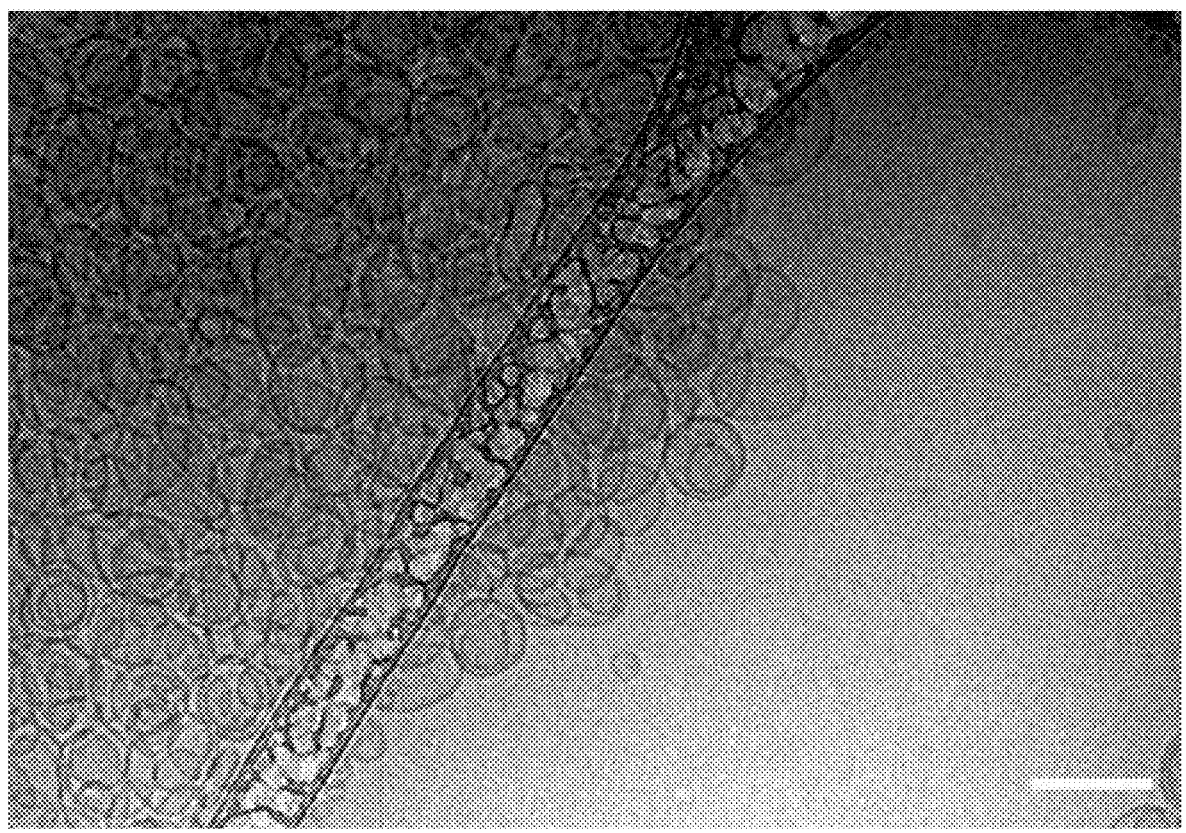
FIG. 18 shows a CryoTEM image of LSNAs functionalized with 10,000 equivalents of class A CpG ODN. Scale bar: 100 nm.

CpG-A SNA at oligonucleotide loading. At DNA loadings exceeding 150 strands per particle, upward shifts in mobility in gel electrophoresis experiments were observed (FIG. 4a), indicating significant size increases in the population, presumably due to SNA aggregation caused by sequence self-complementarity. Evidence of this aggregation is supported by cryogenic transmission electron microscopy (cryoTEM), where a substantial number of particles formed SNA dimers (FIG. 17), which have size difficult to accurately measure by dynamic light scattering (DLS) due to anisotropic shape. Following the addition of exceedingly high equivalents of DNA to liposome (e.g., 10,000 equivalent of DNA/liposome), aggregation of the LSNAs was observed. These aggregates persisted even at elevated temperatures (i.e., 37° C., FIG. 18). SNAs with complementary or self-complementary sequences are known to assemble into aggregates, and various colloidal crystals can be produced with careful thermal treatments and processes, and such polyvalent, hybridization-induced crystallization produces aggregates with higher melting temperatures than the analogous linear ODN duplexes of the same sequence [Mirkin et al., Nature 1996, 382 (6592), 607; Macfarlane et al., Science 2011, 334 (6053), 204; Jones et al., Science 2015, 347 (6224), 1260901; Cutler et al., J. Am. Chem. Soc. 2012, 134 (3), 1376; Laramy et al., ACS Nano 2019, 13 (2), 1412; Park et al., Nature 2008, 451 (7178), 553]. The palindrome sequence of CpG-A is self-complementary, and it was found that the aggregate formation of CpG-A SNAs was indeed mainly due to the palindrome portion of the sequence hybridizing with other particles. To confirm this effect was due to self-complementarity, the poly(G) portion was removed from the sequence and it was observed that at high DNA additions, LSNA aggregation still occurred. Conversely, no aggregation was observed when the same amount of poly(G) sequence was added to the 5'- and 3'-ends of a dummy sequence (e.g., T20 sequence), even after storage at 4° C. for several days. Liposomes functionalized with complementary DNA sequences are known to fuse together, aided by DNA hybridization [Ries et al., Org. Biomol. Chem. 2017, 15 (42), 8936]. However, cryoTEM of CpG-A SNA aggregates (FIG. 18) revealed that the SNAs crowd together, yet individual versus fused particles are still distinguishable. This indicated that the poly(G) sequence on the 3'-end may prevent liposome fusion.

Conclusions

The unique properties of the SNA architecture allow for the delivery of diverse ODN classes at programmable ratios and with high uptake and codelivery to the same target cell. Through generating a series of SNAs incorporating CpG-A and CpG-B on the same nanoparticle scaffold at different ratios, it was determined that the SNA architecture provided high intracellular association of these two distinct ODN classes. Furthermore, codelivery of both CpG classes on the dual-CpG SNA scaffold led to synergistic DC costimulatory molecule activation, where cytokine and IFN secretion is proportional to the fraction of each of their activating CpG classes (CpG-B and CpG-A, respectively). Although the two sequences used in this report are both TLR9 ligands, the high association and intracellular trafficking behaviors are governed by the SNA scaffold and are independent of sequence, as these sequences are trafficked to the same location despite being both physically and chemically diverse. Therefore, these findings should be generalizable to the design and synthesis of SNAs containing any combination of multi-sequence SNAs for desired applications.

Thus, sequence multiplicity spherical nucleic acids (SNAs) are shown herein to provide a power platform for co-delivery of several oligonucleotides with controlled ratios on the same particle to ensure such ratio gets taken up by cells. The ratios of each sequence incorporated can be determined either from experimentation or from rational design. It was shown herein that, regardless of sequence, spherical nucleic acids' intracellular trafficking follows a particular pathway and schedule, unlike their linear counterparts which may traffic very diversely. This can be taken as an advantage of, for example, using a higher fraction of a sequence that binds to a receptor in an organelle where spherical nucleic acid localizes for less time, and vice versa.

Example 2

Methods. $1 \times 10^7$ human PBMCs were treated with 200 nM human CpG SNAs for 24 hours. Dual-CpG SNA included 70% CpG-A and 30% CpG-B. SNAs in this example were generally synthesized using methods as described in Example 1, above.

Sequences. Human CpG-A: ggGGGAC-GATCGTCggggggg (SEQ ID NO: 11), human CpG-B: tcgtcgttttgtcgttttgtcgtt (SEQ ID NO: 12) (Bases shown in capital letters are phosphodiester, and those in lower case are phosphorothioate).

Figure 21:
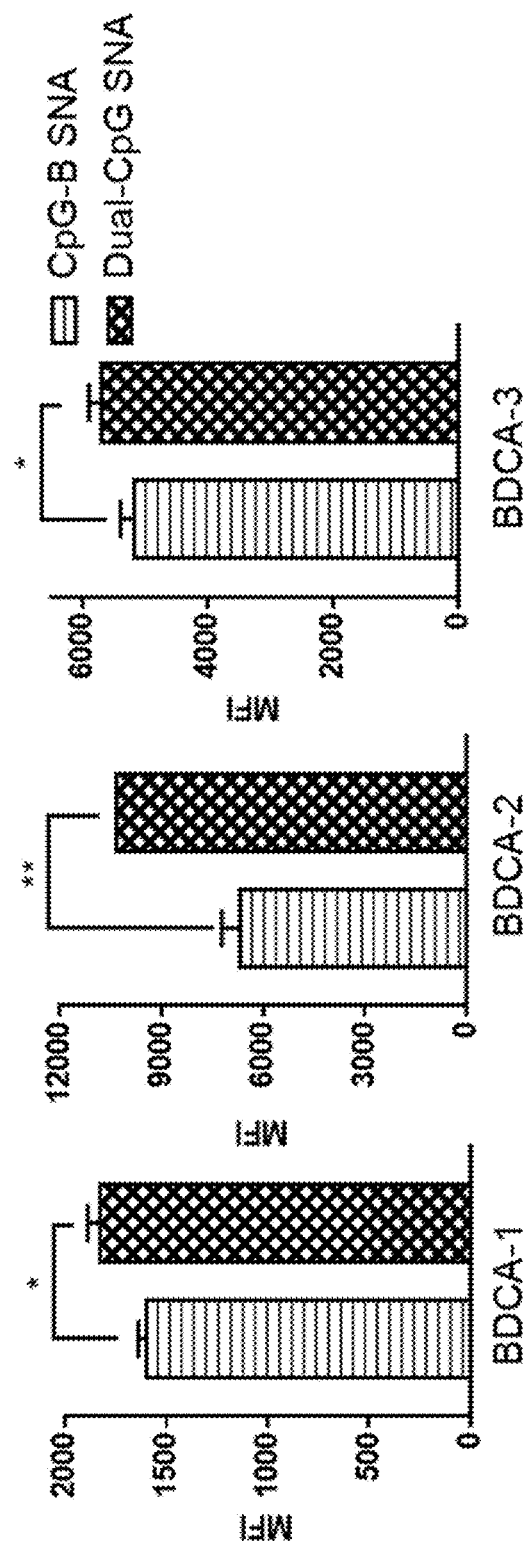
FIG. 21 shows that dual-CpG SNAs promoted significant enhancement in dendritic cell activation (quantified by co-stimulation marker CD80 expression) in all dendritic cell subtypes collected from human peripheral blood mononuclear cells (PBMCs), compared to SNAs containing only CpG-B.

Results/Conclusion. Dual-CpG SNAs promoted significant enhancement in dendritic cell activation (quantified by co-stimulation marker CD80 expression) in all dendritic cell subtypes collected from human peripheral blood mononuclear cells (PBMCs), compared to SNAs containing only CpG-B, demonstrating that the dual-CpG SNAs are translatable to human cells as more potent immunotherapy nanomaterials. See FIG. 21.

What is claimed is:

1. A spherical nucleic acid (SNA) comprising a nanoparticle core and an oligonucleotide shell attached to the external surface of the nanoparticle core, wherein the oligonucleotide shell comprises a mixture of class A CpG oligonucleotides and class B CpG oligonucleotides, wherein the ratio of class A CpG oligonucleotides to class B CpG oligonucleotides in the mixture is about 7:3 and wherein the SNA does not comprise a class C CpG oligonucleotide.

2. The SNA of claim 1, wherein the oligonucleotide shell consists of a mixture of class A CpG oligonucleotides and class B CpG oligonucleotides.

3. The SNA of claim 1, wherein the class A CpG oligonucleotides each comprise (i) an internal palindrome sequence containing a CpG motif and (ii) an at least partially phosphorothioated poly (G) sequence at its 5' and/or 3' ends.

4. The SNA of claim 1, wherein the class A CpG oligonucleotide is DNA.

5. The SNA of claim 1, wherein the class B CpG oligonucleotides each comprise a fully phosphorothioated sequence comprising one or more CpG motifs.

6. The SNA of claim 1, wherein the class B CpG oligonucleotide is DNA.

7. The SNA of claim 1, wherein the oligonucleotide shell comprises about 10 to about 150 oligonucleotides.

8. The SNA of claim 1, wherein each class A CpG oligonucleotide is about 10 to about 50 nucleotides in length.

9. The SNA of claim 1, wherein each class B CpG oligonucleotide is about 10 to about 50 nucleotides in length.

10. The SNA of claim 1, further comprising an inhibitory oligonucleotide.

11. The SNA of claim 10, wherein the inhibitory oligonucleotide is an antagonist oligonucleotide, antisense DNA, small interfering RNA (siRNA), an aptamer, a short hairpin RNA (shRNA), a DNAzyme, or an aptazyme.

12. The SNA of claim 1, wherein the nanoparticle core is a metallic core, a semiconductor core, an insulator core, an upconverting core, a micellar core, a dendrimer core, a liposomal core, a polymer core, a metal-organic framework core, a protein core, or a combination thereof.

13. The SNA of claim 1, further comprising an additional agent, wherein the additional agent is a protein, a small molecule, a peptide, or a combination thereof.

14. The SNA of claim 1, wherein the SNA is from about 1 to about 150 nanometers (nm) in diameter.

15. The SNA of claim 1, wherein the oligonucleotide shell comprises about 10 to about 50 oligonucleotides.

16. The SNA of claim 1, wherein the oligonucleotide shell comprises about 75 to about 100 oligonucleotides.

17. The SNA of claim 1, wherein the oligonucleotide shell comprises about 10 to about 1000 oligonucleotides.

18. The SNA of claim 1, wherein each class A CpG oligonucleotide is about 15 to about 26 nucleotides in length.

19. The SNA of claim 1, wherein each class B CpG oligonucleotide is about 18 to about 28 nucleotides in length.

20. A method of inhibiting expression of a gene comprising the step of hybridizing a polynucleotide encoding the gene product with the spherical nucleic acid (SNA) of claim 1, wherein hybridizing between the polynucleotide and one or more oligonucleotides in the oligonucleotide shell occurs over a length of the polynucleotide with a degree of complementarity sufficient to inhibit expression of the gene product.

21. A method for up-regulating activity of a toll-like receptor (TLR), comprising contacting a cell having the toll-like receptor with the spherical nucleic acid (SNA) of claim 1, wherein the toll-like receptor is toll-like receptor 9 (TLR9).

22. A method of treating a disorder comprising administering an effective amount of the SNA of claim 1 to a subject in need thereof, wherein the administering treats the disorder.

23. The method of claim 22, wherein the disorder is cancer, an infectious disease, an autoimmune disease, or a combination thereof.

* * * * *

UNITED STATES PATENT AND TRADEMARK OFFICE
CERTIFICATE OF CORRECTION

PATENT NO. : 12,378,560 B2  
APPLICATION NO. : 17/084460  
DATED : August 5, 2025  
INVENTOR(S) : Chad A. Mirkin et al.

Page 1 of 1

It is certified that error appears in the above-identified patent and that said Letters Patent is hereby corrected as shown below:

In the Claims

At Column 45, Line 29, "poly (G)" should be -- poly(G) --.

Signed and Sealed this  
Third Day of February, 2026

John A. Squires  
*Director of the United States Patent and Trademark Office*